(12) United States Patent
Lu et al.

(10) Patent No.: US 10,864,279 B2
(45) Date of Patent: Dec. 15, 2020

(54) LINKER-DRUG AND ANTIBODY-DRUG CONJUGATE (ADC) EMPLOYING THE SAME

(71) Applicant: Industrial Technology Research Institute, Hsinchu (TW)

(72) Inventors: Maggie Lu, Zhudong Township (TW); May-Hua Chang, Hsinchu (TW); Jenn-Tsang Hwang, Hsinchu (TW); Ping-Fu Cheng, Taipei (TW); Li-Wen Chang, New Taipei (TW); Yi-Ju Ko, New Taipei (TW); Chi-Y Hung, Hsinchu (TW); Chun-Min Liu, Hsinchu (TW); Chia-Yu Fan, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 15/830,272

(22) Filed: Dec. 4, 2017

(65) Prior Publication Data
US 2018/0169262 A1 Jun. 21, 2018

Related U.S. Application Data

(60) Provisional application No. 62/435,274, filed on Dec. 16, 2016.

(51) Int. Cl.
*A61K 47/68* (2017.01)
*A61K 31/4745* (2006.01)
(Continued)

(52) U.S. Cl.
CPC ...... *A61K 47/6889* (2017.08); *A61K 31/4745* (2013.01); *A61K 47/64* (2017.08);
(Continued)

(58) Field of Classification Search
None
See application file for complete search history.

(56) References Cited

U.S. PATENT DOCUMENTS

| | | | | |
|---|---|---|---|---|
| 5,276,013 A | * | 1/1994 | Conrad | A61P 37/00 |
| | | | | 514/21.2 |
| 6,060,056 A | * | 5/2000 | Coutts | A61K 39/35 |
| | | | | 424/184.1 |

(Continued)

FOREIGN PATENT DOCUMENTS

| | | |
|---|---|---|
| JP | 61-106556 A | 5/1986 |
| JP | 7-126186 A | 5/1995 |

(Continued)

OTHER PUBLICATIONS

Extended European Search Report for European Application No. 17207834.7, dated May 2, 2018.

(Continued)

*Primary Examiner* — Karl J Puttlitz
(74) *Attorney, Agent, or Firm* — Birch, Stewart, Kolasch & Birch, LLP

(57) ABSTRACT

A linker-drug represented by formula (I) or a pharmaceutically acceptable salt or solvate thereof is provided. In formula (I), C is a conjugator, L is a linker unit, D is a toxin unit, and n is an integer ranging from 1 to 4. The structure of the conjugator is represented by formula (II). In formula (II), X is a leaving group, each of $R^1$ and $R^2$ is independently a single bond or —NH—, and Z is substituted aryl, heteroaryl, linear alkyl, cycloalkyl, heterocycloalkyl, or a combination thereof. The antibody is conjugated to the linker unit through a cysteine residue of the antibody. An antibody-drug conjugate (ADC) employing the above linker-drug is also provided.

(Continued)

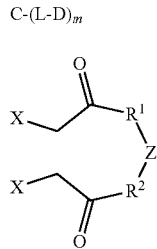

16 Claims, 27 Drawing Sheets

(51) Int. Cl.
*A61K 47/64* (2017.01)
*C07K 16/30* (2006.01)
*A61P 35/00* (2006.01)
*A61K 47/65* (2017.01)

(52) U.S. Cl.
CPC ...... *A61K 47/6803* (2017.08); *A61K 47/6817* (2017.08); *A61K 47/6851* (2017.08); *A61K 47/6855* (2017.08); *A61P 35/00* (2018.01); *C07K 16/30* (2013.01); *A61K 47/65* (2017.08)

(56) References Cited

U.S. PATENT DOCUMENTS

| | | |
|---|---|---|
| 7,659,241 B2 | 2/2010 | Senter et al. |
| 8,142,784 B2 | 3/2012 | Ebens, Jr. et al. |
| 8,609,105 B2 | 12/2013 | Senter et al. |
| 8,703,714 B2 | 4/2014 | Doronina et al. |
| 8,742,076 B2 | 6/2014 | Cohen et al. |
| 8,795,673 B2 | 8/2014 | Li et al. |
| 9,000,130 B2 | 4/2015 | Bhakta et al. |
| 9,005,598 B2 | 4/2015 | Godwin et al. |
| 9,295,729 B2 | 3/2016 | Smith et al. |
| 2008/0300192 A1 | 12/2008 | Doronina et al. |
| 2012/0121615 A1 | 5/2012 | Flygare et al. |
| 2013/0224228 A1 | 8/2013 | Jackson et al. |
| 2014/0363454 A1 | 12/2014 | Jackson et al. |
| 2015/0105539 A1 | 4/2015 | Miao et al. |
| 2015/0283259 A1 | 10/2015 | Burt et al. |
| 2016/0015832 A1 | 1/2016 | An et al. |

FOREIGN PATENT DOCUMENTS

| | | |
|---|---|---|
| TW | 201534327 A | 9/2015 |
| WO | WO 86/00898 A1 | 2/1986 |
| WO | WO 95/07073 A1 | 3/1995 |
| WO | WO 2013/190272 A1 | 12/2013 |
| WO | WO 2014/114207 A1 | 7/2014 |
| WO | WO 2015/095406 A1 | 6/2015 |
| WO | 2017031034 * | 2/2017 |
| WO | WO 2017/031034 A2 | 2/2017 |
| WO | WO 2017/055582 A1 | 4/2017 |

OTHER PUBLICATIONS

Alley et al., "Contribution of Linker Stability to the Activities of Anticancer Immunoconjugates", Bioconjugate Chemistry, 2008, pp. 759-765.

Doronina et al., "Development of potent monoclonal antibody auristatin conjugates for cancer therapy", Nature Biotechnology, 2003, vol. 21, pp. 778-784.

Doronina et al., "Novel Peptide Linkers for Highly Potent Antibody-Auristatin Conjugate", Bioconjugate Chemistry, 2008, vol. 19, pp. 1960-1963.

Sun et al., "Reduction-Alkylation Strategies for the Modification of Specific Monoclonal Antibody Disulfides", Bioconjugate Chemistry, 2005, pp. 1282-1290.

Jones et al., "Conjugates of Double-Stranded Oligonucleotides with Poly(ethyleneglycol) and Keyhole Limpet Hemocyanin: A Model for Treating Systemic Lupus Erythematosus.", Bioconjugate Chem., 1994, pp. 390-399.

Notice of Reasons for Rejection, dated Jan. 8, 2019, issued in the corresponding Japanese Application No. 2017-241514.

* cited by examiner

LINKER-DRUG AND ANTIBODY-DRUG CONJUGATE (ADC) EMPLOYING THE SAME

CROSS REFERENCE TO RELATED APPLICATIONS

This application claims the benefit of U.S. Provisional Application No. 62/435,274, filed Dec. 16, 2016, the entirety of which is incorporated by reference herein.

TECHNICAL FIELD

The technical field relates to a linker-drug and antibody-drug conjugate (ADC) employing the same.

BACKGROUND

In cancer treatments, many cytotoxic drug molecules cannot be used for cancer therapy because they cannot selectively kill cancer cells. Therefore, antibody-drug conjugate (ADC) has been developed as novel cancer therapeutic agents. Generally, an ADC is composed of three parts: an antibody, linkers, and drugs, wherein the linkers conjugate the antibody to the drugs. The mechanism of action of an ADC is described as follows. First, an antibody recognizes the specific or over-expressed antigens on the tumor cell and binds to the antigens. Once binding to the antigens, the binding complex will internalize and thus deliver the linked drugs into the tumor cell. In the tumor cell, the antibody will be digested or the linkers will be cleaved, and then the drugs would be released in an active form and kill the target tumor cell to achieve the selective toxic effects.

Linkers used in ADCs need to meet several requirements: the linkers need to be stable when circulating in human plasma to prevent early release of drugs; upon internalized into the tumor cell, the cleavable linkers could be cleaved under certain condition to release the drugs, while for non-cleavable linkers, the drug moieties are released in an active form that contains drug, linker and amino acid residue derived from the protease-degraded ligand.

In the currently used clinical ADC structures, drugs are linked via different linkers to the lysine residues or hinge-region cysteine residues (after full/partial reduction of inter-chain disulfide bonds). The optimized DARs (drug to antibody ratio) are preferred to be 2~4. The large number of lysine residues on the surface of antibodies and the non-selective conjugation mode lead to the uncertainty of conjugation sites and conjugated drug numbers. For example, there are dozens of possible conjugation sites in Kadcyla® (ado-trastuzumab emtansine; Roche) which belongs to a lysine-based conjugation. Similarly, although an antibody contains only four reducible inter-chain disulfide bonds in the hinge area, it must be partially reduced and conjugated to give ADCs with optimal average DAR 2~4. As generally used reducing agents (DTT, TCEP, etc) couldn't selectively reduce the hinge-region disulfide bonds, the conjugation products thus obtained are not homogeneous either. For example, Adcetris® (brentuximab vedotin; Seattle Genetics) which belongs to a cystein-based conjugation and contains conjugates with DAR of 0, 2, 4, 6 and 8. Even for a fraction with specific DAR value, it is a mixture that contains conjugates with drugs coupled at different conjugation sites. The heterogeneity of ADC products may ultimately lead to different pharmacokinetics, efficacy, and toxicity properties for different fractions. Moreover, the heterogeneity of ADC products may also lead to aggregation and a declined half-life.

To overcome the issue of high heterogeneity of ADC products, site-specific conjugation technologies have been the hot spots recently, which control both conjugation sites and stoichiometrics of drug loading. However, the antibodies or proteins in these technologies are most genetically engineered. Such mutagenesis may be time consuming and not cost effective, as substantial work and special care need to be taken to screen the antibodies with favorable mutation sites for further drug conjugation or pegylation.

In addition, maleimide is used as a conjugation site for antibodies in most clinical ADCs. However, maleimide is easily dissociated, resulting in a short half-life. In such case, the linkers between the antibody and the drugs are broken before the ADCs internalized into the tumor cell, the early released drugs could not specifically kill the target tumor cell and the selective toxic effects could not be achieved.

Therefore, a novel ADC with high homogeneity and high stability to improve the drug efficacy and stability in human plasma is needed.

SUMMARY

In accordance with an embodiment, the disclosure provides a linker-drug represented by formula (I):

$$C\text{-}(L\text{-}D)_m \quad (I)$$

In formula (I), C is a conjugating linker; L is a linker unit; D is a drug unit; and m is an integer ranging from 1 to 4. The structure of the conjugating linker is represented by formula (II):

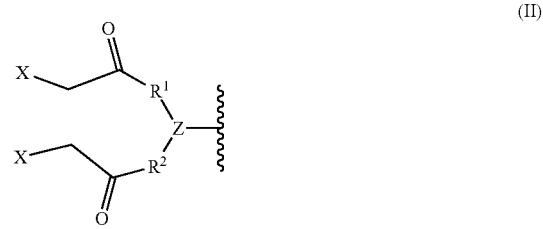

In formula (II), X is a leaving group; $R^1$ and $R^2$ are both single bond or —NH—; Z is aryl, substituted aryl, heteroaryl, substituted heteroaryl, linear alkyl, cycloalkyl, heterocycloalkyl, or a combination thereof. The wave line of formula (II) indicates the covalent attachment site to L In accordance with another embodiment, the disclosure provides an antibody-drug conjugate (ADC) represented by formula (IV):

$$A\text{-}C'\text{-}(L\text{-}D)_m \quad (IV)$$

In formula (IV), A is a full-length antibody, an antibody fragment, a protein, or a polypeptide; C'-(L-D)$_m$ is a linker-drug, wherein C' is a conjugating linker; L is a linker unit; D is a drug unit; and m is an integer ranging from 1 to 4. A is conjugated to the linker-drug through two thiol groups respectively present in two cysteine residues of A.

In formula (IV), A-C' includes the following structure represented by formula (V):

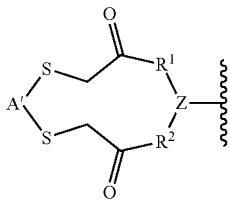

(V)

In formula (V), both of $R^1$ and $R^2$ are single bond or —NH—; Z is aryl, substituted aryl, heteroaryl, substituted heteroaryl, linear alkyl, cycloalkyl, heterocycloalkyl, or a combination thereof. The wave line of formula (V) indicates the covalent attachment site to L; A' indicates the remaining part of A which is conjugated to the linker-drug through two thiol groups respectively present in two cysteine residues of A.

A detailed description is given in the following embodiments with reference to the accompanying drawings.

BRIEF DESCRIPTION OF THE DRAWINGS

The present disclosure can be more fully understood by reading the subsequent detailed description and examples with references made to the accompanying drawings, wherein.

DETAILED DESCRIPTION

Figure 1:
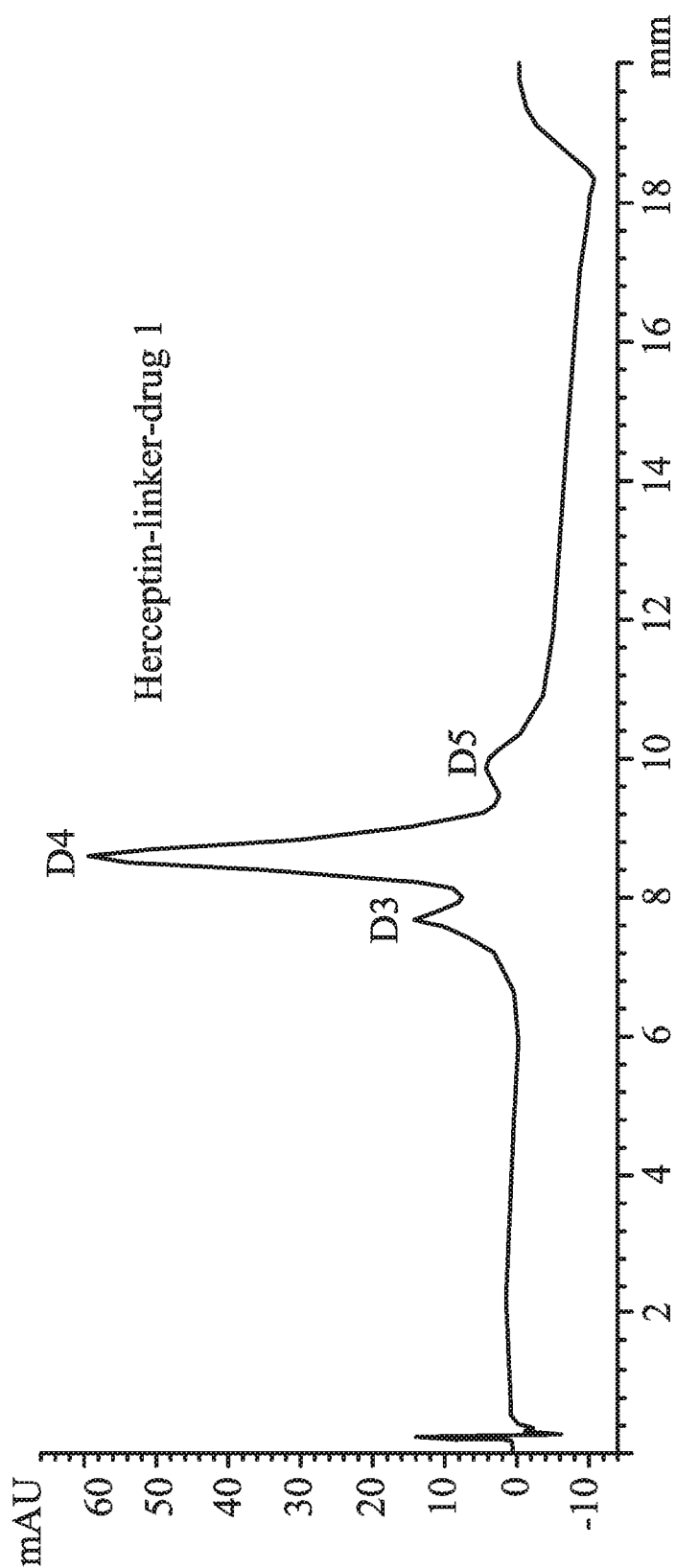
FIG. 1 shows a HIC profile of Herceptin-Linker-drug 1 in accordance with one embodiment of the present disclosure
Figure 2:
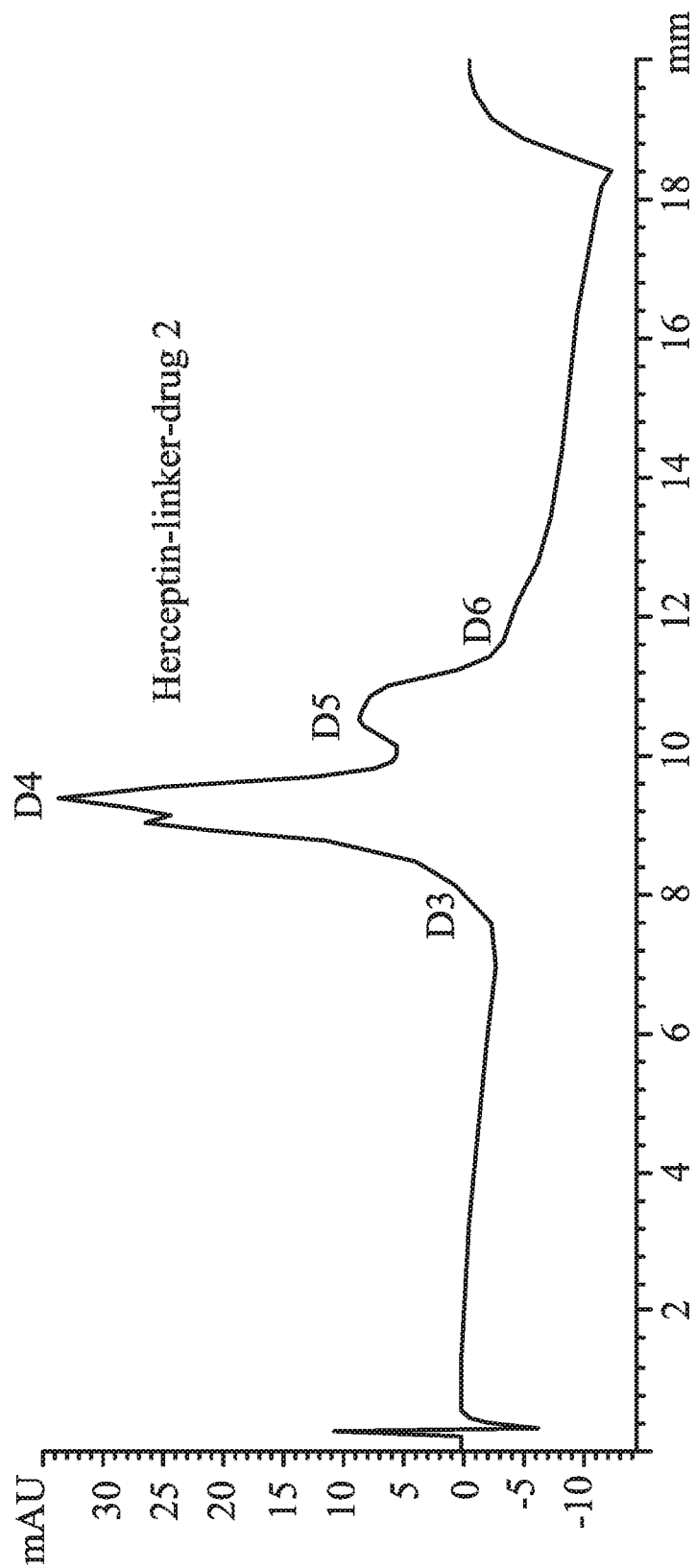
FIG. 2 shows a HIC profile of Herceptin-Linker-drug 2 in accordance with one embodiment of the present disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are shown schematically in order to simplify the drawing.

The present disclosure provides a novel conjugating linker structure which has two linking points that can specifically conjugate to two thiol groups respectively present in two cysteine residues (after full/partial reduction of inter-chain disulfide bonds) of antigen. Thus, the antibody-drug conjugates (ADCs) obtained from the novel conjugating linker structure provided by the present disclosure have improved structural stability. Moreover, a narrower DAR (drug to antibody) distributions compared to those of traditional antibody-drug conjugates is also obtained.

The said novel conjugating linker structures are designed to include two acetamide groups. The two acetamide groups are used to specifically conjugate to the interchain thiol groups (after reduction of interchain disulfide bond), forming a structure similar to a disulfide bond, and thus provide a stable conjugation between the linker and the antibody. Meanwhile, the other part, for example, the functional group in C-terminal, of the said conjugating linker structures may conjugate to a drug unit or a linker-drug unit to give antibody-drug conjugates.

The antibody-drug conjugates thus obtained can be used to selectively deliver drugs to target cells, for example, tumor cells. The antibody-drug conjugates will bind specifically to the cell surface antigens, and the binding complex will be internalized rapidly by the cells. Once internalized, the drug will be released in certain active form and take effects. Compared to traditional ones, the antibody-drug conjugates provided by the present disclosure have not only improved structural stability, but also improved pharmacologically homogeneity.

Definition

In the following description, the term "antibody" can include a full-length antibody or an antibody fragment that binds or reactively associates or complexes with a receptor, antigen or other receptive moiety associated with target cells. An antibody can be any protein, protein-like molecule, or polypeptide that binds to, complexes with, or reacts with a moiety of a cell population sought to be therapeutically modified.

In some embodiments, the antibody can be a chimeric antibody or a functionally active fragment thereof, a humanized antibody or a functionally active fragment thereof, a human antibody or a functionally active fragment thereof. In other embodiments, the antibody can be an antibody from other species, for example, a mouse antibody or a functionally active fragment thereof, a rat antibody or a functionally active fragment thereof, a goat antibody or a functionally active fragment thereof, or a rabbit antibody or a functionally active fragment thereof.

Still in other embodiments, the antibody can be an IgG1 antibody or a functionally active fragment thereof or an IgG4 antibody or a functionally active fragment thereof. For example, the antibody can be, but not limited to, Herceptin, Erbitux, HLX-07, EG12014, anti-EpCAM Ab and IgG1, Rituximab, Ibritumomab tiuxetan, Tositumomab, Brentuximab, Alemtuzumab, IGN101, Adecatumumab, Labetuzumab, huA33, Pemtumomab, Oregovomab, CC49 (mintretumomab), cG250, J591, MOv18, MORAb-003 (farletuzumab), 3F8, ch14.18, KW-2871, hu3S193, IgN311, Bevacizumab, IM-2C6, CDP791, Etaracizumab, Volociximab, Cetuximab, Panitumumab, Nimotuzumab, 806, Trastuzumab, Pertuzumab, MM-121, AMG 102, METMAB, SCH 900105, AVE1642, IMC-A12, MK-0646, R1507, CP 751871, KB004, IIIA4, Mapatumumab (HGS-ETR1), HGS-ETR2, CS-1008, Denosumab, Sibrotuzumab, F19, 8106, humanized anti HER2 mAb, OvaRex, Panorex, Vitaxin, Campath I/H, Smart MI95, LymphoCide, Smart ID10, Oncolym, Allomune, Avastin, Epratuzamab, or CEAcid.

In some embodiments, the antibody can be polyclonal antibodies or monoclonal antibodies. In some embodiments, the antibody can be a bispecific antibody. In some embodiments, the antibody also can be a functionally active fragment, derivative or analog of an antibody that immunospecifically binds to a target antigen (for example, a cancer antigen, a viral antigen, a microbial antigen, or other antibodies bound to cells or matrix). In this regard, the term "functionally active" means that the fragment, derivative or analog is able to recognize the same antigen that the antibody from which the fragment, derivative or analog is derived recognized. Other useful antibodies include fragments of antibodies such as, but not limited to, F(ab')2 fragments, Fab fragments, Fab', Fv fragments, heavy chain and light chain dimers of antibodies, or any minimal fragment thereof such as Fvs or single chain antibodies (SCAs).

In other embodiments, the antibody is a fusion protein of an antibody, or a functionally active fragment thereof. For example, an antibody can be fused via a covalent bond (e.g., a peptide bond) at either the N-terminus or the C-terminus to an amino acid sequence of another protein (or portion thereof, such as at least a 10, 20 or 50 amino acid portion of the protein) that is not the antibody.

In some embodiments, antibodies also include analogs and derivatives that are either modified, i.e., by the covalent attachment of any type of molecule as long as such covalent attachment permits the antibody to retain its antigen binding immuno-specificity. For example, but not by way of limitation, the derivatives and analogs of the antibodies include those that have been further modified, e.g., by glycosylation, acetylation, pegylation, phosphorylation, amidation, derivatization by known protecting/blocking groups, proteolytic cleavage, linkage to a cellular antibody unit or other protein, etc. Any of numerous chemical modifications can be carried out by known techniques, including but not limited to specific chemical cleavage, acetylation, formylation, metabolic synthesis in the presence of tunicamycin, etc. Additionally, the analog or derivative may contain one or more unnatural amino acids. In some embodiments, antibodies may have modifications (e.g., substitutions, deletions or additions) in amino acid residues that interact with Fc receptors.

Examples of antibodies available for the treatment of cancer include, but are not limited to, humanized anti HER2 monoclonal antibody, HERCEPTIN® (trastuzumab; Genentech); RITUXAN® (rituximab; Genentech) which is a chimeric anti CD20 monoclonal antibody for the treatment of patients with non-Hodgkin's lymphoma; OvaRex (AltaRex Corporation, MA) which is a murine antibody for the treatment of ovarian cancer; Panorex (Glaxo Wellcome, NC) which is a murine IgG2a antibody for the treatment of colorectal cancer; Cetuximab Erbitux (Imclone Systems Inc., NY) which is an anti-EGFR IgG chimeric antibody for the treatment of epidermal growth factor positive cancers, such as head and neck cancer; Vitaxin (Medimmune, Inc., MD) which is a humanized antibody for the treatment of sarcoma; Campath I/H (Leukosite, MA) which is a humanized IgG1 antibody for the treatment of chronic lymphocytic leukemia (CLL); Smart MI95 (Protein Design Labs, Inc., CA) which is a humanized anti-CD33 IgG antibody for the treatment of acute myeloid leukemia (AML); LymphoCide (Immunomedics, Inc., NJ) which is a humanized anti-CD22 IgG antibody for the treatment of non-Hodgkin's lymphoma; Smart ID10 (Protein Design Labs, Inc., CA) which is a humanized anti-HLA-DR antibody for the treatment of non-Hodgkin's lymphoma; Oncolym (Techniclone, Inc., CA) which is a radiolabeled murine anti-HLA-Dr10 antibody for the treatment of non-Hodgkin's lymphoma; Allomune (BioTransplant, CA) which is a humanized anti-CD2 mAb for the treatment of Hodgkin's Disease or non-Hodgkin's lymphoma; Avastin (Genentech, Inc., CA) which is an anti-VEGF humanized antibody for the treatment of lung and colorectal cancers; Epratuzamab (Immunomedics, Inc., NJ and Amgen, CA) which is an anti-CD22 antibody for the treatment of non-Hodgkin's lymphoma; and CEAcide (Immunomedics, NJ) which is a humanized anti-CEA antibody for the treatment of colorectal cancer.

Other antibodies useful in the treatment of cancer include, but are not limited to, antibodies against the following antigens (exemplary cancers are indicated in parentheses): CA125 (ovarian), CA15-3 (carcinomas), CA19-9 (carcinomas), L6 (carcinomas), Lewis Y (carcinomas), Lewis X (carcinomas), alpha fetoprotein (carcinomas), CA 242 (colorectal), placental alkaline phosphatase (carcinomas), prostate specific membrane antigen (prostate), prostatic acid phosphatase (prostate), epidermal growth factor (carcinomas), MAGE-1 (carcinomas), MAGE-2 (carcinomas), MAGE-3 (carcinomas), MAGE-4 (carcinomas), anti-transferrin receptor (carcinomas), p97 (melanoma), MUC1-KLH (breast cancer), CEA (colorectal), gp100 (melanoma), MART1 (melanoma), prostate specific antigen (PSA) (prostate), IL-2 receptor (T-cell leukemia and lymphomas), CD20 (non-Hodgkin's lymphoma), CD52 (leukemia), CD33 (leukemia), CD22 (lymphoma), human chorionic gonadotropin (carcinoma), CD38 (multiple myeloma), CD40 (lymphoma), mucin (carcinomas), P21 (carcinomas), MPG (melanoma), and Neu oncogene product (carcinomas).

In some embodiments, the antibody is immunospecific for the treatment of an autoimmune disease such as, for example, anti-nuclear antibody; anti-ds DNA; anti-ss DNA, anti-cardiolipin antibody IgM, IgG; anti-phospholipid antibody IgM, IgG; anti-SM antibody; anti-mitochondrial antibody; thyroid antibody; microsomal antibody; thyroglobulin antibody; anti-SCL 70; anti-Jo; anti-U1 RNP; anti-La/SSB; anti-SSA; anti-SSB; anti-perital cells antibody; anti-histones; anti-RNP; C ANCA; P ANCA; anti centromere; anti fibrillarin, and anti-GBM antibody. In one embodiment, the antibody binds to an activated lymphocyte that is associated with an autoimmune disease.

In certain embodiments, the antibody may bind to a receptor or a receptor complex expressed on a target cell (e.g., an activated lymphocyte). The receptor or receptor complex may comprise an immunoglobulin gene superfamily member, a TNF receptor superfamily member, an integrin, a cytokine receptor, a chemokine receptor, a major histocompatibility protein, a lectin, or a complement control protein. Non-limiting examples of suitable immunoglobulin superfamily members are CD2, CD3, CD4, CD8, CD19, CD22, CD28, CD79, CD90, CD152/CTLA 4, PD 1, and ICOS. Non-limiting examples of suitable TNF receptor superfamily members are CD27, CD40, CD95/Fas, CD134/OX40, CD137/4 1BB, TNF R1, TNFR2, RANK, TACI, BCMA, osteoprotegerin, Apo2/TRAIL R1, TRAIL R2, TRAIL R3, TRAIL R4, and APO 3. Non-limiting examples of suitable integrins are CD11a, CD11b, CD11c, CD18, CD29, CD41, CD49a, CD49b, CD49c, CD49d, CD49e, CD49f, CD103, and CD104. Non-limiting examples of suitable lectins are C type, S type, and I type lectin.

The antibody also can be an antibody that is present on a target cell or target cell population. For example, transmembrane polypeptides and other markers may be specifically expressed on the surface of one or more particular type(s) of target cells (e.g., a cancer cell) as compared to on one or more normal cells (e.g., a non-cancerous cell(s)). Often, such markers are more abundantly expressed on the surface of the target cells, or exhibit greater immunogenicity, as compared to those on the surface of the normal cells. The identification of such cell surface antigen polypeptides has given rise to the ability to specifically target cells for destruction via antibody-based therapies. Thus, in some embodiments, the antibodies include, but are not limited to, antibodies against tumor-associated antigens (TAA).

The terms "drug unit" or "D" refer to any compound possessing a desired biological activity and a reactive functional group that may be used to incorporate the drug into the conjugate of the disclosure. In some embodiments, the drug unit indicate a cytotoxic drug useful in cancer therapy; a protein or polypeptide possessing a desired biological activity, such as a toxin, e.g., abrin, ricin A, *pseudomonas* exotoxin, and diphtheria toxin; other suitable proteins include tumor necrosis factor, α-interferon, β-interferon, nerve growth factor, platelet derived growth factor, tissue plasminogen activator, and biological response modifiers, for example, lymphokines, interleukin-1 (IL-1), interleukin-2 (IL-2), interleukin-6 (IL-6), granulocyte macrophage colony stimulating factor (GM-CSF), granulocyte colony stimulating factor (G-CSF), or other growth factors.

In one embodiment, the drug unit can be microtubule disrupting drugs such as auristatin, e.g. monomethyl auristatin E (MMAE), monomethyl auristatin F (MMAF), and auristatin F (AF). In another embodiment, the drug unit can be microtubule disrupting drugs such as maytansinoids, e.g. DM1, DM3, and DM4. In another embodiment, the drug unit can be DNA damaging agents such as calicheamicins, duocarmycins, SN-38, and pyrrolo[2,1-c][1,4]benzodiazepines (PBDs). Still in other embodiments, the drug unit can be amanitins, anthracyclines, baccatins, camptothecins, cemadotins, colchicines, colcimids, combretastatins, cryptophycins, discodermolides, docetaxel, doxorubicin, echinomycins, eleutherobins, epothilones, estramustines, lexitropsins, maytansines, methotrexate, netropsins, puromycins, rhizoxins, taxanes, tubulysins, or *vinca* alkaloids.

It should be noted that the drugs are not limited to above-mentioned categories and include all that could be used in ADCs.

The term "linker unit" described in the present disclosure includes a cleavable linker or a noncleavable linker. Cleavable linkers can be chemically labile and enzyme-labile linkers. Due to the high plasma stability and good intracellular cleaving selectivity and efficiency, enzyme-labile linkers are broadly selected as cleavable linker candidates in ADCs. In some embodiments, enzyme-labile linkers may include a peptide unit (-AAs-) selected from a group consisting of -valline-citruline- (-Val-Cit-), -valline-lysine- (-Val-Lys-), -valline-arginine- (-Val-Arg-), -phenylalanine-citruline- (-Phe-Cit-), -phenylalanine-lysine-(-Phe-Lys-), and -phenylalanine-arginine- (-Phe-Arg-). Typical enzyme-labile linkers include -Val-Cit- and -Phe-Lys-, which can be recognized by cathepsin B. In some embodiments, the noncleavable linker may be linkers that are capable of increasing the hydrophilicity of the resulting ADC. In one embodiment, the noncleavable linker may include one or more poly(ethylene glycol)(PEG). In other embodiment, the noncleavable linker may be PEG, PEG diamine ($NH_2$-PEG-$NH_2$), amine-PEG-hydroxyl ($NH_2$-PEG-OH), amine-PEG-COOH ($NH_2$-PEG-COOH), diethylene triamine, or a combination thereof. In some embodiments, PEG may be represented by

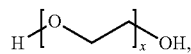

wherein x may be an integer ranging from 1 to 20.

The terms "conjugating linker" or "—C" described in the present disclosure refer to a novel conjugating linker structure used as a linker for conjugating to the antibody. A detail description of the conjugating linker will be described in the following paragraphs.

In one embodiment, the present disclosure provides a linker-drug represented by formula (I):

$$C\text{-}(L\text{-}D)_m \qquad (I)$$

In formula (I), C is a conjugating linker; L is a linker unit; D is a drug unit; and m is an integer ranging from 1 to 4. The conjugating linker (—C) is represented by formula (II):

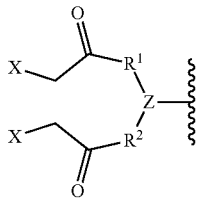

(II)

In formula (II), X is a leaving group. In some embodiments, leaving group (—X) may be —Cl, —Br, —I, —F, —OTs, —OMs, —OTf or —Obs. In formula (II), both of $R^1$ and $R^2$ are single bond or —NH—; Z is aryl, substituted aryl, heteroaryl, substituted heteroaryl, linear alkyl, cycloalkyl, heterocycloalkyl, or a combination thereof. The wave line of formula (II) indicates the covalent attachment site to L.

In formula (II), $R^1$ and $R^2$ attached to Z in ortho position, meta position, or para position to each other. Z is represented by formula (III):

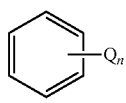

(III)

Q is a substitution group, comprising H, nitro, cyano, hydroxyl, alkoxy, amino, amide, ester, sulfamide, urea, linear alkyl, cycloalkyl, heterocycloalkyl, alkenyl, alkynyl, aryl, heteroaryl; n is an integer ranging from 0 to 3. In formula (III), one or more —CH— of benzene may not be substituted or may be substituted by N.

In some embodiments, the structure of the conjugating linker (—C) is represented by formula (IIa), formula (IIb), formula (IIc), or formula (IId):

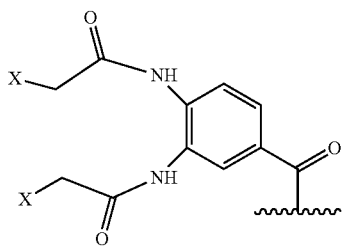

(IIa)

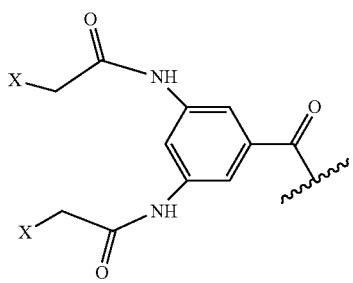

(IIb)

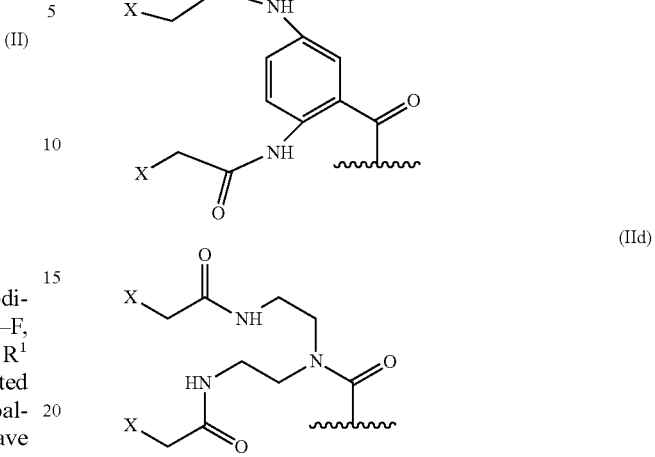

(IIc)

(IId)

However, it should be appreciated that the above structures are merely examples and the scope of the disclosure is not intended to be limited.

In some embodiments, the linker unit (-L) may include a cleavable linker or a noncleavable linker. In some embodiments, the cleavable linker may include a peptide unit (-AAs-) selected from a group consisting of -valline-citruline- (-Val-Cit-), -valline-lysine-(-Val-Lys-), -valline-arginine- (-Val-Arg-), -phenylalanine-citruline- (-Phe-Cit-), -phenylalanine-lysine-(-Phe-Lys-), and -phenylalanine-arginine- (-Phe-Arg-). In some embodiments, the peptide unit (-AAs-) can be enzymatically cleaved by one or more enzymes, for example, by a tumor-associated protease to liberate a drug unit (-D). In some embodiments, the noncleavable linker may be linkers that are capable of increasing the hydrophilicity of the resulting ADC. In one embodiment, the noncleavable linker may include one or more poly(ethylene glycol)(PEG). In other embodiment, the noncleavable linker may be PEG, PEG diamine ($NH_2$-PEG-$NH_2$), amine-PEG-hydroxyl ($NH_2$-PEG-OH), amine-PEG-COOH ($NH_2$-PEG-COOH), diethylene triamine, or a combination thereof. In some embodiments, PEG may be represented by

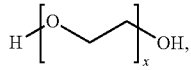

wherein x may be an integer ranging from 1 to 20.

In some embodiments, the drug unit (-D) further includes -proline- (-Pro-) as an attachment site to the linker unit (-L).

In formula (I), -(L-D) may be represented by formula (IIIa) or formula (IIIb):

$$L-D_o$$ (IIIa)

(IIIb)

L is linear alkyl, cycloalkyl, heterocycloalkyl, alkenyl, alkynyl, aryl, heteroaryl, poly(ethylene glycol) chain, or a combination thereof. Each of D is independently a cytotoxic drug, anti-autoimmune disease drug, or anti-inflammation drug; o is an integer ranging from 1 to 4; p is an integer ranging from 1 to 4; and q is an integer ranging from 1 to 4. When the -(L-D) is represented by formula (IIIb), the conjugating number of drugs are twice than that of -(L-D) represented by formula (IIIa). It should be realized that there may be other variations of -(L-D) according designs to provide -(L-D) with more conjugating number of drugs.

In some embodiments, the drug unit (-$D_o$) further includes -proline- (-Pro-) as an attachment site to the linker unit (-L). In some other embodiments, the drug unit ($D_p$) further includes -proline- (-Pro-) as an attachment site to L. In some other embodiments, the drug unit ($D_q$) further includes -proline- (-Pro-) as an attachment site to L.

In formula (I), the drug unit may include amanitins, anthracyclines, auristatins, baccatins, calicheamicins, camptothecins, cemadotins, colchicines, colcimids, combretastatins, cryptophycins, discodermolides, docetaxel, doxorubicin, duocarmycins, echinomycins, eleutherobins, epothilones, estramustines, lexitropsins, maytansines, maytansinoids, methotrexate, netropsins, pyrrolo[2,1-c][1,4] benzodi-azepines (PBDs), puromycins, rhizoxins, SN-38, taxanes, tubulysins, or *vinca* alkaloids.

In another embodiment, the present disclosure provides an antibody-drug conjugate (ADC) represented by formula (IV):

A-C'-(L-D)$_m$      (IV)

In formula (IV), A is a full-length antibody, an antibody fragment, a protein, or a polypeptide. C'-(L-D)$_m$ is a linker-drug, wherein C' is a conjugating linker; L is a linker unit; D is a drug unit; and m is an integer ranging from 1 to 4. A is conjugated to the linker-drug through two thiol groups respectively present in two cysteine residues of A.

In formula (IV), A-C' comprises the following structure represented by formula (V):

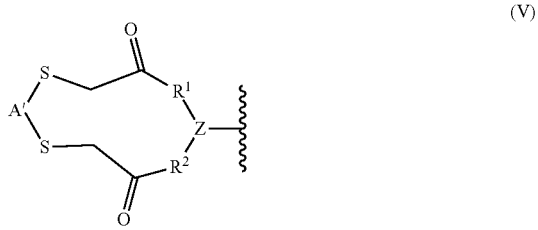

In formula (V), both of $R^1$ and $R^2$ are single bond or —NH—. Z is aryl, substituted aryl, heteroaryl, substituted heteroaryl, linear alkyl, cycloalkyl, heterocycloalkyl, or a combination thereof. The wave line of formula (V) indicates the covalent attachment site to L. A' indicates the remaining part of A which conjugated to the linker-drug through two thiol groups respectively present in two cysteine residues of A.

In formula (IV), "A" targets cell surface receptors or tumor-related antigens. In some embodiments, the antibody may be a chimeric antibody or a functionally active fragment thereof, a humanized antibody or a functionally active fragment thereof, a human antibody or a functionally active fragment thereof, a mouse antibody or a functionally active fragment thereof, a rat antibody or a functionally active fragment thereof, a goat antibody or a functionally active fragment thereof, or a rabbit antibody or a functionally active fragment thereof In some embodiments, the antibody is an IgG1 antibody or a functionally active fragment thereof, an IgG4 antibody or a functionally active fragment thereof.

In some embodiments, the antibody may include Herceptin, Erbitux, HLX-07, EG12014, anti-EpCAM Ab and IgG1, Rituximab, Ibritumomab tiuxetan, Tositumomab, Brentuximab vedotin, Alemtuzumab, IGN101, Adecatumumab, Labetuzumab, huA33, Pemtumomab, Oregovomab, CC49 (minretumomab), cG250, J591, MOv18, MORAb-003 (farletuzumab), 3F8, ch14.18, KW-2871, hu3S193, IgN311, Bevacizumab, IM-2C6, CDP791, Etaracizumab, Volociximab, Cetuximab, Panitumumab, Nimotuzumab, 806, Trastuzumab, Pertuzumab, MM-121, AMG 102, METMAB, SCH 900105, AVE1642, IMC-A12, MK-0646, R1507, CP 751871, KB004, IIIA4, Mapatumumab (HGS-ETR1), HGS-ETR2, CS-1008, Denosumab, Sibrotuzumab, F19, 8106, humanized anti HER2 mAb, OvaRex, Panorex, Cetuximab Erbitux, Vitaxin, Campath I/H, Smart MI95, LymphoCide, Smart ID10, Oncolym, Allomune, Avastin, Epratuzamab, or CEAcid.

In formula (V), $R^1$ and $R^2$ attach to Z in ortho position, meta position, or para position to each other. Z is represented by formula (III):

Q is a substitution group, comprising H, nitro, cyano, hydroxyl, alkoxy, amino, amide, ester, sulfamide, urea, linear alkyl, cycloalkyl, heterocycloalkyl, alkenyl, alkynyl, aryl, heteroaryl; n is an integer ranging from 0 to 3. In formula (III), one or more —CH— of benzene may not be substituted or may be substituted by N.

In formula (V), A-C' comprises the following structure represented by formula (Va), formula (Vb), formula (Vc), or formula (Vd):

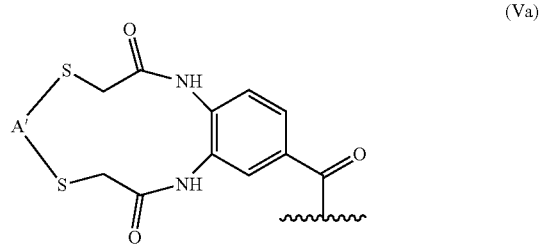

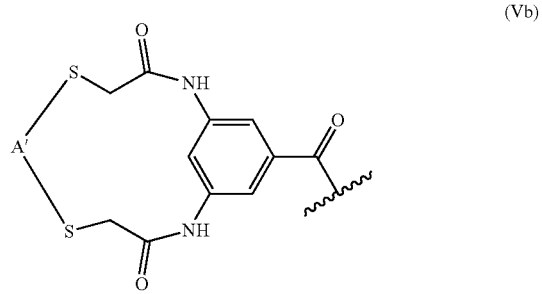

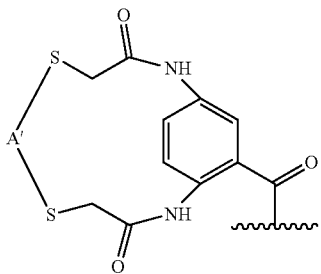

(Vc)

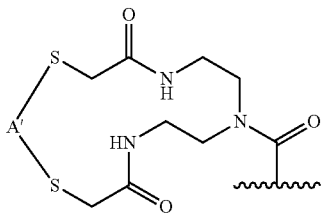

(Vd)

However, it should be appreciated that the above structures are merely examples and the scope of the disclosure is not intended to be limited.

In some embodiments, the linker unit (-L) may include a cleavable linker or a noncleavable linker. In some embodiments, the cleavable linker may include a peptide unit (-AAs-) selected from a group consisting of -valline-citruline- (-Val-Cit-), -valline-lysine-(-Val-Lys-), -valline-arginine- (-Val-Arg-), -phenylalanine-citruline- (-Phe-Cit-), -phenylalanine-lysine-(-Phe-Lys-), and -phenylalanine-arginine- (-Phe-Arg-). In some embodiments, the noncleavable linker may be linkers that are capable of increasing the hydrophilicity of the resulting ADC. In one embodiment, the noncleavable linker may include one or more poly(ethylene glycol)(PEG). In other embodiment, the noncleavable linker may be PEG, PEG diamine ($NH_2$-PEG-$NH_2$), amine-PEG-hydroxyl ($NH_2$-PEG-OH), amine-PEG-COOH ($NH_2$-PEG-COOH), diethylene triamine, or a combination thereof. In some embodiments, PEG may be represented by

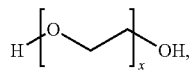

wherein x may be an integer ranging from 1 to 20. In some embodiments, the peptide unit (-AAs-) can be enzymatically cleaved by one or more enzymes, for example, by a tumor-associated protease to liberate a drug unit (-D).

In some embodiments, the drug unit (-D) further includes -proline- (-Pro-) as an attachment site to the linker unit (-L).

In formula (IV), -(L-D) may be represented by formula (IIIa) or formula (IIIb):

$$L\text{—}D_o \quad \text{(IIIa)}$$

(IIIb)

L is linear alkyl, cycloalkyl, heterocycloalkyl, alkenyl, alkynyl, aryl, heteroaryl, poly(ethylene glycol) chain, or a combination thereof. Each of D is independently a cytotoxic drug, anti-autoimmune disease drug, or anti-inflammation drug; o is an integer ranging from 1 to 4; p is an integer ranging from 1 to 4; and q is an integer ranging from 1 to 4. When the -(L-D) is represented by formula (IIIb), the conjugating number of drugs are twice than that of -(L-D) represented by formula (IIIa). It should be realized that there may be other variations of -(L-D) according designs to provide -(L-D) with more conjugating number of drugs.

In some embodiments, the drug unit ($-D_o$) further includes -proline- (-Pro-) as an attachment site to the linker unit (-L). In some other embodiments, the drug unit ($D_p$) further includes -proline- (-Pro-) as an attachment site to L. In some other embodiments, the drug unit ($D_q$) further includes -proline- (-Pro-) as an attachment site to L.

In some embodiments, the drug unit may include amanitins, anthracyclines, auristatins, baccatins, calicheamicins, camptothecins, cemadotins, colchicines, colcimids, combretastatins, cryptophycins, discodermolides, docetaxel, doxorubicin, duocarmycins, echinomycins, eleutherobins, epothilones, estramustines, lexitropsins, maytansines, maytansinoids, methotrexate, netropsins, pyrrolo[2,1-c][1,4]benzodi-azepines (PBDs), puromycins, rhizoxins, SN-38, taxanes, tubulysins, or vinca alkaloids.

Theoretically, the DAR value corresponds to the number of free thiols provided in the reduced antibody after the reduction. For example, after the four inter-chain disulfide bonds in antibody are converted to 8 free thiols, the site-specific conjugating linker can specifically conjugate to the 8 free thiol groups present in cysteine residues of antigen. Thus, the antibody-drug conjugates (ADCs) obtained from the novel conjugating linker structure provided by the present disclosure have a DAR (drug to antibody) about 4 while the linker unit (-L) conjugates to 1 drug unit (-D). In another embodiment, the antibody-drug conjugates (ADCs) obtained from the novel conjugating linker structure provided by the present disclosure have a DAR (drug to antibody) about 8 while the linker unit (-L) conjugates to 2 drug units (-D).

The Examples and Comparative Examples are described below to illustrate the methods for forming the linker-toxins and antibody-drug conjugates, and the properties of the antibody-drug conjugates.

EXAMPLES AND COMPARATIVE EXAMPLES

The disclosure will be described in detail by the following examples. Among them, MMAE and AF were purchased from Concortis Biotherapeutics. The structure of the above compounds is well known by those skilled in the art, and is not described herein for simplicity.

The abbreviations used in linker-drugs and their corresponding chemical structures are listed in Table 1.

TABLE 1

| linker-drug | structure | required MW |
|---|---|---|
| 1 | 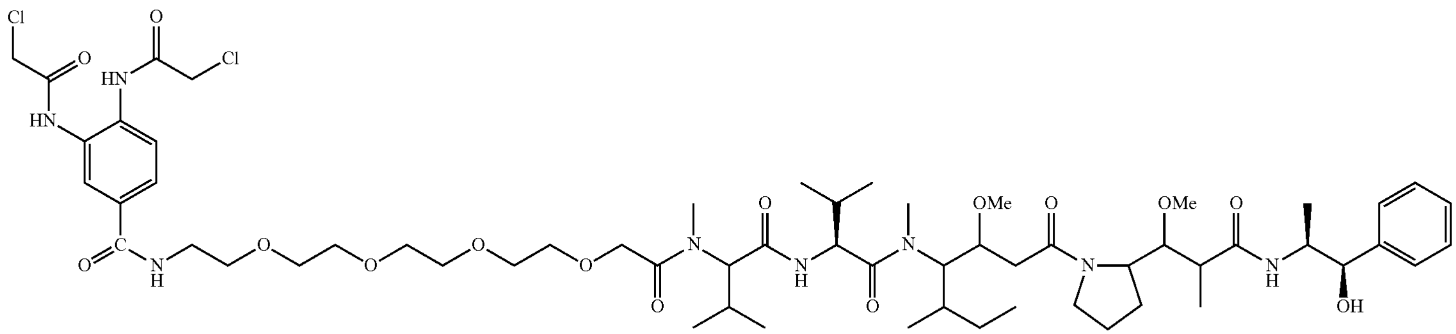 [SMILES: CCC(C)C(C(CC(=O)N1CCCC1C(OC)C(C)C(=O)N[C@@H](C)[C@H](O)c1ccccc1)OC)N(C)C(=O)[C@@H](NC(=O)C(C(C)C)N(C)C(=O)COCCOCCOCCOCCNC(=O)c1ccc(NC(=O)CCl)c(NC(=O)CCl)c1)C(C)C] | 1236.6 |
| 2 | 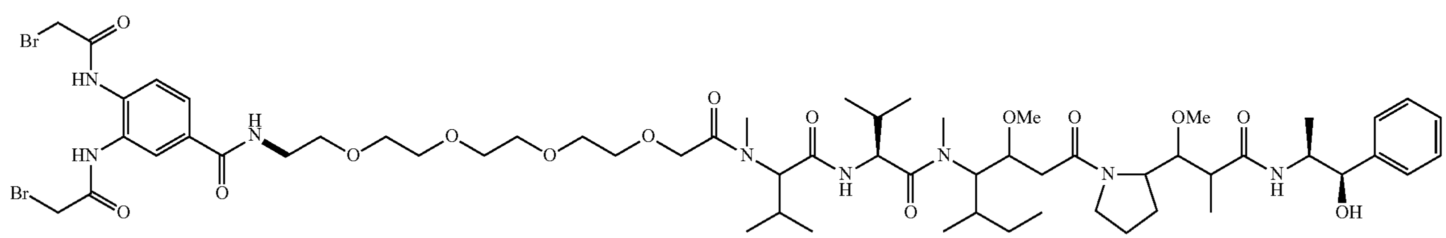 | 1324.5 |
| 3 | 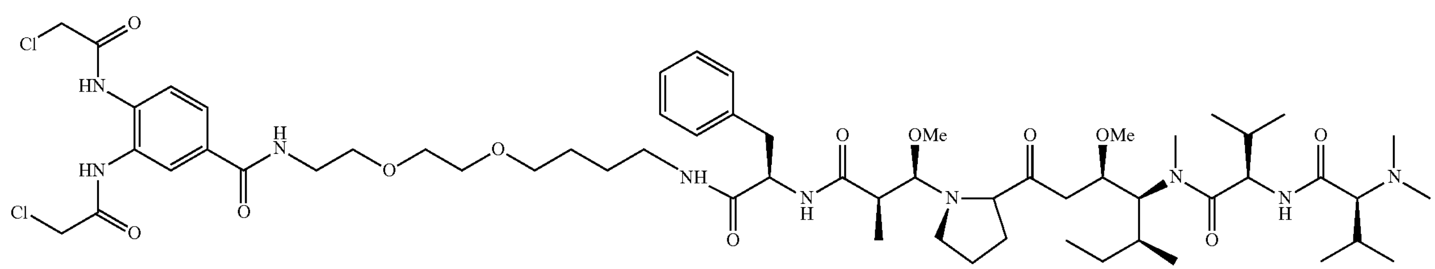 | 1161.6 |

TABLE 1-continued
| linker-drug | structure | required MW |
|---|---|---|
| 4 | 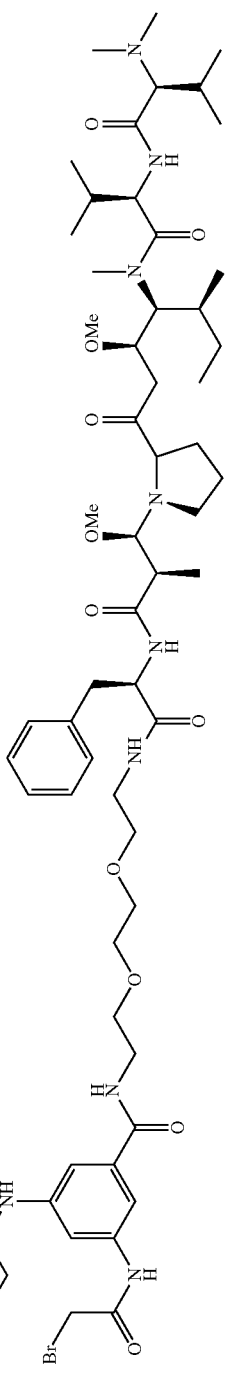 | 1249.4 |
| 5 | 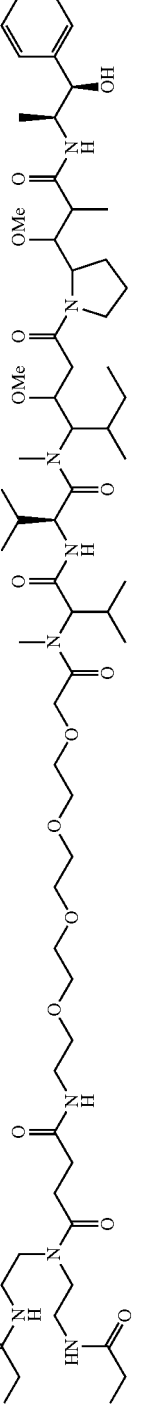 | 1378.3 |
| 6 | 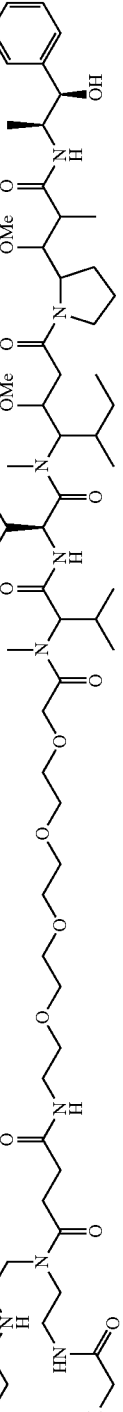 | 1471.5 |

TABLE 1-continued
| linker-drug | structure | required MW |
|---|---|---|
| 7 | 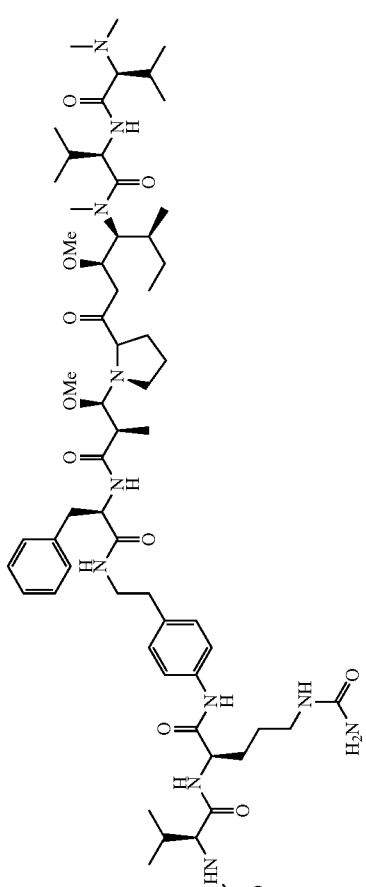 | 1640.83 |
| 8 | 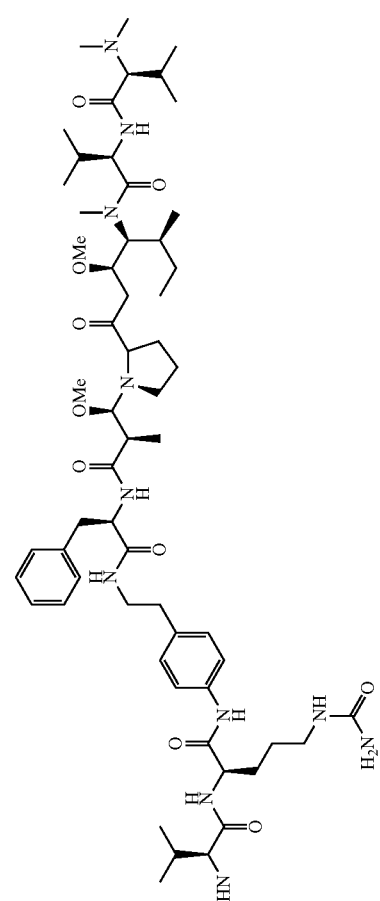 | 1726.7 |

TABLE 1-continued
| linker-drug | structure | required MW |
|---|---|---|
| 9 | 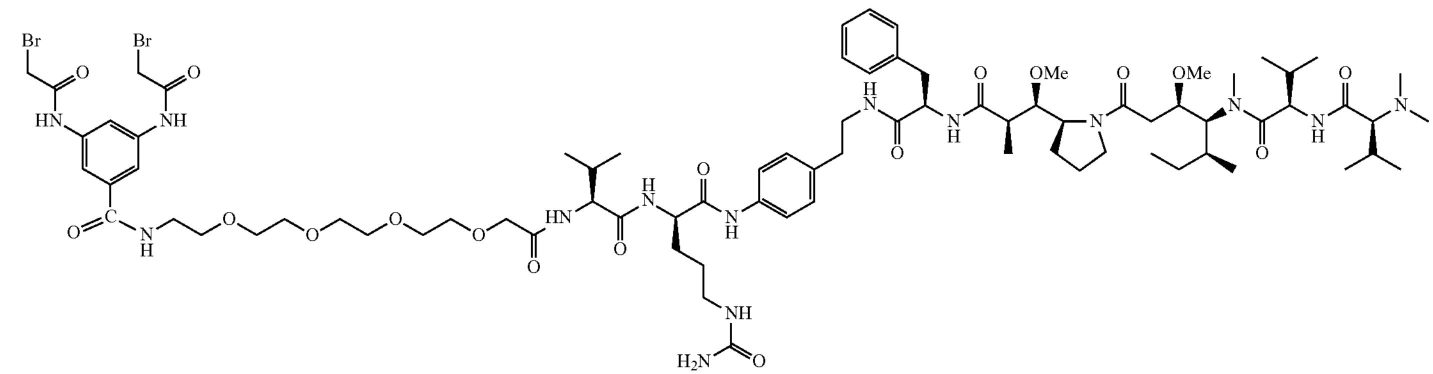 [SMILES: CC[C@H](C)[C@@H]([C@@H](CC(=O)N1CCC[C@H]1[C@H](OC)[C@@H](C)C(=O)N[C@H](Cc1ccccc1)C(=O)NCCc1ccc(NC(=O)[C@@H](CCCNC(N)=O)NC(=O)[C@@H](NC(=O)COCCOCCOCCOCCNC(=O)c2cc(NC(=O)CBr)cc(NC(=O)CBr)c2)C(C)C)cc1)OC)N(C)C(=O)[C@H](NC(=O)[C@H](C(C)C)N(C)C)C(C)C] | 1726.7 |
| 10 | 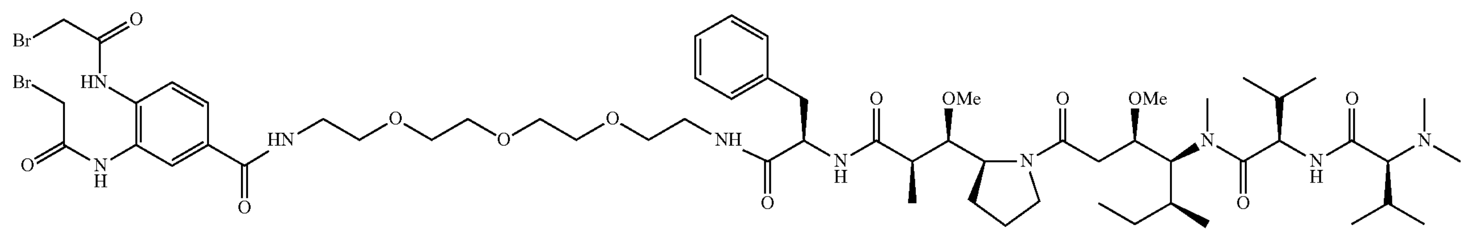 [SMILES: CC[C@H](C)[C@@H]([C@@H](CC(=O)N1CCC[C@H]1[C@H](OC)[C@@H](C)C(=O)N[C@H](Cc1ccccc1)C(=O)NCCOCCOCCOCCNC(=O)c1ccc(NC(=O)CBr)c(NC(=O)CBr)c1)OC)N(C)C(=O)[C@H](NC(=O)[C@H](C(C)C)N(C)C)C(C)C] | 1296.23 |
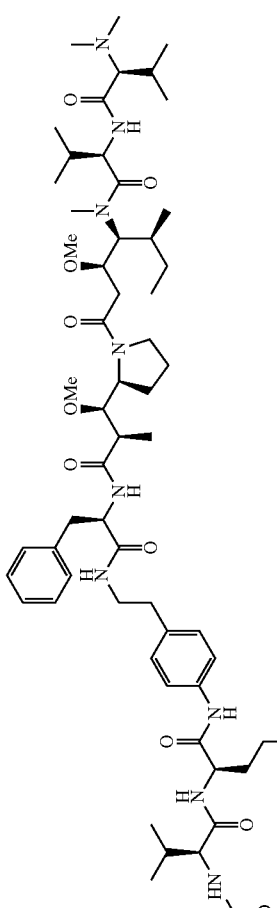
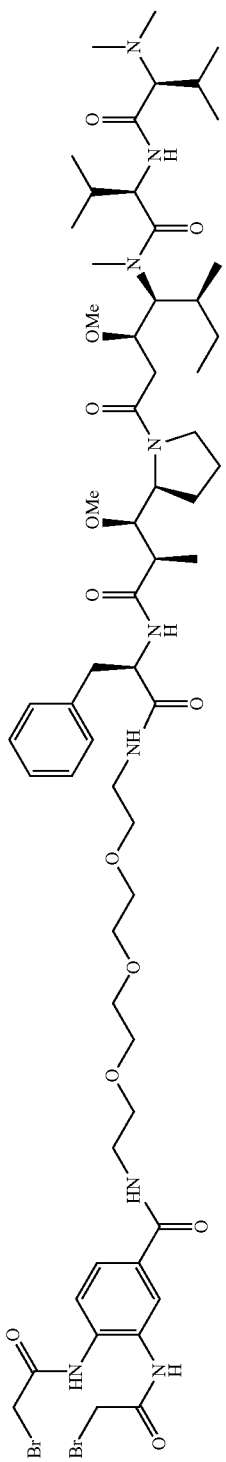

TABLE 1-continued
| linker-drug | structure | required MW |
|---|---|---|
| 11 | 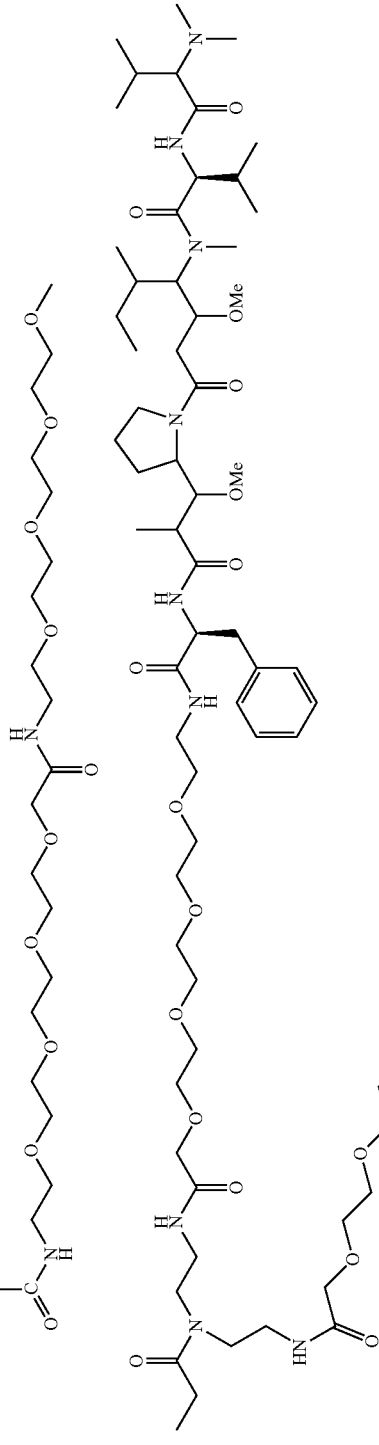 | 2868.16 |

TABLE 1-continued
| linker-drug | structure | required MW |
|---|---|---|
| 12 | 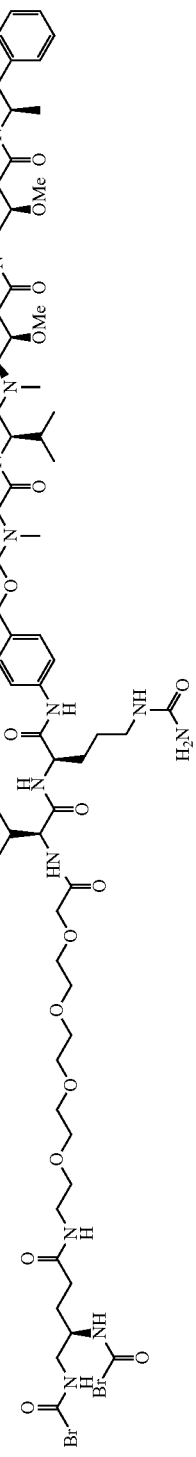 | 1681.72 |
| 13 | 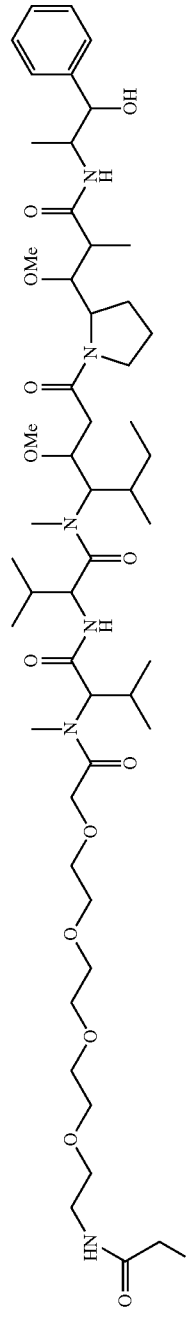 | 1323.25 |
| L1 | 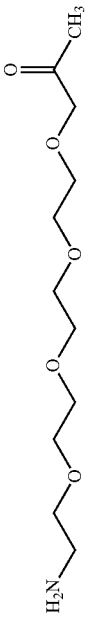 | 251.1 |
| CJ24-1 | 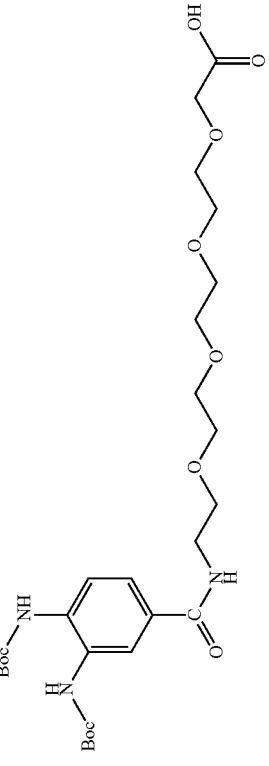 | 585.28 |

TABLE 1-continued
| linker-drug | structure | required MW |
|---|---|---|
| CJ35-5 | 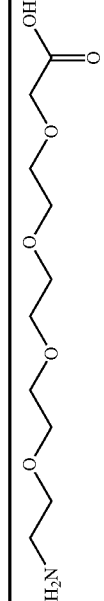 | 251.14 |
| P | 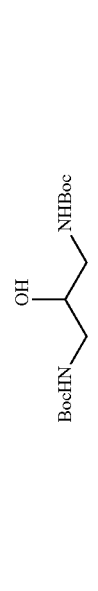 | 290.18 |
| Pro-line-AF | 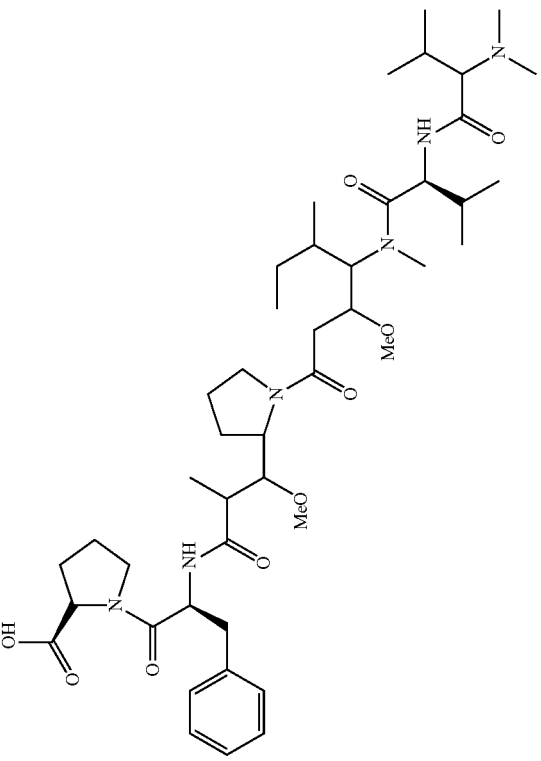 | 842.55 |

Example 1: Preparation of Linker-Drug 1

Step 1: Synthesis of Compound 1a

Linker-drug 1 was synthesized according to the procedures shown in the following scheme.

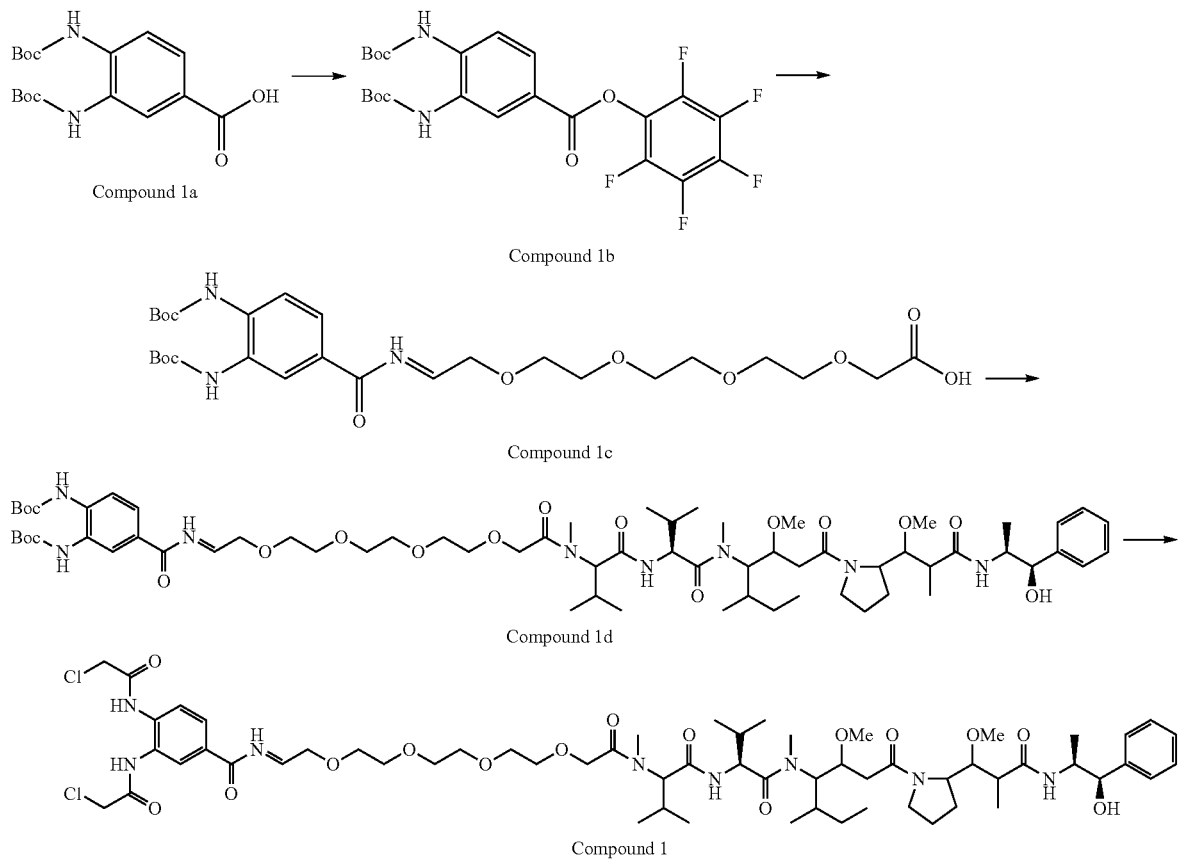

The synthesis of Compound 1a was performed as described in the patent literature U.S. Pat. No. 9,086,416B2. 3,4-diaminobenzoic acid (1.52 g, 10 mmol) and di-tert-butoxy dicarbonate (t-Boc)$_2$O; 6.55 g, 30 mmol) with triethylamine (NEt$_3$; 7.0 mL, 60 mmol) in CH$_2$Cl$_2$ (200 mL) were stirred at room temperature (25° C.) for overnight (24 hours). The resulting solution was extracted with water, dried with Na$_2$SO$_4$ to give Compound 1a (N-Boc-3,4-diaminobenzoic acid) (1.37 g, yield 54%) as a brown powder.

Chemical formula of Compound 1a: $C_{17}H_{24}N_2O_6$. $^1$H NMR (500 MHz, CDCl$_3$) δ 8.04 (s, 1H, ArH), 7.91-7.89 (dd, 2H, ArH), 7.23 (s, 1H), 6.60 (brs, 2H, NH), 1.54 (s, 18H, CH3). M/Z (ES+): 354.0 (M+H)$^+$, 376.0 (M+Na).

Step 2: Synthesis of Compound 1b

To a mixture solution of Compound 1a (60 mg, 0.17 mmole) and pentafluorophenol (38 mg; 0.20 mmole) in DCM (6 mL) was added DCC (42 mg, 0.20 mmole). The mixture was stirred at room temperature for 12 hours, the precipitate was filtered and concentrated in vacuo. The column was eluted with n-Hexane/EtOAc (4:1). The fractions containing the target compound were collected and concentrated under reduced pressure to produce Compound 1b (76 mg, 0.14 mmole, yield 80%).

Chemical formula of Compound 1b: $C_{23}H_{23}F_5N_2O_6$. $^1$H-NMR (500 MHz; CDCl$_3$) d: 8.12 (s; 1H); 7.97 (s; 2H), 7.25 (s; 1H), 1.5 (s, 18H), MS (ESI, negative ion): M/Z: 517.9 (M$^-$).

Step 3: Synthesis of Compound 1c

To a solution of Compound 1b (11.6 mg, 0.22 mmole) in DCM (1 mL) and DMF (2 mL), L1 (55 mg, 0.33 mmole), DIPEA (47.4 mg, 0.55 mmole) were added. The reaction was left for 1 hour at room temperature. After the removal of solvent, Compound 1c was purified by preparative HPLC (50% CH$_3$CN in H$_2$O+0.1% TFA; UV 210 nm; Inertsil ODS-3 column 30×250 mm; flow rate 32 mL/min; Compound 1c RT, 14.6 min). Compound 1c was obtained as a white solid (48 mg; yield 57%).

Chemical formula of Compound 1c: $C_{27}H_{44}N_3O_{11}$. ESI-HIMS (positive ion), M/Z: 586.2972, [M+H]$^+$ for $C_{27}H_{44}N_3O_{11}$, err: −0.3 ppm.

Step 4: Synthesis of Compound 1d

To a solution of Compound 1b (28 mg, 0.04 mmole) in 4 mL co-solvent DCM/DMF (1:1) and MMAE (60 mg, 0.07 mmole) in 2 mL DMF, TBTU (44 m) and DIPEA (36 mg) were added. The reaction was gone completion after 4 hours. Solvent was removed under a reduced pressure. Inertsil ODS-3 column 30×250 mm; flow rate 32 mL/min; Compound 1d RT, 17 min). Compound 1d was obtained as a white solid (42 mg; yield 70%).

Chemical formula of Compound 1d: $C_{66}H_{108}N_8O_{17}$. (ESI, positive ion): M/Z: 1286.9, (M+1); 1308.8 (M+Na).

Step 5: Synthesis of Linker-Drug 1

To a solution Compound 1d 62 mg (0.048 mmole) in 2 mL DCM at 25-27° C. were added dropwise trifloroacetic acid 1 mL (11.5 mmole). The water bath was removed and stirring was continued for 4 hours. The solvent was removed under reduced pressure, the residue was added 5 mL methanol and slurried for 5 minutes, then solvent was removed. A minimum of DIW (1.5 mL) was added and lyophilized to give the crude product Compound 1d-deBoc 49 mg as TFA salt.

Next, to a solution of the TFA salt (49 mg, 0.048 mmole) in DCM (1.5 mL) solution were added, with stirring at 0-5° C., trimethylamine (45 µL, 0.613 mmole), followed by a solution of chloroacetyl chloride 43 mg (0.377 mmole) in DCM (0.3 mL). After stirring, second portion of trimethylamine (45 µl, 0.613 mmole) was added. The cooling bath was removed after 2 hours and stirring was continued for 15 hours. The reaction was checked for completion by HPLC and the mixture was evaporated to dryness. Purification by RP-HPLC (the residue was diluted by 3 mL M.P. solvent, Inertsil ODS-3 column 30×250 mm, 10 µm; flow rate 31 mL/min, M.P. 43% gradient to 55% AcN/H₂O with 0.1% TFA, UV220 nm). The product-containing fraction (Rt 16.1 min) were lyophilized to give Compound 1, i.e. Linker-drug 1 43 mg, 68.3% yield.

Chemical formula of Linker-drug 1: $C_{80}H_{94}Cl_2N_8O_5$. (ESI, positive ion): M/Z: $[M+H]^+=1238.7$, $[M+Na]+=1260.7$.

Example 2: Preparation of Linker-Drug 2

Linker-drug 2 was synthesized according to the procedures shown in the following scheme.

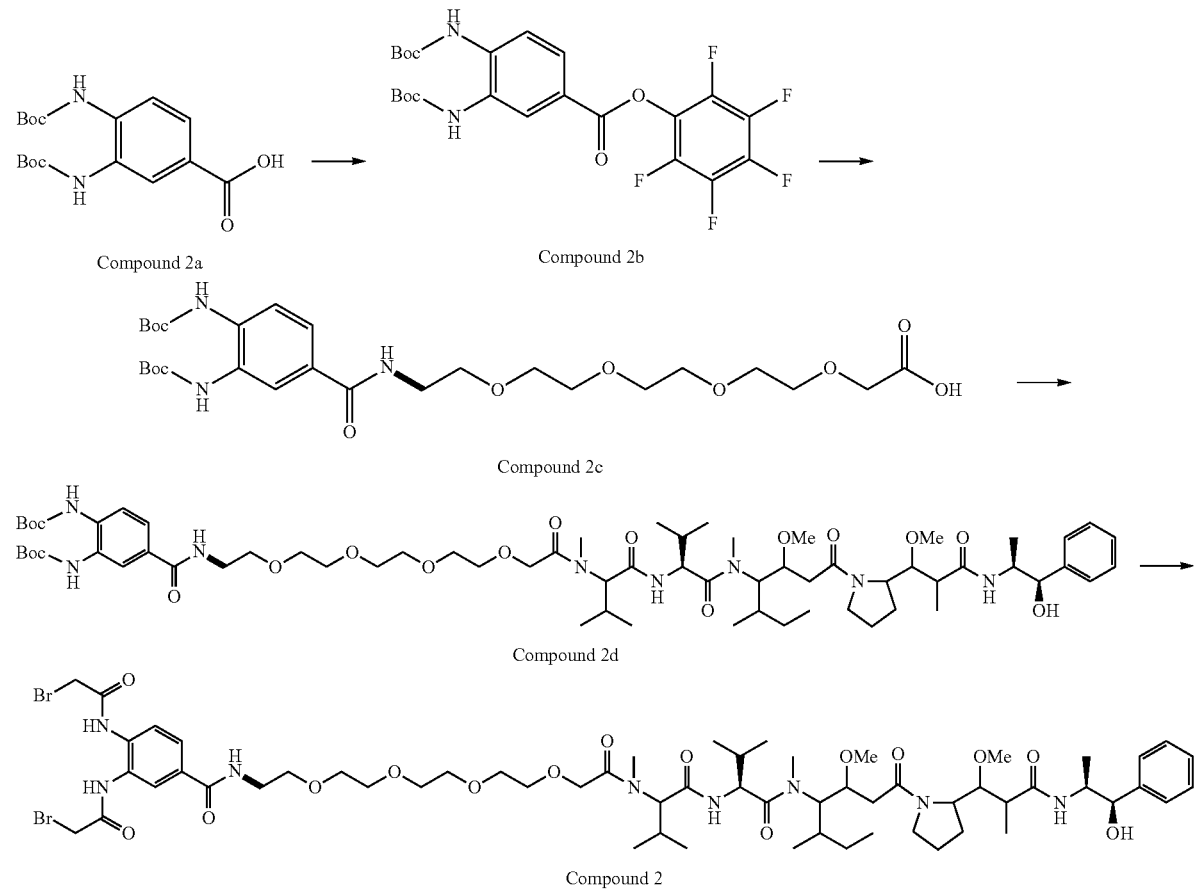

Compound 2a

Compound 2b

Compound 2c

Compound 2d

Compound 2

Steps 1-4: Synthesis of Compounds 2a, 2b, 2c, 2d

Compounds 2a, 2b, 2c, and 2d were synthesized by the same synthetic procedure as steps 1-4 described in Example 1.

Step 5: Synthesis of Linker-Drug 2

To a solution Compound 2d 40 mg (0.031 mmole) in 1 mL DCM at 20-23° C. water bath was added dropwise trifloroacetic acid 0.8 mL (9.12 mmole). The water bath was removed and stirring was continued for 2 hours. The solvent was removed under reduced pressure, the residue was added 2 mL methanol and slurried for 5 minutes, and then, the solvent was removed. A minimum of DIW (2 mL) was added and lyophilized to give the crude product Compound 2d-deBoc 27 mg as TFA salt.

Next, to a solution of the TFA salt (27 mg, 0.031 mmole) in DCM (1 mL) solution were added, with stirring at 0-5° C., trimethylamine (20 µL, 0.136 mmole) in DCM (0.3 mL), followed by a solution of bromoacetyl bromide 42 mg (0.208 mmole) in DCM (0.3 mL). The cooling bath was removed after 2 hours and stirring was continued for 15 hours. The reaction was checked for completion by HPLC and the mixture was evaporated to dryness. Purification by RP-HPLC (the residue was diluted by 4 mL M.P. solvent, Inertsil ODS-3 column 30×250 mm, 10 µm; flow rate 31 mL/min, M.P. from 43% gradient to 62% AcN/H$_2$O with 0.1% TFA, UV220 nm) and the product-containing fraction (Rt=17-19 min) were lyophilized to give Compound 2, i.e. Linker-drug 2 2.6 mg, yield 6.8%.

Chemical formula of Linker-drug 2: $C_{60}H_{84}Br_2N_8O_{15}$. (ESI, positive ion): M/Z: [M+H]$^+$=1326.8.

Example 3: Preparation of Linker-Drug 3

Linker-drug 3 was synthesized according to the procedures shown in the following scheme.

diamine (0.6 g, 75.6%). 1H NMR (500 MHz, CDCl3): δ 3.61 (s, 4H), 3.55-3.53 (t, 2H), 3.52-3.49 (t, 2H), 3.31-3.30 (t, 2H), 2.88-2.85 (t, 2H), 1.43 (s, 9H).

Step 2: Synthesis of Compound 3b (Boc-PEG-AF)

To a solution of Auristatin F (200 mg, 0.23 mmole) in DCM (2 mL) and DMF (2 mL), Compound 3a (75 mg, 0.30 mmole), DIPEA (180 mg, 1.39 mmole), TBTU (220 mg, 0.68 mmole) were added. The reaction was left for one hour at 24 hr at RT. After the removal of solvent, Compound 3b was purified by preparative HPLC (Inertsil ODS-3 column 30×250 mm; mobile phase 43% AcN/H$_2$O with 0.1% TFA, flow rate 32 mL/min; Boc-PEG-AF RT 9.3 min). The entitled Compound 3b was obtained as a white solid (203 mg; 89%). ESI, positive ion: M/Z: 977.5 (M+1); 993.2 (M+Na).

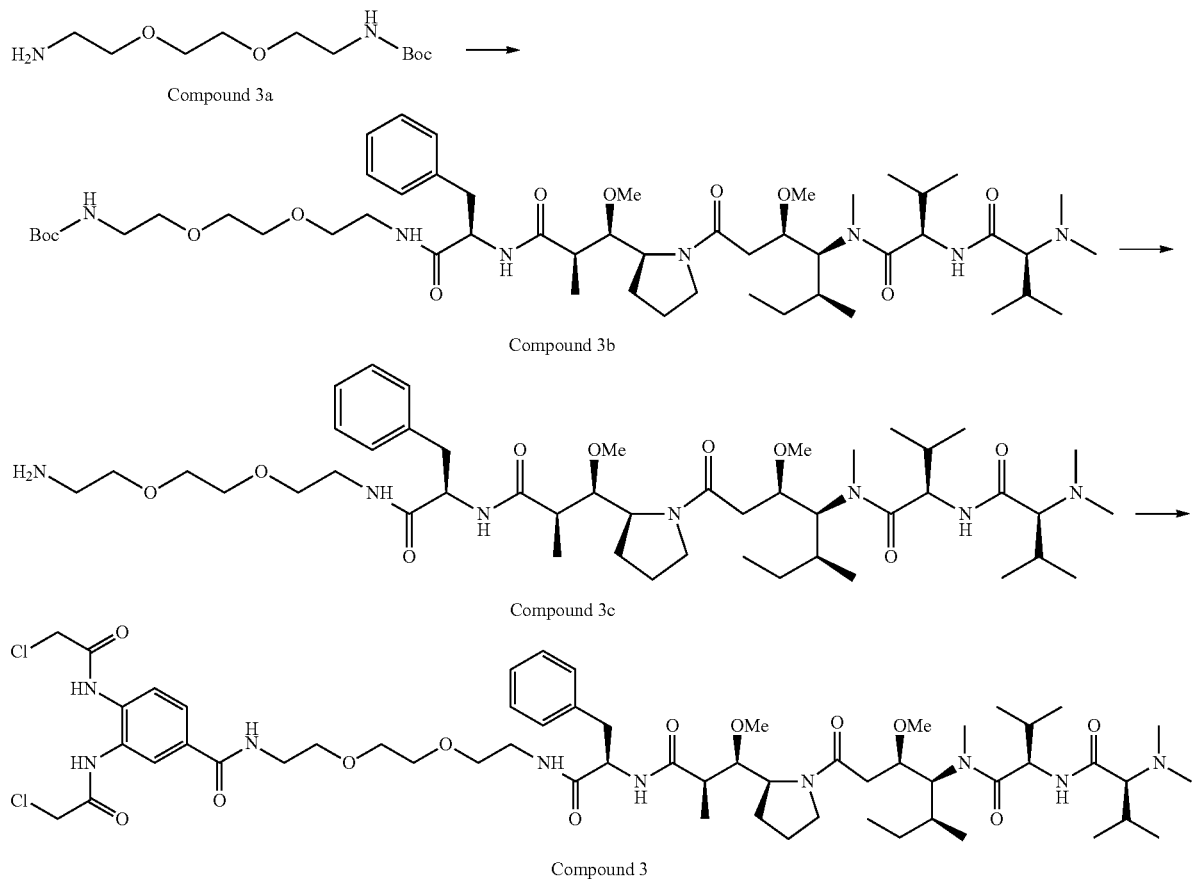

Compound 3a

Compound 3b

Compound 3c

Compound 3

Step 1: Synthesis of Compound 3a
(N-Boc-3,6-dioxaoctane-1,8-diamine)

The compound DAB-2 was prepared according to literature method (Bioorganic and a solution of di-tert-butyl dicarbonate ((Boc)$_2$O) (0.7 g, 3.21 mmol) in CH$_2$Cl$_2$ (10 mL) was added dropwise to a mixture of tris(ethylene glycol)-1,8-diamine (5.0 g, 278 mmol) and diisopropylethylamine (10 mL, 57 mmol) at room temperature over a period of 2 hours. The reaction mixture was stirred for 6 hours, after which it was concentrated in vacuo. Purification by flash silica gel column chromatography (CH$_2$Cl$_2$/CH$_3$OH, 10/1, v/v) afforded N-Boc-3,6-dioxaoctane-1,8-

Step 3: Synthesis of Compound 3c

To a solution of Compound 3b (203 mg, 0.21 mmol) in DCM (4 mL) was added TFA (2 mL). The reaction mixture was stirred for 1 hr at RT, after which time the solvents were removed in vacuo. The crude product was used without further purification. ESI, positive ion: M/Z: 877.4 (M+1); 899.4 (M+Na).

Step 4: Synthesis of Compound 3

To a solution of Compound 3c (180 mg, 0.20 mmole) in 4 mL co-solvent DCM/DMF (1:1) and compound 3,4-bis (2-chloroacetamido)benzoic acid (62 mg, 0.20 mmole) in 2 mL DMF, TBTU (191 mg) and DIPEA (154 mg) were added. The reaction was gone completion after 4 hours. Solvent was removed under a reduced pressure. Purification by RP-HPLC (Inertsil ODS-3 column 30×250 mm; flow rate 32 mL/min; Compound 3 RT 17 min) and the entitled Compound 3, i.e. Linker-drug 3 was obtained as a white solid (167 mg; 70%).

Chemical formula of Linker-drug 3: $C_{57}H_{89}Cl_2N_9O_{12}$. ESI, positive ion: M/Z: 1163.5 (M+1); 1185.3 (M+Na). ESI-HIMS, positive ion: M/Z: 1162.6082, [M+H]+ for $C_{57}H_{90}C_{12}N_9O_{12}$, err: −0.1 ppm.

Example 4: Preparation of Linker-Drug 4

Linker-drug 4 was synthesized according to the procedures shown in the following scheme.

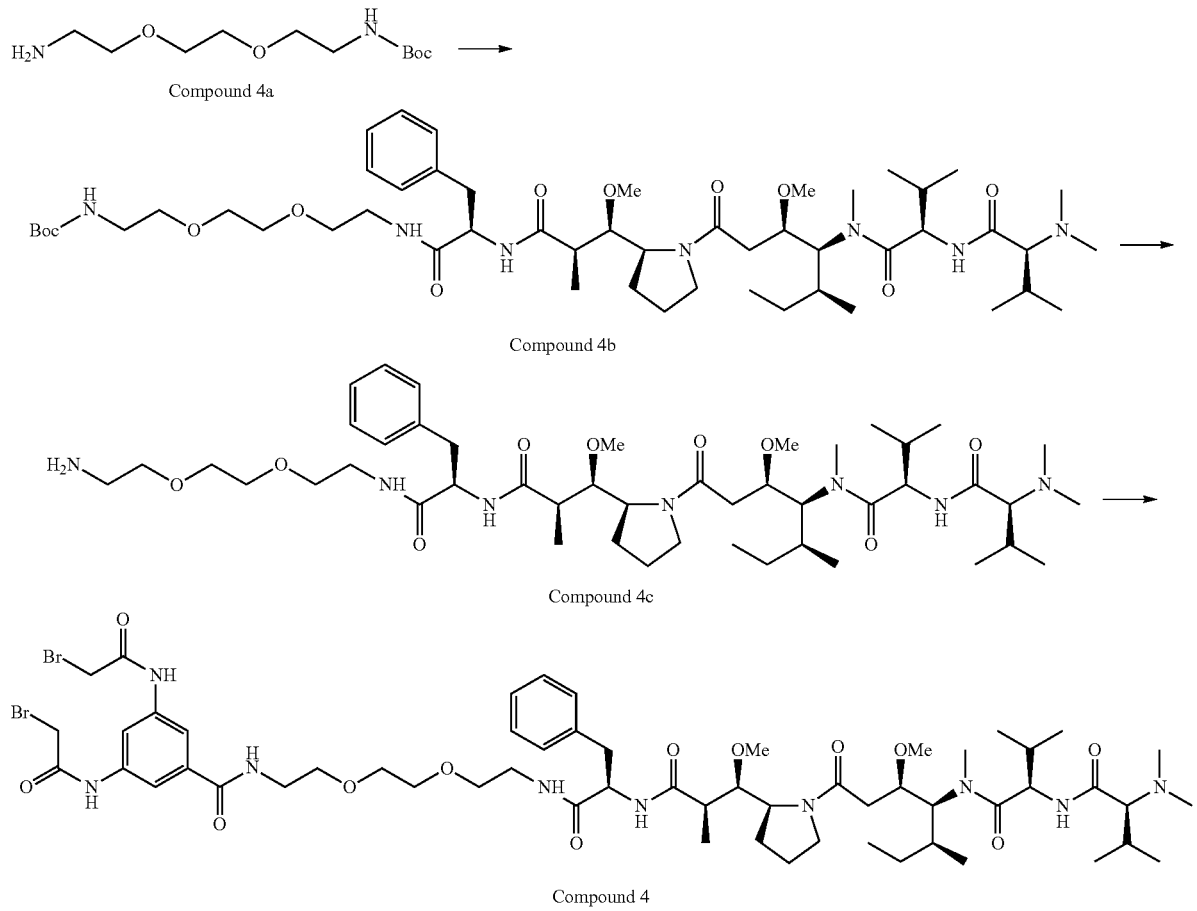

Steps 1-3: Synthesis of Compounds 4a, 4b, 4c

Compounds 4a, 4b, and 4c were synthesized by the same synthetic procedure as steps 1-3 described in Example 3.

Step 4: Synthesis of Linker-Drug 4

To a solution of Compound 4b 90 mg (0.074 mmole) in 4 mL DCM at 20-23° C. water bath were added dropwise trifloroacetic acid 2 mL (10.4 mmole). The water bath was removed and stirring was continued for 2 hours. The solvent was removed under reduced pressure, the residue was added 2 mL methanol and slurried for 5 mins then solvent was removed. A minimum of DIW (2 mL) was added and lyophilized to give the crude product of Compound 4c 90 mg as TFA salt.

To a solution of the TFA salt (90 mg, 0.074 mmole) in DCM (1.5 mL) solution were added, with stirring at 0-5° C., trimethylamine (26 μL, 0.18 mmole), followed by a solution of bromoacetyl bromide 64 mg (0.31 mmole) in DCM (0.3 mL). After 5 mins stirring, second portion of trimethylamine (52 μL, 0.36 mmole) was added. The cooling bath was removed after 2 hours and stirring was continued for 15 hours. The reaction was checked for completion by HPLC and the mixture was evaporated to dryness. Purification by RP-HPLC (the residue was diluted by 3 mL M.P. solvent, Inertsil ODS-3 column 30×250 mm, 10 um; flow rate 31 mL/min, M.P. 43% AcN/H₂O with 0.1% TFA, UV 220 nm) and the product-containing fraction (Rt=7.66 min) were lyophilized to give the Compound 4, i.e. Linker-drug 4 85 mg, 92% yield.

Chemical formula of Linker drug 4: $C_{57}H_{89}Br_2N_9O_{12}$. (ESI, positive ion): M/Z: M+H=1251.6.

Example 5: Preparation of Linker-Drug 5

Linker-drug 5 was synthesized according to the procedures shown in the following scheme.

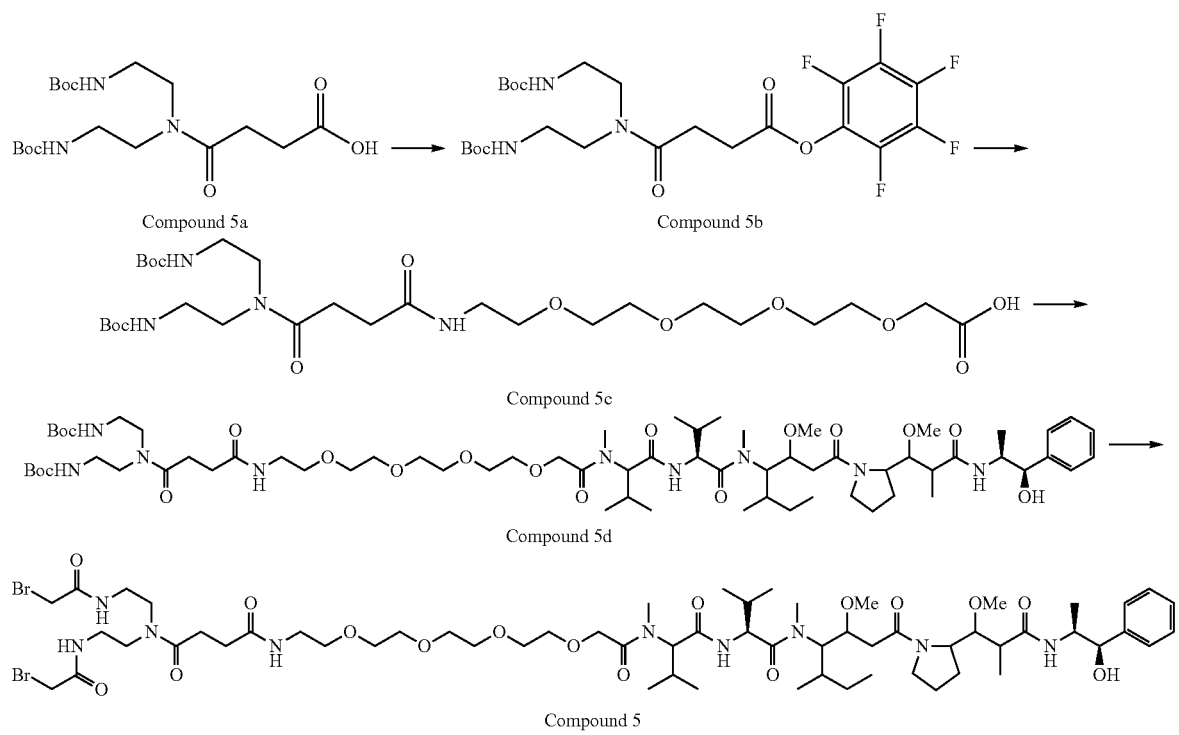

Compound 5

Step 1: Synthesis of Compound 5a

Compound 5a is also referred as di-tert-butyl (iminodiethane-2,1-diyl) biscarbamate (DETA-3). Compound 5a was prepared according to literature method (Org. Lett. 2000, 2, 2117-2120).

First, DETA-2 was synthesized according to the following method. Diethylene triamine (0.82 g, 6.2 mmol) and triethylamine (2.6 mL, 8.6 mmol, 3 eq.) were dissolved in tetrahydrofuran (40 mL) and cooled in ice-bath. A solution of $Boc_2O$ (3.1 g, 12.4 mmol, 2 eq.) in tetrahydrofuran (20 mL) was then added dropwise over 2.5 h. The reaction mixture was stirred at 0° C. for an additional 1 h, before it was allowed to reach ambient temperature overnight. The reaction mixture was then concentrated in vacuo. The residue was dissolved in dichloromethane and washed with 1 M aq. NaOH. The organic phase was dried over $Na_2SO_4$ and concentrated in vacuo. The crude material was purified by flash chromatography, giving a mixture of di-tert-butyl (iminodiethane-2,-diyl)biscarbamate (DETA-2, M/Z (ES−), 302.9 (M−H)−.) and DETA-2-1 (M/Z (ES−), 403.0 (M−H)− as a yellow viscous oil. To a solution of compound DETA-2 and DETA-2-1 (0.86 g) in DCM (20 mL) was added succinic anhydride (0.3 g, 3 mmol). The reaction mixture was stirred at room temperature for 16 h. Solvent was removed in vacuo, and the residue was purified by column chromatography (silica gel, DCM/MeOH 20/1) to afford a white solid (0.43 g). 1H NMR (500 MHz, $CDCl_3$) δ 5.21 (br, 1H), 4.98 (br, 1H), 3.32 (br, 6H), 3.24 (bs, 6H), 1.45 (s, 9H, $CH_3$), 1.46 (s, 9H, $CH_3$), 1.42 (s, 9H, $CH_3$); M/Z (ES+), 404.9 (M+H), 426.7 (M+Na).

Next, to a solution of compound DETA-2 (0.86 g, 2.84 mmol) in DCM (20 mL) was added succinic anhydride (0.3 g, 3 mmol). The reaction mixture was stirred at room temperature for 16 h. Solvent was removed in vacuo, and the residue was purified by column chromatography (silica gel, DCM/MeOH 20/1) to give the Compound 5a as a white solid (0.43 g). 1H NMR (500 MHz, $CDCl_3$) δ 5.21 (br, 1H), 4.98 (br, 1H), 3.68-3.71 (m, 4H), 3.46-3.48 (m, 4H), 2.62-2.69 (m, 4H), 1.45 (s, 18H, $CH_3$) MS: (EST') M/Z, 404.9 $(M+H)^+$. 426.2 (M+Na).

Step 2: Synthesis of Compound 5b

To a mixture solution of Compound 5a (170 mg, 0.42 mmole) and pentafluorophenol (93 mg; 0.50 mmol) in DCM (6 mL) was added DCC (104 mg, 0.50 mmole). The mixture was stirred at room temperature for 12 hours, the precipitate was filtered and concentrated in vacuo. The column was eluted with n-Hexane/EtOAc (4:1). The fractions containing the target compound were collected and concentrated under reduced pressure to produce Compound 5b (168 mg, 0.29 mmole, yield 70%); MS (ESI, negative ion): M/Z: 570.9 $(M+1)^+$, 592.8 (M+Na)+.

Step 3: Synthesis of Compound 5c

To a solution of Compound 5b (168 mg, 0.29 mmole) in DCM (2 mL) and DMF (2 mL), CJ35-5 (111 mg, 0.43 mmole), DIPEA (95 mg, 0.50 mmole) were added. The reaction was left for 2 hours at RT. After the removal of solvent, Compound 5c was purified by preparative HPLC (50% $CH_3CN$ in $H_2O$+0.1% TFA; UV 220 nm; Inertsil ODS-3 column 30×250 mm; flow rate 31 mL/min; Compound 5c, RT 6.9 min). The entitled Compound 5c was obtained as a white solid (125 mg; 67%). MS (ESI, negative ion): M/Z: 635.7 (M−H)+.

Step 4: Synthesis of Compound 5d

To a solution of Compound 5c (125 mg, 0.04 mmole) in 4 mL co-solvent DCM/DMF (1:1) and compound MMAE (141 mg, 0.07 mmole) in 2 mL DMF, TBTU (183 mg) and DIPEA (147 mg) were added. The reaction was gone completion after 4 hours. Solvent was removed under a reduced pressure. Inertsil ODS-3 column 30×250 mm; mobile phase AcN/H$_2$O$_4$ 1% gradient to 50%, flow rate 32 mL/min; Compound 5d RT 23.7 min). The entitled Compound 5d was obtained as a white solid (186 mg; 71%). ESI-MS (ESI, positive ion): M/Z: 1338.0 (M+H)$^+$, 1359.9 (M+Na)$^+$.

Step 5: Synthesis of Linker-Drug 5

To a solution Compound 5d 92 mg (0.068 mmole) in 1 mL DCM at 5-8° C. were added dropwise trifloroacetic acid 0.8 mL (10.4 mmole). The cooling bath was removed and stirring was continued for 4 hours. The solvent was removed under reduced pressure, the residue was added 2 mL methanol slurried for 5 mins then solvent was removed. A minimum of DIW (3 mL) was added and lyophilized to give the crude product of Compound 5-deBoc 62 mg as TFA salt.

To a solution of the TFA salt (62 mg, 0.054 mmole) in 1.7 mL DCM were added, with stirring at 0-5° C., trimethylamine (40 μL, 0.272 mmole), followed by a solution of bromoacetyl bromide 60 mg (0.297 mmole) in DCM (0.3 mL). The cooling bath was removed after 2 hours and stirring was continued for 15 hours. The reaction was checked for completion by HPLC and the mixture was evaporated to dryness. Purification by RP-HPLC (the residue was diluted by 4 mL mobile phase solvent, Inertsil ODS-3 column 30×250 mm; flow rate 31 mL/min, mobile phase AcN/H$_2$O with 0.1% TFA gradient from 40% to 60%, Compound 5, i.e. Linker-drug 5 RT 11.08 min UV 215 nm) The product-containing fraction were lyophilized to give the Linker-drug 5 15 mg.

Chemical formula of Linker-drug 5: C$_{61}$H$_{103}$Br$_2$N$_9$O$_{16}$. (ESI, positive ion): M/Z: [M+H]$^+$=1377.6.

Example 6: Preparation of Linker-Drug 6

Linker-drug 6 was synthesized according to the procedures shown in the following scheme.

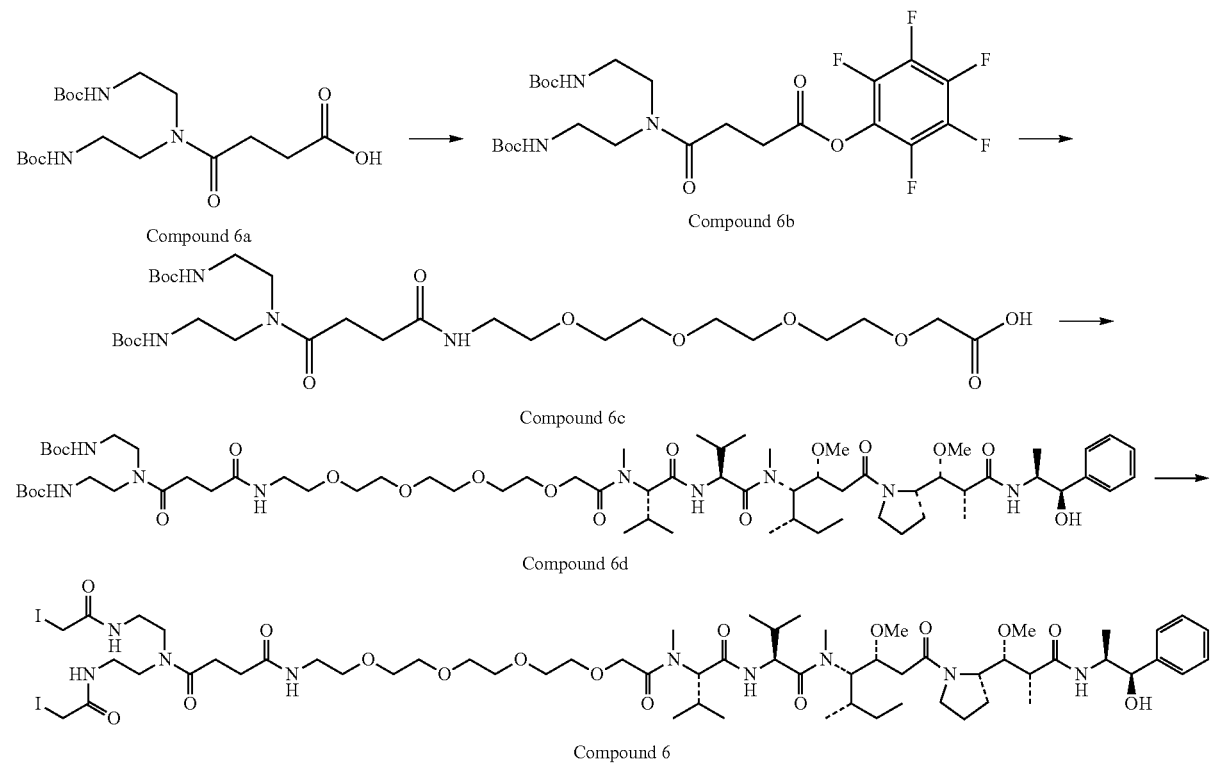

Steps 1-4: Synthesis of Compounds 6a, 6b, 6c, 6d

Compounds 6a, 6b, 6c and 6d were synthesized by the same synthetic procedure as steps 1-4 described in Example 5.

Step 5: Synthesis of Linker-Drug 6

A mixture of Compound 5 (7.9 mg, 5.7 μmol) and sodium iodide (8.6 g, 57.3 μmol) in acetonitrile (2 mL) was stirred for 8 hours at room temperature, and the solvent was evaporated in vacuo. Compound 6 was purified by preparative HPLC (43% CH$_3$CN in H$_2$O, 0.1% TFA; UV 220 nm; Inertsil ODS-3 column 20×250 mm; flow rate 19 mL/min; Compound 6, i.e. Linker-drug 6, RT 23.2 min). The entitled compound Linker-drug 6 was obtained as a white solid (6.7 mg; 4.5 μmol, yield 80%).

Chemical formula of Linker-drug 6: C$_{61}$H$_{103}$I$_2$N$_9$O$_1$. ESI-HIMS (positive ion) M/Z: 1473.6, (M+H)$^+$ 1495.5 (M+Na)$^+$.

Example 7: Preparation of Linker-Drug 7

Linker-drug 7 was synthesized according to the procedures shown in the following scheme.

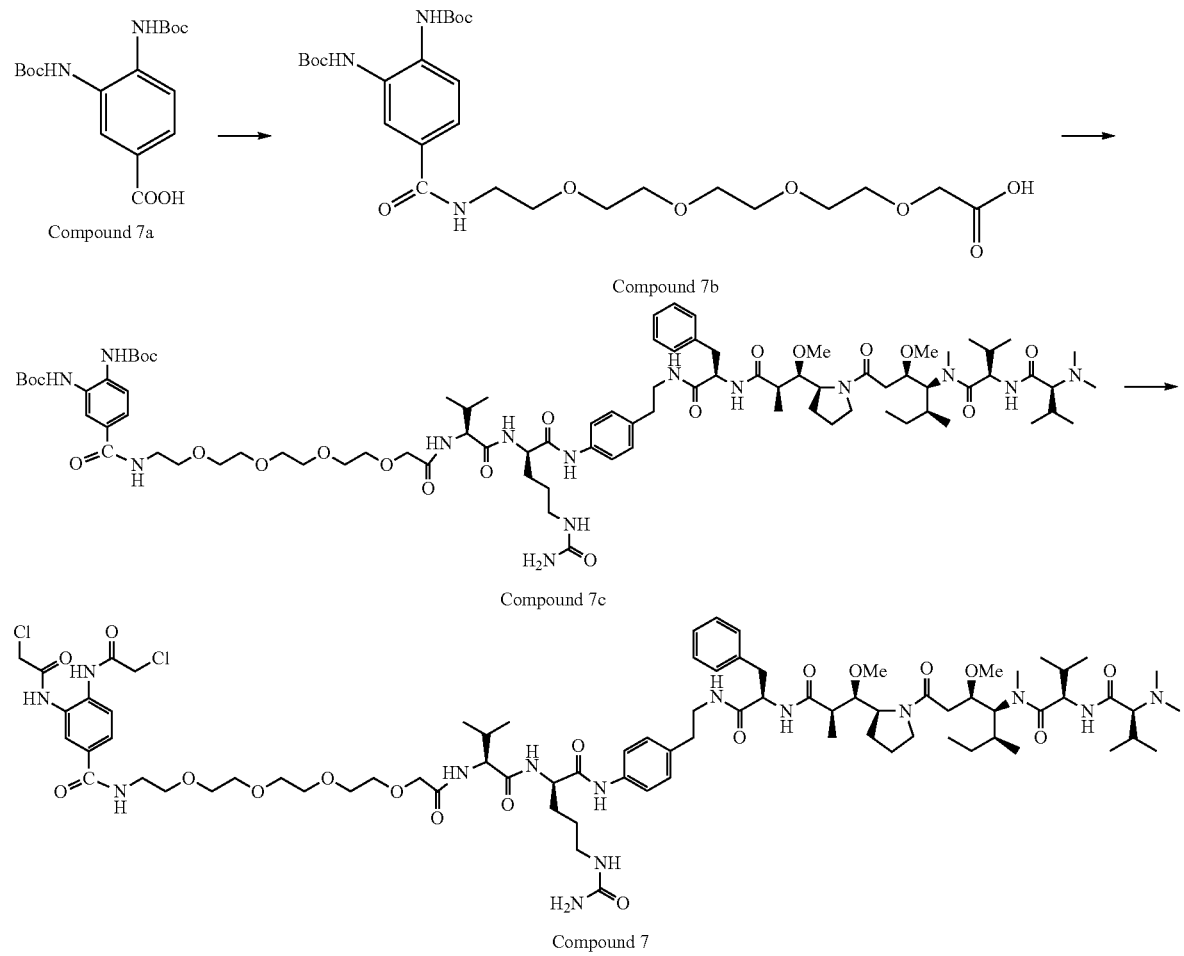

Step 1: Synthesis of Compound 7a 3,4-diaminobenzoic acid (1.52 g, 10 mmol) and di-tert-butoxy dicarbonate (t-Boc)$_2$O, 6.55 g, 30 mmol) with triethylamine (NEt$_3$; 7.0 mL, 60 mmol) in chloroform (CHCl$_3$, 200 mL) were stirred at room temperature (25° C.) for overnight (24 hours). The resulting solution was extracted with water, dried with Na$_2$SO$_4$ to give Compound 7a (N-Boc-3,4-diaminobenzoic acid) (2.0 g, yield 79%) as a brown powder.

Chemical formula of Compound 7a: C$_{17}$H$_{24}$N$_2$O$_6$. $^1$H NMR (500 MHz, d-MeOH) δ 7.96 (s, 1H), 7.75 (dd, 1H, J=8.4, 1.9 Hz), 7.60 (d, 1H, J=8.4, 1.9 Hz), 4.80 (brs, 2H, NH), 1.52 (s, 18H). 13C NMR (150 MHz, d-MeOH) δ 173.2, 156.4, 155.5, 135.7, 133.6, 130.3, 127.9, 127.8, 123.6, 81.7, 81.6, 28.8, 28.7. Mass of Compound 7a (C$_{17}$H$_{24}$N$_2$O$_6$; 352.4 Da) was measured.

Step 2: Synthesis of Compound 7b

To a mixture solution of Compound 7a (500 mg, 1.42 mmole) and pentafluorophenol (313 mg; 1.70 mmol) in DCM (8 mL) was added DCC (351 mg, 1.70 mmol). The mixture was stirred at room temperature for 12 hours, the precipitate was filtered and concentrated in vacuo. To a solution of PFP ester in DCM (1 mL) and DMF (2 mL), L1 (534.8 mg, 2.12 mmole), DIPEA (457.8 mg, 3.54 mmole) were added. The reaction was left for two hour at room temperature. After the removal of solvent, Compound 7b was purified by preparative HPLC (50% CH$_3$CN in H$_2$O+ 0.1% TFA; UV 210 nm; Inertsil ODS-3 column 30×250 mm; flow rate 32 mL/min; Compound 7b RT, 14.6 min). Compound 7b was obtained as a white solid (557 mg, yield 67%).

Chemical formula of Compound 7b: C$_{27}$H$_{44}$N$_3$O$_{11}$. ESI (positive ion) M/Z: 586.2972 for C$_{27}$H$_{44}$N$_3$O$_{11}$, err −0.3 ppm.

Step 3: Synthesis of Compound 7c

To a solution of Compound 7b (40 mg, 68.3 mmole) in 4 mL co-solvent DCM/DMF (1:1) and Val-Cit-APEA-AF (95 mg, 85.4 mmole) in 2 mL DMF, TBTU (68 mg) and DIPEA (52 mg) were added. The reaction was gone completion after 3 hours. Solvent was removed under a reduced pressure. Compound 7c was purified by preparative HPLC. The product-containing fraction was lyophilized to give Compound 7c as a white solid (63.5 mg; yield 55%).

Chemical formula of Compound 7c: C$_{86}$H$_{138}$N$_{14}$O$_{20}$. ESI, positive ion: M/Z: 1689.2 (M+1), 1711.2 (M+Na).

Step 4: Synthesis of Linker-Drug 7

To a solution Compound 7c 20.1 mg (0.012 mmole) in 1.5 mL DCM at 25-27° C. were added dropwise trifloroacetic acid 0.8 mL (10.4 mmole). The water bath was removed and stirring was continued for 4 hours. The solvent was removed under reduced pressure, the residue was added 2 mL methanol and slurried for 5 minutes, then solvent was removed. A minimum of DIW (2 mL) was added and lyophilized to give the crude product Compound 7c-deBoc 23 mg as TFA salt.

Chemical formula of Compound 7c-deBoc: $C_{76}H_{122}N_{14}O_{16}$. ESI, positive ion: M/Z: 1489.0 (M+1), 1511.0 (M+Na), ESI, negative ion: M/Z: 1487.2 (M−1).

Next, to a solution of the TFA salt (22 mg, 0.012 mmole) in DCM/DMF (1/0.3 mL) solution were added, with stirring at 0-5° C., trimethylamine (8 µL, 0.057 mmole), followed by a solution of chloroacetyl chloride 22 mg (0.19 mmole) in DCM (0.3 mL). After 5 minutes stirring, second portion of trimethylamine (8 µL, 0.057 mmole) was added. The cooling bath was removed after 2 hours and stirring was continued for 15 hours. The reaction was checked for completion by HPLC and the mixture was evaporated to dryness. Purification by RP-HPLC (the residue was diluted by 2 mL M.P. solvent, Inertsil ODS-3 column 20×250 mm, 5 µm; flow rate 17.5 mL/min, M.P. 43% AcN/H$_2$O with 0.1% TFA, UV 215 nm) The product-containing fraction (Rt=6.5 min) were lyophilized to give Compound 7, i.e. Linker-drug 7 16 mg, 84% yield Chemical formula of Linker-drug 7: $C_{80}H_{124}Cl_2N_{14}O_{18}$. (ESI, positive ion): M/Z: M+H=1641.0.

Example 8: Preparation of Linker-Drug 8

Linker-drug 8 was synthesized according to the procedures shown in the following scheme.

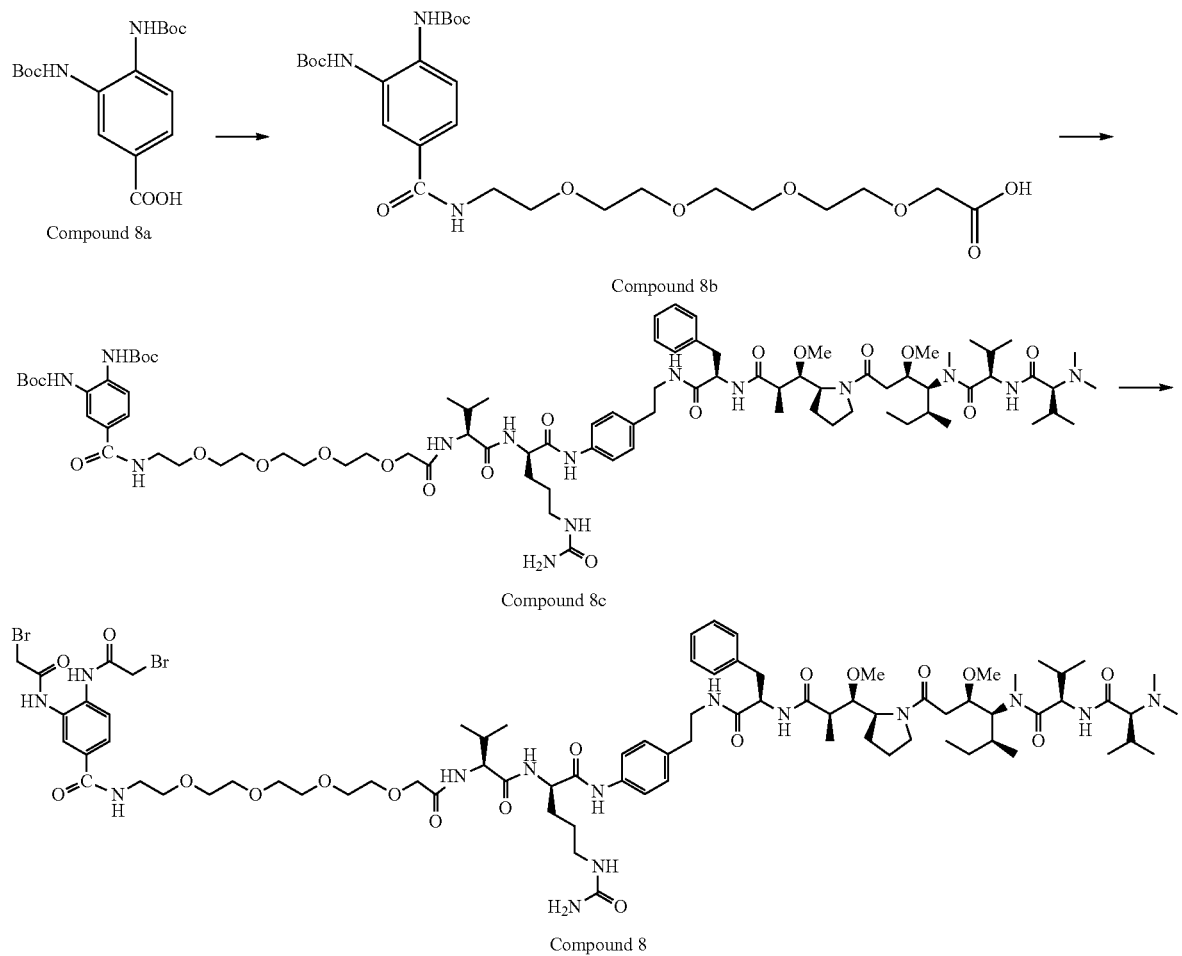

Steps 1-3: Synthesis of Compounds 8a, 8b, 8c

Compounds 8a, 8b, and 8c were synthesized by the same synthetic procedure as steps 1-4 described in Example 7.

Step 4: Synthesis of Linker-Drug 8

To a solution Compound 8c 20 mg (0.031 mmole) in 1.5 mL DCM at 8-10° C. were added dropwise trifloroacetic acid 1 mL (13 mmole). The ice-water bath was removed and stirring was continued for 4 hours. The solvent was removed under reduced pressure, the residue was added 2 mL methanol and slurried for 5 mins then solvent was removed. A minimum of DIW (2 mL) was added and lyophilized to give the crude product of Compound 8c-deBoc 18 mg as TFA salt.

To a solution of the TFA salt in 1 mL DCM were added, with stirring at 0-5° C., trimethylamine (13 µL, 0.093 mmole), followed by a solution of bromoacetyl bromide 13 mg (0.064 mmole) in DCM (0.3 mL). After 15 mins stirring, second portion of trimethylamine (13 μL, 0.094 mmole) was added. The cooling bath was removed after 2 hours and stirring was continued for 4 hours. The reaction was checked for completion by HPLC and the mixture was evaporated to dryness. Purification by RP-HPLC (the residue was diluted by 3 mL M.P. solvent, Inertsil ODS-3 column 30×250 mm; flow rate 31 mL/min, 44% AcN/H$_2$O with 0.1% TFA, UV 220 nm). The product-containing fraction (Rt=7.1 min) were lyophilized to give the Compound 8, i.e. Linker-drug 8 12.4 mg.

Chemical formula of Linker-drug 8: $C_{80}H_{124}Br_2N_{14}O_{18}$. (ESI, positive ion): M/Z: M+H=1728.3.

Example 9: Preparation of Linker-Drug 9

Linker-drug 9 was synthesized according to the procedures shown in the following scheme.

Na$_2$SO$_4$ to give Compound 9a (N-Boc-3,5-diaminobenzoic acid) (0.87 g, yield 83%) as a brown powder.

Chemical formula of Compound 9a: $C_{17}H_{24}N_2O_6$. $^1$H NMR (500 MHz, CDCl$_3$) δ 7.87 (s, 1H, ArH), 7.70 (s, 2H, ArH), 6.90 (bs, 2H, NH), 1.52 (s, 18H, CH$_3$).

Step 2: Synthesis of Compound 9b

To a mixture solution of Compound 9a (74.6 mg, 0.21 mmole) and pentafluorophenol (46 mg; 0.25 mmol) in DCM (6 mL) was added DCC (42 mg, 0.25 mmole). The mixture was stirred at room temperature for 12 hours, the precipitate was filtered and concentrated in vacuo. To a solution of Compound 9b in DCM (1 mL) and DMF (2 mL), L1 (80 mg, 0.31 mmole), DIPEA (68 mg, 0.53 mmole) were added. The reaction was left for two hours at room temperature. After the removal of solvent, Compound 9b was purified by preparative HPLC (50% CH$_3$CN in H$_2$O+0.1% TFA; UV 210 nm; Inertsil ODS-3 column 30×250 mm; flow rate 32

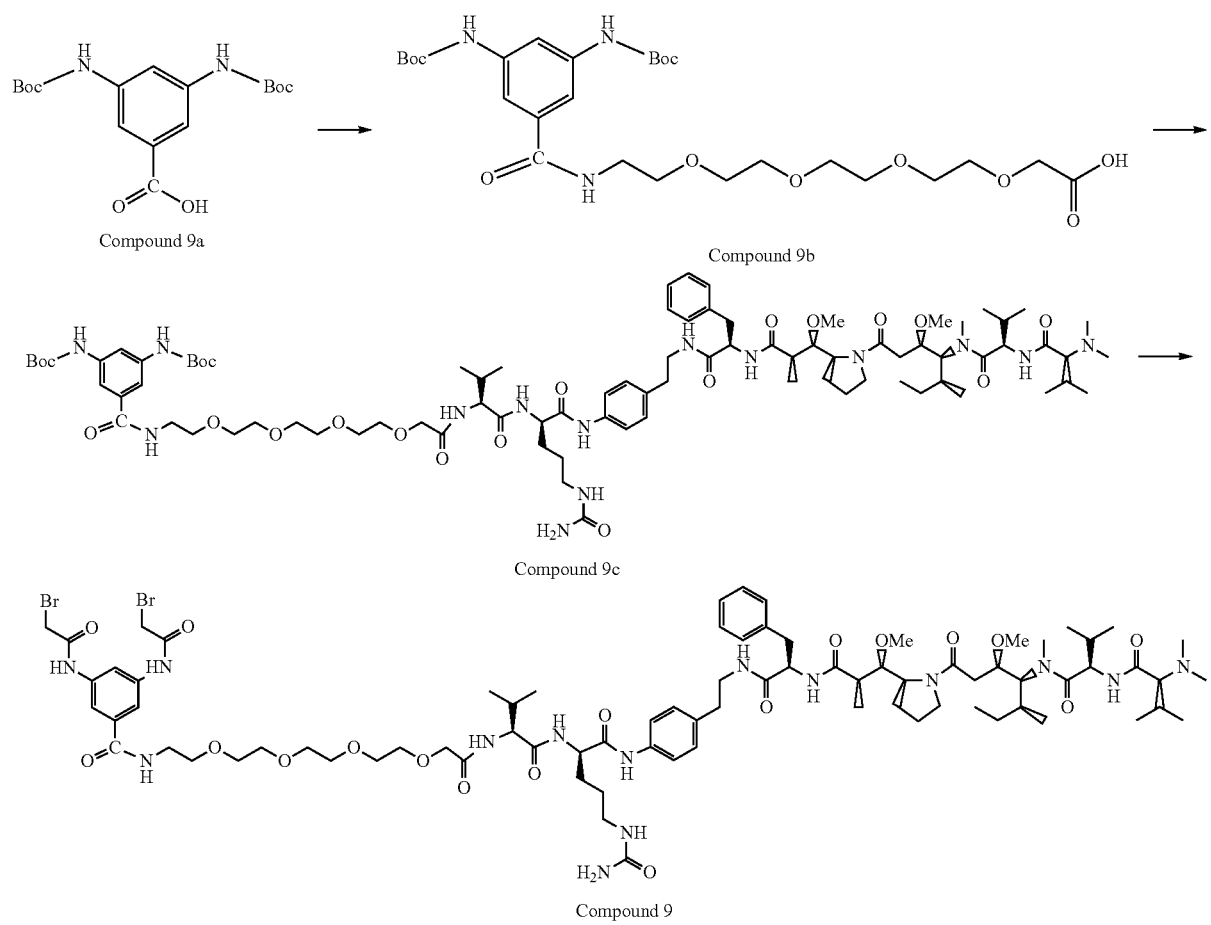

Step 1: Synthesis of Compound 9a

The synthesis of Compound 9a was performed as described in the literature (*Synthesis*, 1986, 48.). 3,5-diaminobenzoic acid (0.45 g, 2.96 mmol) and di-tert-butoxy dicarbonate ((t-Boc)$_2$O, 0.57 g, 8.9 mmol) with triethylamine (NEt$_3$; 2.1 mL, 10.6 mmol) in DCM, 60 mL) were stirred at room temperature (25° C.) for overnight (24 hours). The resulting solution was extracted with water, dried with mL/min; Compound 9b RT, 14.6 min). The Compound 9b was obtained as a white solid (25 mg).

Chemical formula of Compound 9b: $C_{27}H_{43}N_3O_{11}$. ESI (positive ion) M/Z: 586.9, 608.8. Yield: 99%.

Step 3: Synthesis of Compound 9c

To a solution of Compound 9b (25 mg, 0.04 mmole) in 4 mL co-solvent DCM/DMF (1:1) and Val-Cit-APEA-AF (48 mg, 0.04 mmole) in 2 mL DMF, TBTU (44 m) and DIPEA (36 mg) were added. The reaction was gone completion after 4 hours. Solvent was removed under a reduced pressure. 50% CH$_3$CN in H$_2$O+0.1% TFA; UV 210 nm; Inertsil ODS-3 column 30×250 mm; flow rate 32 mL/min; Compound 9b RT, 14.6 min). The Compound 9c was obtained as a white solid (52 mg; yield 70%).

Chemical formula of Compound 9c: C$_{86}$H$_{138}$N$_{14}$NaO$_{10}$. (ESI, positive ion): M/Z: 1689.9 (M+1). ESI-HIMS (positive ion) M/Z: 1710.0214 [M+Na]$^+$ for C$_{86}$H$_{138}$N$_{14}$NaO$_{10}$, err: 6.4 ppm.

Step 4: Synthesis of Linker-Drug 9

To a solution of Compound 9c 52 mg (0.031 mmole) in 1.5 mL DCM at 8-10° C. were added dropwise trifloroacetic acid 0.8 mL (10.4 mmole). The ice-water bath was removed and stirring was continued for 4 hours. The solvent was removed under reduced pressure, the residue was added 2 mL methanol and slurried for 5 mins then solvent was removed. A minimum of DIW (2 mL) was added and lyophilized to give the crude product of Compound 9c-de-Boc 35 mg as TFA salt.

To a solution of the TFA salt (35 mg, 0.021 mmole) in 1 mL DCM were added, with stirring at 0-5° C., trimethylamine (13 μL, 0.093 mmole), followed by a solution of bromoacetyl bromide 19 mg (0.094 mmole) in DCM (0.3 mL). After 15 mins stirring, second portion of trimethylamine (13 μL, 0.094 mmole) was added. The cooling bath was removed after 2 h and stirring was continued for 15 hours. The reaction was checked for completion by HPLC and the mixture was evaporated to dryness. Purification by RP-HPLC (the residue was diluted by 3 mL M.P. solvent, Inertsil ODS-3 column 30×250 mm; flow rate 32 mL/min, 43% AcN/H$_2$O with 0.1% TFA, UV220 nm). The product-containing fraction (Rt=7.6 min) were lyophilized to give the Compound 9, i.e. Linker-drug 9 13.3 mg.

Chemical formula of Linker-drug 9: C$_{80}$H$_{124}$Br$_2$N$_{14}$O$_{18}$. (ESI, positive ion): M/Z: M+H=1728.5, ESI-HIMS (positive ion) M/Z: 1727.7682, [M+H]$^+$ for C$_{60}$H$_{94}$Br$_2$N$_8$NaO$_{15}$, 1727.7658 err: 1.4 ppm.

Synthesis of Val-Cit-APEA-AF

In step 3 of Example 9, the compound Val-Cit-APEA-AF was synthesized according to the procedures shown in the following scheme.

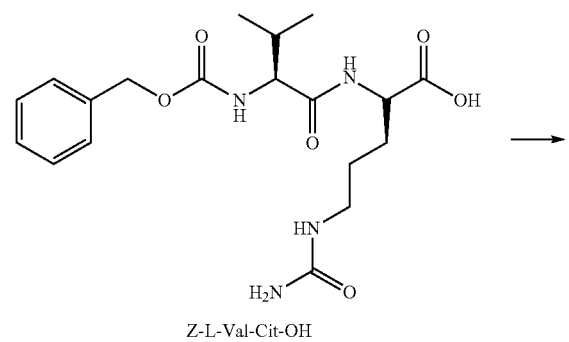

Z-L-Val-Cit-OH

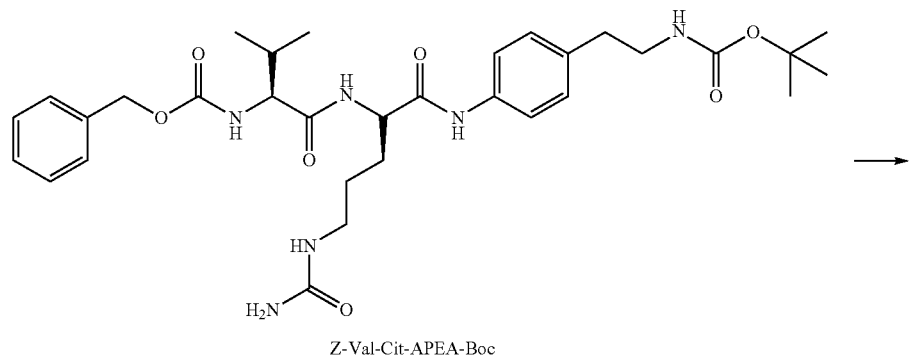

Z-Val-Cit-APEA-Boc

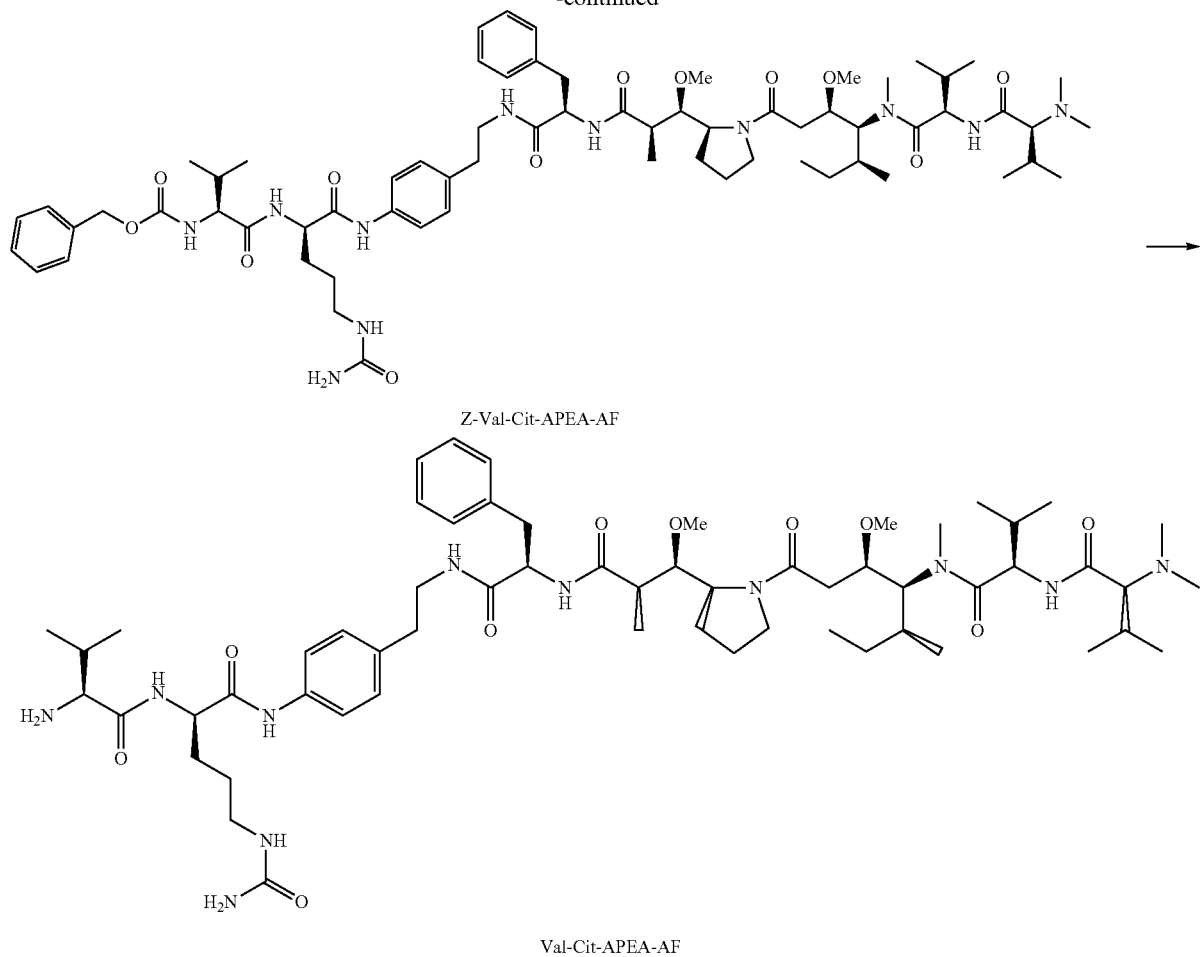

Z-Val-Cit-APEA-AF

Val-Cit-APEA-AF

Step 3-1: Synthesis of Z-Val-Cit-APEA-Boc

Z-L-Val-Cit-OH (4.0 g, 9.79 mmol) was charged into a mixture of dichloromethane (250 mL) and isopropanol (50 mL). Then, tert-butyl 4-aminophenethylcarbamate (2.95 g, 12.5 mmol) and EEDQ (4.95 g, 20 mmol) were added into the mixture. The mixture was stirred at room temperature (25° C.) for 36 hours. The solvents were removed under reduced pressure at 40° C., and ether (300 mL) was then added to the residue. The mixture was centrifugalized for 1 hour. The clear ether solution was removed. The solid product was re-suspended in ether (300 mL) and sonicated for 10 minutes. The mixture was centrifugalized for 1 hour again. Then, the solid product was collected as described above. This process was repeated again. Finally, the collected solid product was dried under vacuum to give 4.5 g of target product with about 90% purity. (HPLC, 210 nm), yield 65.5%.

Step 3-2: Synthesis of Z-Val-Cit-APEA-AF

To a solution of the Z-Val-Cit-APEA-Boc (169 mg, 0.642 mmol) in DCM (4 mL) was added TFA (2 mL). The mixture was stirred at room temperature for 1 hour, after which time the solvents were removed in vacuo. The crude product was used without further purification. DeBoc crude compound Z-Val-Cit-APEA (184 mg, 0.28 mmole) was dissolved in a 10 mL mix solvent (DCM:DMF=1:0.1) and AF (300 mg, 0.35 mmole), TBTU (200 mg), and DIPEA (162 mg, 0.353 mmole). The reaction mixture was stirred at room temperature for 17 hours. The solvent was evaporated in vacuo and purified by HPLC using a preparative column (50% $CH_3CN$ in $H_2O$+0.1% TFA; UV 210 nm; Inertsil ODS-3 column 30×250 mm; flow rate 32 mL/min; Z-Val-Cit-APEA-AF RT 14.6 min, 223 mg, with a yield of 62%).

Chemical formula of Z-Val-Cit-APEA-AF: $C_{67}H_{103}N_{11}O_{12}$. ESI (positive ion) M/Z: 1256.1.

Step 3-3: Synthesis of Val-Cit-APEA-AF

To a solution of the Z-Val-Cit-APEA-AF (90 mg, 0.0717 mmol) in ethanol (10 mL) was added 10% Pd/C (9 mg). The resulting mixture was stirred under an atmosphere of $H_2$ for 4 hours, after which time the mixture was filtered through a celite pad. The celite pad was washed with EtOAc and the filtrate was concentrated in vacuo to provide the product Val-Cit-APEA-AF. Yield: 99%.

Chemical formula of Val-Cit-APEA-AF: $C_{59}H_{97}N_{11}O_{10}$. ESI-HIMS (negative ion) M/Z: 1142.7316 [M+Na]$^+$ for $C_{59}H_{97}N_{11}NaO_{10}$, err: −0.3 ppm.

Example 10: Preparation of Linker-Drug 10

Linker-drug 10 was synthesized according to the procedures shown in the following scheme.

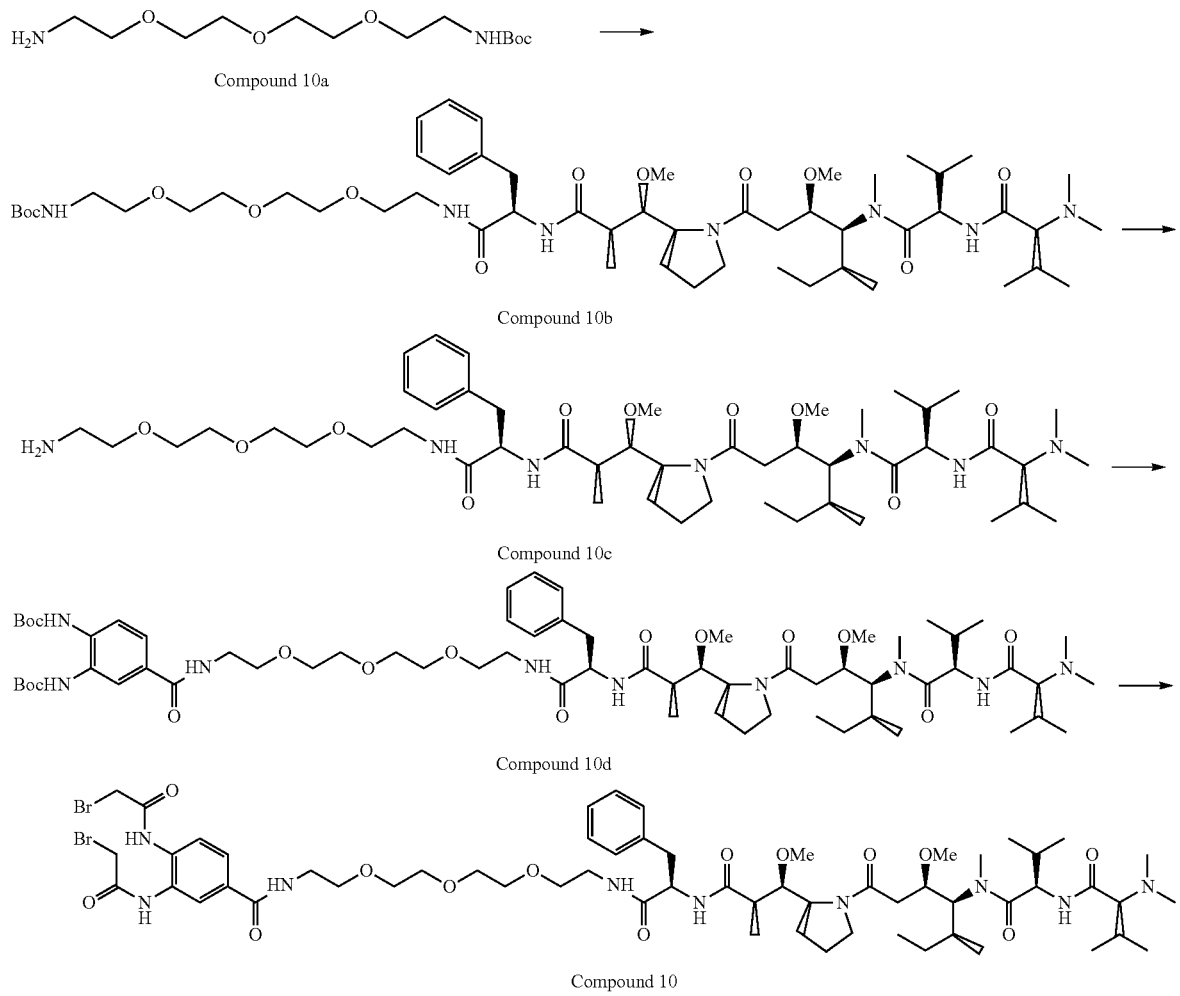

Compound 10a

Compound 10b

Compound 10c

Compound 10d

Compound 10

Step 1: Synthesis of Compound 10a

The diamine (1 equivalent) in DCM solution (10 mL/mmol) was treated with $Boc_2O$ (0.15 equivalent) for 5 hours at room temperature. The organic phase was washed with water, until all the unreacted diamine was extracted. The Boc-protected compound Compound 10a was quantitatively recovered after drying ($MgSO_4$) and concentration under vacuum. $^1H$ NMR ($CDCl_3$, 500 MHz) 3.74 (m, 1H), 3.70 (m, 1H), 3.62 (m, 8H), 3.54 (m, 4H), 3.31 (m, 2H), 1.44 (s, 9H), ESI, positive ion: M/Z: 293.7 (M+1), 316.7 (M+Na).

Step 2: Synthesis of Compound 10b

To a solution of Auristatin F (200 mg, 0.23 mmole) in 4 mL co-solvent DCM/DMF (1:1) and Compound 10a (75 mg, 0.25 mmole) in 2 mL DMF, TBTU (220 mg, 0.68 mmole) and DIPEA (180 mg, 1.39 mmole) were added. The reaction was gone completion after 2 hours. Solvent was removed under a reduced pressure. Inertsil ODS-3 column 30×250 mm, 10 Acetonitrile 43%, flow rate 32 mL/min, UV220, T31-1, RT 9.3 min). The entitled Compound 10b was obtained as a white solid (151 mg; 0.14 mmole, 64%). ESI, positive ion: M/Z: 1021.7 (M+1), 1043.7 (M+Na).

Step 3: Synthesis of Compound 10c

To a solution of the Compound 10b (151 mg) in DCM (4 mL) was added TFA (2 mL). The mixture was stirred for 1 hour at RT, after which time the solvents were removed in vacuo. The crude product of Compound 10c was used without further purification.

Step 4: Synthesis of Compound 10d

To a mixture solution of N-Boc-3,4-Diaminobenzoic acid (60 mg, 0.17 mmole) and pentafluorophenol (47 mg; 0.25 mmol) in DCM (6 mL) was added DCC (51.5 mg, 0.25 mmole). The mixture was stirred at room temperature for 12 hours, the precipitate was filtered and concentrated in vacuo. To a solution of PFP ester was added Compound 10c (235 mg, 0.25 mmole) and DIPEA (55 mg, 0.42 mmole) were added. The reaction was left for one hour at RT. After the removal of solvent, Compound 10d was purified by preparative HPLC (Inertsil ODS-3 column 30×250 mm, 5 μm, Acetonitrile 42% (0-5 min) to 50% (5-13 min) to 55% (13-25 min), flow rate 31 mL/min, UV220, T31-3, RT 13.8 min). The entitled Compound 10d was obtained as a white solid (173 mg, 0.13 mmole, 81%). ESI, positive ion: M/Z: 1255.3, 12773 (M+Na).

To a solution Compound 10d 20 mg (0.016 mmole) in 4 mL DCM at 20-23° C. water bath were added dropwise trifloroacetic acid 2 mL (10.4 mmole). The water bath was removed and stirring was continued for 2 hours. The solvent was removed under reduced pressure, the residue was added 2 mL methanol and slurried for 5 mins then solvent was removed. A minimum of DIW (2 mL) was added and lyophilized to give the crude product Compound 10d-deBoc 23 mg as TFA salt.

To a solution of the TFA salt (23 mg, 0.016 mmole) in DCM/DMF (1/0.5 mL) solution were added, with stirring at 0-5° C., trimethylamine (10 µL, 0.072 mmole), followed by a solution of bromoacetyl bromide 24 mg (0.12 mmole) in DCM (0.3 mL). After 5 mins stirring, second portion of trimethylamine (10 µL, 0.072 mmole) was added. The cooling bath was removed after 2 hours and stirring was continued for 15 hours. The reaction was checked for completion by HPLC and the mixture was evaporated to dryness. Purification by RP-HPLC (the residue was diluted by 2 mL M.P. solvent, Inertsil ODS-3 column 20×250 mm, 5 µm; flow rate 17.5 mL/min, M.P. 42% AcN/$H_2O$ with 0.1% TFA, UV 215 nm) and the product-containing fraction (RT=7.47 min) were lyophilized to give the Compound 10, i.e., Linker-drug 10 12 mg, 58% yield.

Chemical formula of Linker-drug 10: $C_{59}H_{93}Br_2N_9O_{13}$. (ESI, positive ion): M/Z: M+H=1297.5.

Example 11: Preparation of Linker-Drug 11

Linker-drug 11 was synthesized according to the procedures shown in the following scheme.

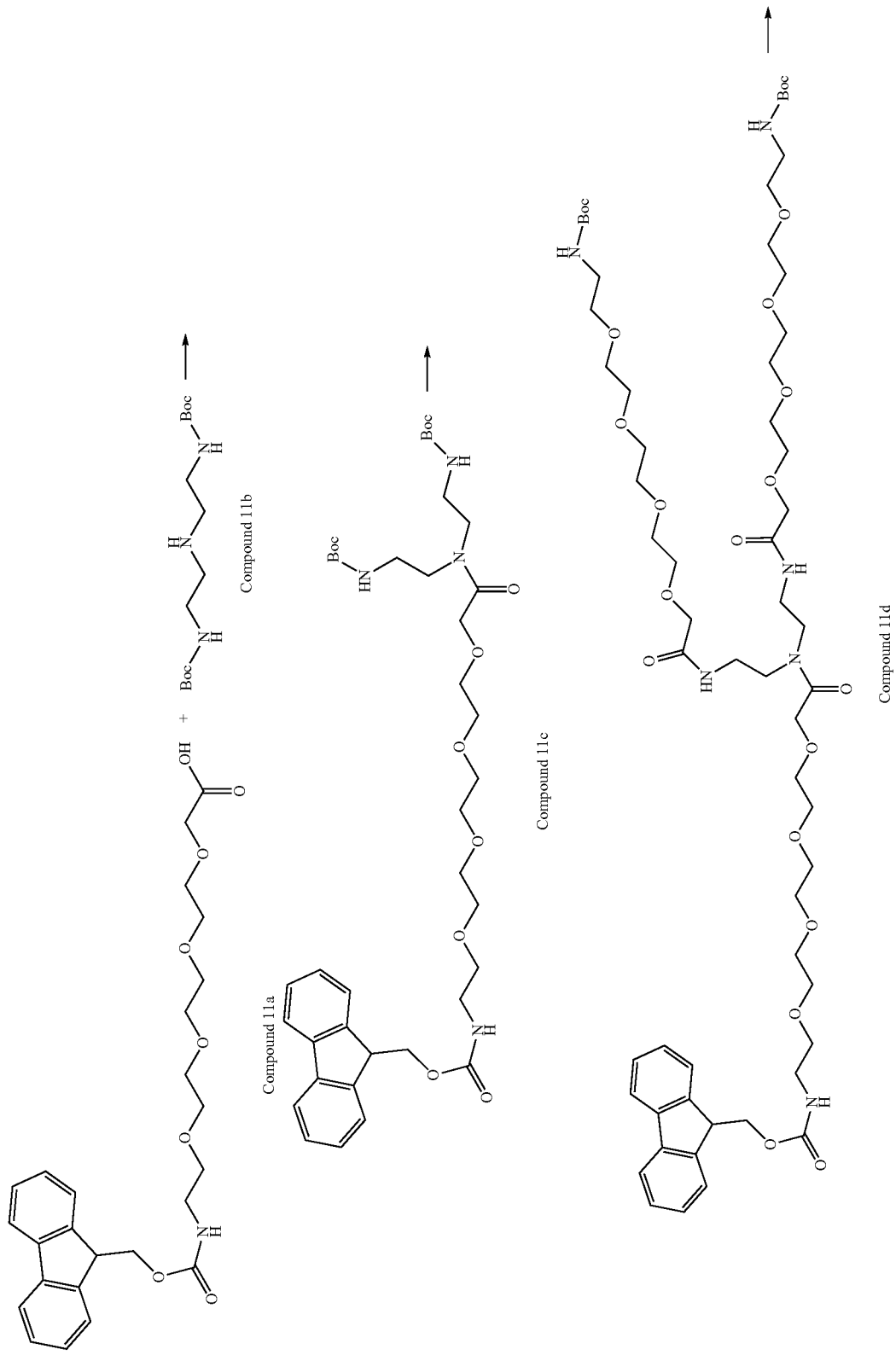

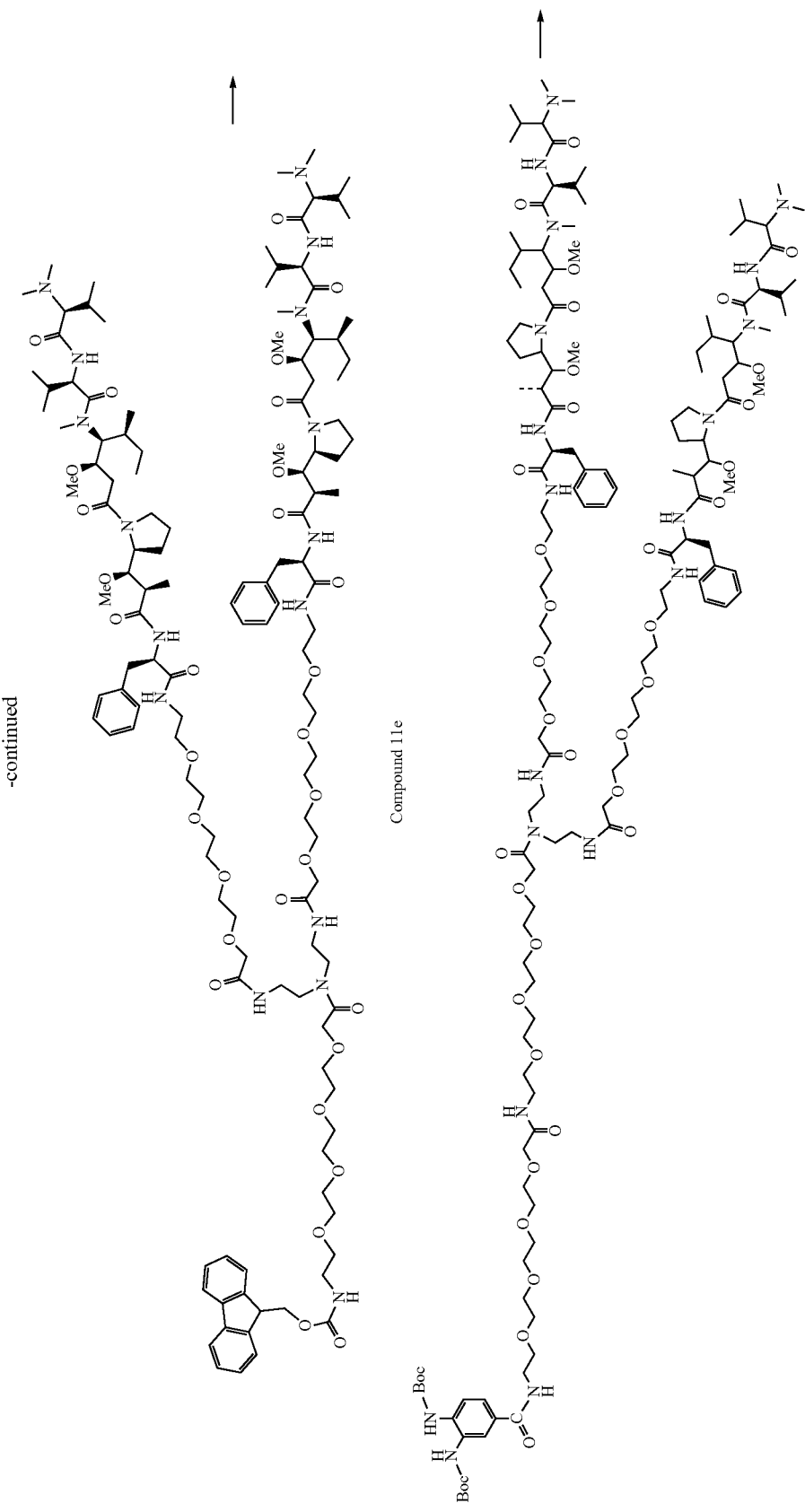

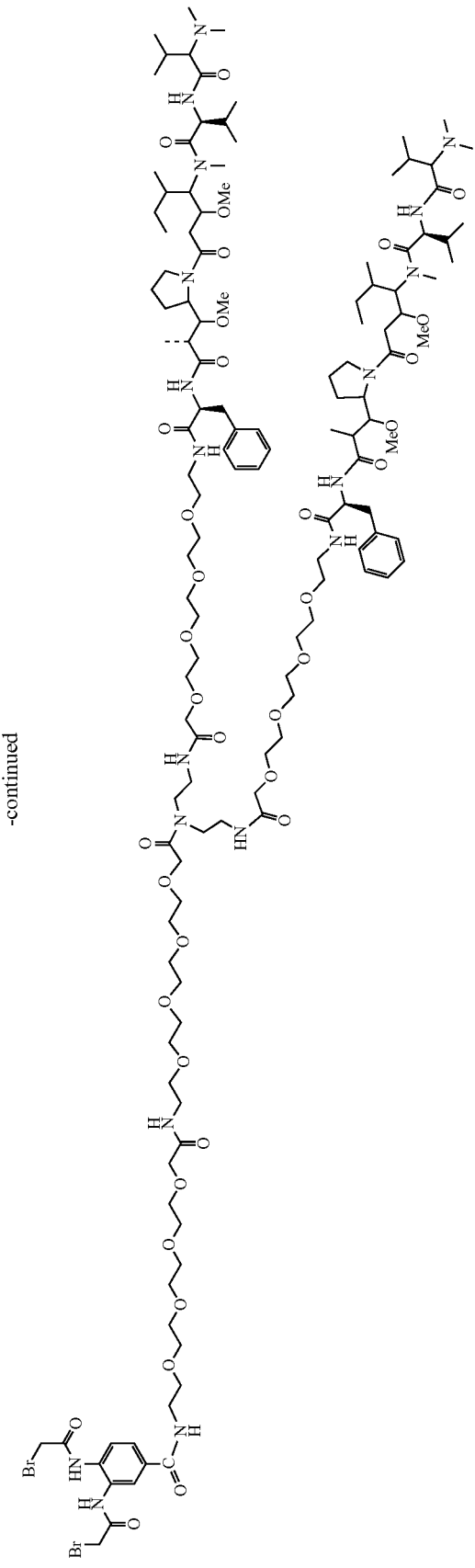
Compound 11

Step 1: Synthesis of Compound 11a

L1 (0.79 g, 3.14 mmol) and $K_2CO_3$ (1.04 g, 7.50 mmol) were dissolved in 5.8 mL of water and stirred at room temperature for 15 minutes after which N-(9-fluorenyl-methoxycarbonyl) succinimide (Fmoc-OSu, 1.28 g, 3.79 mmol) was added and the mixture was stirred for 24 hours, while the progress of the reaction was monitored by TLC ($CHCl_3$/MeOH/AcOH, 5:1:0.06). The salt was filtered and the filtrate was washed with $Et_2O$, acidified to pH 1 using 3 N HCl, and the desired compound extracted with DCM. After removing the solvent in vacuo, Purification by RP-HPLC, the product-containing fraction was lyophilized to give Compound 11a (1.08 g, yield 73%).

Chemical formula of Compound 11a: $C_{25}H_1NO_8$ required $[M+H]^+$=474.2, found $[M+H]^+$=474.9, $[M+Na]^+$=496.9.

Step 2: Synthesis of Compound 11b

Imidazole (0.78 g, 11.5 mmol) was suspended in 10 mL DCM at room temperature. Di-tert-butyl dicarbonate ($Boc_2O$) (2.62 g, 12 mmol) was added portion wise. The reaction mixture was stirred for one hour at room temperature. The reaction mixture was washed with water, dried over $Na_2SO_4$, filtered and the volatiles were removed under reduced pressure. The residue was dissolved in 4 mL toluene and diethylene triamine (0.595 mL, 5.5 mmol) was added. The reaction mixture was stirred for two hours at 60° C. 10 mL DCM was added, and the organic phase was washed with water. The organic phase was dried over $Na_2SO_4$, filtered and reduced under reduced pressure. Flash Column on silica using a gradient of methanol (MeOH) in DCM with triethylamine gave the title compound as a colorless solid. (Compound 11b, 1.02 g, yield 61%).

Chemical formula of Compound 11b: $C_{14}H_{29}N_3O_4$. $^1$H-NMR (500 MHz, $CDCl_3$): 1.41 (s, 18H), 1.58 (bs, 1H), 2.66-2.77 (m, 4H), 3.13-3.26 (m, 4H), 4.96 (bs, 2H).

Step 3: Synthesis of Compound 11c

To a solution of Compound 11a (645.2 mg, 1.36 mmol) in 4 mL DCM and Compound 11b (413 mg, 1.36 mmol) in 2 mL DMF, TBTU (110 mg) and DIPEA (844 mg) were added. The reaction was gone completion after 2 hours. Solvent was removed under a reduced pressure. Inertsil ODS-3 column 30×250 mm; flow rate 32 mL/min; Compound 11c RT, 17 min). Compound 11c was obtained as a white solid (738 mg; yield 76%).

Chemical formula of Compound 11c: $C_{39}H_{58}N_4O_{11}Na$. (ESI, positive ion): M/Z: 760.4 (M+1); 782.4 (M+Na). HRMS found 781.4005 for $C_{39}H_{58}N_4O_{11}Na$, err: 1.3 ppm.

Step 4: Synthesis of Compound 11d

To a solution Compound 11c (218.6 mg, 0.288 mmole) in 4 mL DCM at 0° C. were added dropwise trifloroacetic acid 2 mL. The cooling bath was removed and stirring was continued for 3 hours. The solvent was removed under reduced pressure. The residue was added 2 mL methanol stirred for 5 minutes, then, the solvent was removed. A minimum of DIW (2 mL) was added and lyophilized to give the crude product Compound 11c-deBoc 27 mg as TFA salt.

Chemical formula of Compound 11c-deBoc: $C_{29}H_{42}N_4O_7$. ESI, positive ion): M/Z: 558.4 (M+1); 580.3 (M+Na).

Next, to a solution of the TFA salt (250 mg, 0.44 mmole) in 4 mL DCM (8 mL) and compound N-Boc-L1 (628 mg, 1.76 mmole) in 2 mL DMF, TBTU (831.6 mg) and DIPEA (552 mg) were added. The reaction was gone completion after 3 hours. Solvent was removed under a reduced pressure. Compound 11d was purified by preparative HPLC. The product-containing fraction was lyophilized to give Compound 11d as a white solid (356 mg; yield 65%).

Chemical formula of Compound 11d: $C_{59}H_{96}N_6O_{21}$. ESI, positive ion: M/Z: 1226.7 (M+1), 1248.8 (M+Na).

Step 5: Synthesis of Compound 11e

To a solution Compound 11d (300 mg, 0.288 mmole) in 4 mL DCM at 0° C. were added dropwise trifloroacetic acid 2 mL. The cooling bath was removed and stirring was continued for 3 hours. The solvent was removed under reduced pressure. The residue was added 2 mL methanol stirred for 5 minutes then solvent was removed. A minimum of DIW (2 mL) was added and lyophilized to give the crude product Compound 11d-deBoc as TFA salt.

Chemical formula of Compound 11d-deBoc: $C_{49}H_{80}N_6O_{17}$. Required $[MH^+]$ 1024.56, found $[M+H]^+$ 1026.7. $[M+Na]^+$1048.7.

Next, to a solution of the TFA salt (130 mg, 0.12 mmole) in 2 mL DCM and Auristatin F (272 mg, 0.3 mmole) in 2 mL DMF, TBTU (235 mg, 0.73 mmole) and DIPEA (173 mg, 1.34 mmole) were added. The reaction was gone completion after 1 hour. Solvent was removed under a reduced pressure. Inertsil ODS-3 column 30×250 mm; flow rate 32 mL/min; Compound 11e RT, 17 min). Compound 11e was obtained as a white solid (261 mg; yield 83%).

Chemical formula of Compound 11e: $C_{129}H_{210}N_{16}O_{31}$. (ESI, positive ion): M/Z: 1242.3 $(M+2H)^{2+}$; 829.0 $(M+3H)^{3+}$.

Step 6: Synthesis of Compound 11f

To a solution Compound 11e (20.8 mg, 0.288 mmole) in 2 mL DCM at 0° C. were added dropwise diethylamine 1 mL. The cooling bath was removed and stirring was continued for 4 hours. The solvent was removed under reduced pressure. The residue was added 2 mL methanol stirred for 5 minutes then solvent was removed. A minimum of DIW (2 mL) was added and lyophilized to give the crude product Compound 11e-deFmoc as TFA salt.

Chemical formula of Compound 11e-deFmoc: $C_{114}H_{200}N_{16}O_{29}$. ESI, positive ion: 2259.5 (M+1), 2281.5 (M+Na).

Next, to a solution of CJ24-1 (64 mg, 0.11 mmole) in 4 mL co-solvent DCM (6 mL) and Compound 11e-deFmoc (123.5 mg, 0.054 mmole) in 2 mL DMF, EDC (26 mg, 0.13 mmole) and DIPEA (14 mg, 0.11 mmole) were added. The reaction was gone completion after 12 hours. Solvent was removed under a reduced pressure. Compound 11f was purified by preparative HPLC. The product-containing fraction was lyophilized to give Compound 11f as a white solid (169.8 mg; yield 55%).

Chemical formula of Compound 11f: $C_{125}H_{211}N_{19}O_{33}$. ESI, positive ion: 1415 $(M+2H)^{2+}$.

Step 7: Synthesis of Linker-Drug 11

To a solution Compound 11f 26.3 mg (0.0092 mmole) in 4 mL DCM at 20-23° C. water bath was added dropwise trifloroacetic acid 2 mL (10.4 mmole). The water bath was removed and stirring was continued for 2 hours. The solvent was removed under reduced pressure, the residue was added 2 mL methanol and slurried for 5 minutes, and then, the solvent was removed. A minimum of DIW (2 mL) was added and lyophilized to give the crude product Compound 11f-deBoc 26 mg as TFA salt.

Next, to a solution of the TFA salt (26 mg, 0.0092 mmole) in DCM/DMAc (1/0.5 mL) solution were added, with stirring at 0-5° C., trimethylamine (40 μL, 0.288 mmole) in DCM (0.2 mL), followed by a solution of bromoacetyl bromide 30 mg (0.148 mmole) in DCM (0.3 mL). The cooling bath was removed after 2 hours and stirring was continued for 15 hours. The reaction was checked for completion by HPLC and the mixture was evaporated to dryness. Purification by RP-HPLC (the residue was diluted by 3.5 mL M.P. solvent, Inertsil ODS-3 column 30×250 mm, 10 μm; flow rate 31 mL/min, M.P. from 35% (0-6.5 min) to 43% (6.5-20 min) AcN/$H_2O$ with 0.1% TFA, UV220 nm) and the product-containing fraction (Rt=11.71 min) were lyophilized to give the Compound 11, i.e. Linker-drug 11 12 mg, yield 46%.

Chemical formula of Linker-drug 11: $C_{135}H_{227}Br_2N_{19}O_{37}$. (ESI, positive ion): M/Z: $[M+H]^{+2}$=1435.9.

Example 12: Preparation of Linker-Drug 12

Linker-drug 12 was synthesized according to the procedures shown in the following scheme.

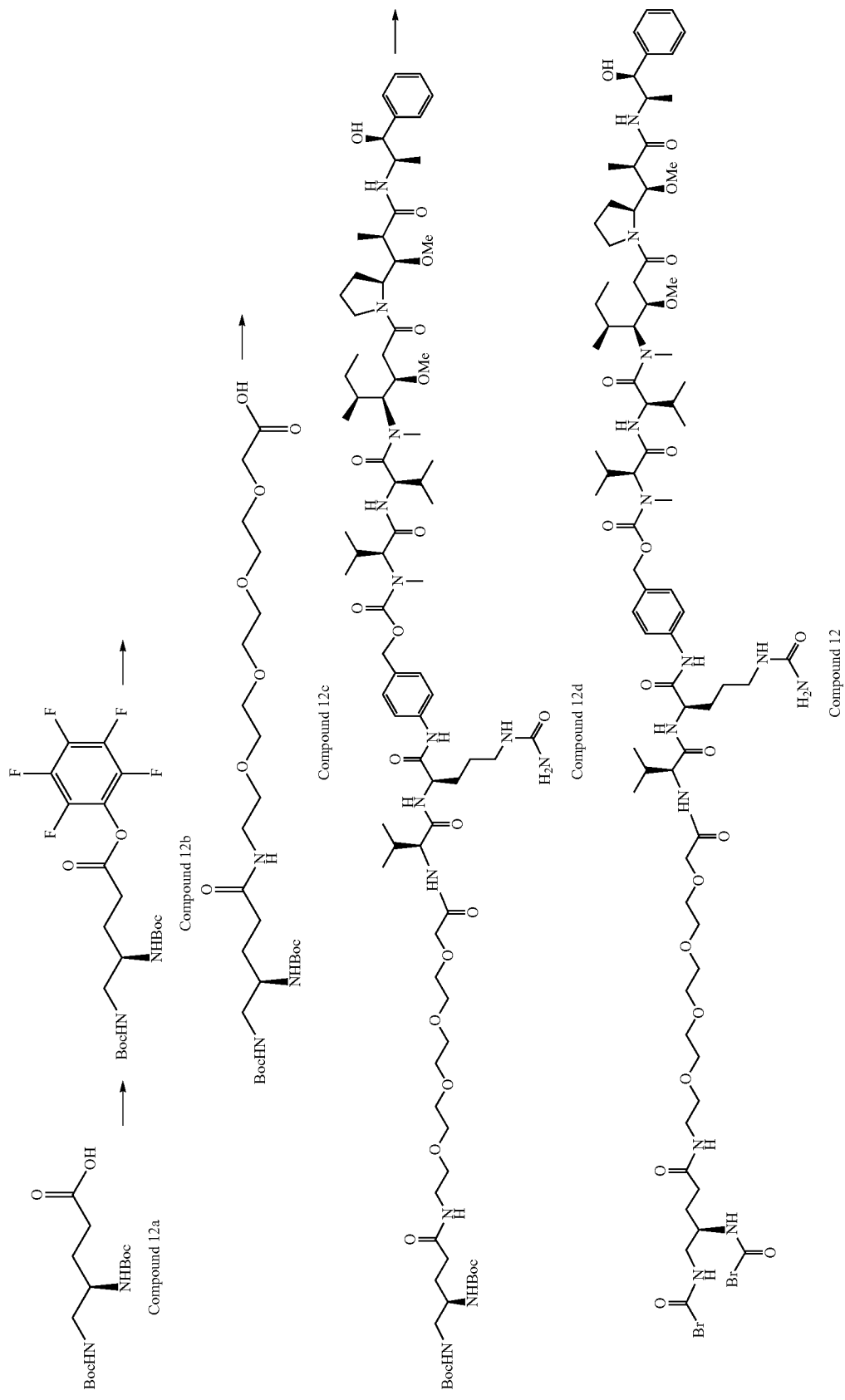

Step 1: Synthesis of Compound 12a

A solution of di-t-butyl dicarbonate (5.2 g, 23.8 mm) in acetonitrile was added slowly to a stirred solution of (s)-5-(aminomethyl)pyrrolidin-2-one (EDA-4, 1.29 g, 11.3 mmol), then DMAP (180 mg, 1.5 mm) was added. The reaction was complete in 6 h (as monitored by TLC). The solution was concentrated and the solid was purified by flash column chromatography (hexane/EtoAC (1:5)) to give the di-boc-protected intermediate EDA-5 as a solid (1.82 g, 51%). A solution of LiOH×H$_2$O (0.36 g, 19 mmol) in water (12 ml) was added to a stirred solution of EDA-5 (1.03 g, 3.28 mmol) in 10 ml THF. The mixture was stirred overnight then acidified with 1N HCl. The solution was concentrated and the mixture is extracted with EtOAc, washed with brine, dried over MgSO$_4$ and concentrated. The solid was purified by flash column chromatography (ethyl acetate/hexane (1/4) to give the title Compound 12a (0.81 g, 75%) as a solid. M/Z=333.9 [M+H]+, M/Z=331.8 [M−1]$^−$; 0.1H NMR (CDCl3) 1.41 (s, 9H); 1.43 (s, 9H); 1.61-1.84 (m, 2H), 2.42-2.45 (m, 2H), 3.17-3.22 (t, 2H), 3.67 (s, 1H), 4.95 (bs, 2H).

Step 2: Synthesis of Compound 12b

To a mixture solution of Compound 12a (133 mg, 0.40 mmole) and pentafluorophenol (110 mg; 0.60 mmol) in DCM (6 mL) was added DCC (123 mg, 0.60 mmole). The mixture was stirred at room temperature for 12 hours to obtain a crude product of Compound 12b.

Step 3: Synthesis of Compound 12b

CJ35-5 (151 mg, 0.60 mmole) and DIPEA (130 mg, 1.00 mmole) were added. The reaction was left for 2 hours at RT. After the removal of solvent, Compound 12c was purified by preparative HPLC (50% CH$_3$CN in H$_2$O+0.1% TFA; UV 220 nm; Inertsil ODS-3 column 30×250 mm; flow rate 31 mL/min; Compound 12c, RT 6.9 min). The entitled Compound 12c was obtained as a white solid (160 mg; 0.28 mmole, 70%). MS (ESI, negative ion): M/Z: 564.8 (M−H)$^+$.

Step 3: Synthesis of Compound 12d

To a solution of Compound 12c (60 mg, 0.106 mmole) in 4 mL co-solvent DCM/DMF (2:2) and compound Val-Cit-APEA-AF (118.8 mg, 0.106 mmole) in 2 mL DMF, TBTU (113 mg, 0.297 mmole) and DIPEA (79.5 mg, 0.616 mmole) were added. The reaction was gone completion after 4 hours. Solvent was removed under a reduced pressure. Inertsil ODS-3 column 30×250 mm, 10 μm, acetonitrile 43%, flow rate 32 mL/min, UV 220, Compound 12d, RT 9.3 min). The entitled Compound 12d was obtained as a white solid 113.8 mg, 0.068 mmole, yield 64.2%. ESI, positive ion: M/Z: 1671.7 (M+1), 1693.7 (M+Na).

Synthesis of Linker-Drug 12

To a solution of Compound 12d (24 mg, 0.014 mmole) in 1.5 mL DCM at 8-10° C. were added dropwise trifloroacetic acid (1 mL, 13 mmole). The ice-water bath was removed and stirring was continued for 4 hours. The solvent was removed under reduced pressure, the residue was added 2 mL methanol and slurried for 5 mins then solvent was removed. A minimum of DIW (2 mL) was added and lyophilized to give the crude product Compound 12d-deBoc 19 mg as TFA salt.

To a solution of the TFA salt in 1 mL DCM were added, with stirring at 0-5° C., trimethylamine (13 μL, 0.093 mmole), followed by a solution of bromoacetyl bromide 22 mg (0.119 mmole) in DCM (0.3 mL). After 15 mins stirring, second portion of trimethylamine (13 μL, 0.094 mmole) was added. The cooling bath was removed after 2 hours and stirring was continued for 15 hours. The reaction was checked for completion by HPLC and the mixture was evaporated to dryness. Purification by RP-HPLC (the residue was diluted by 3 mL M.P. solvent, Inertsil ODS-3 column 30×250 mm; flow rate 31 mL/min, 44% AcN/H$_2$O (0-15 min), 50% (15-25 min), flow rate 31 mL/min, Compound 12, i.e. Linker-drug 12, 18.3 mins, UV 220 nm) The product-containing fraction (retention time=18.3 mins) were lyophilized to give the Linker-drug 12 1.4 mg. (ESI, positive ion): M/Z: M+H=1711.8 (Br79, M+1), 1713.9 (Br81, M+1).

Example 13: Preparation of Linker-Drug 13

Linker-drug 13 was synthesized according to the procedures shown in the following scheme.

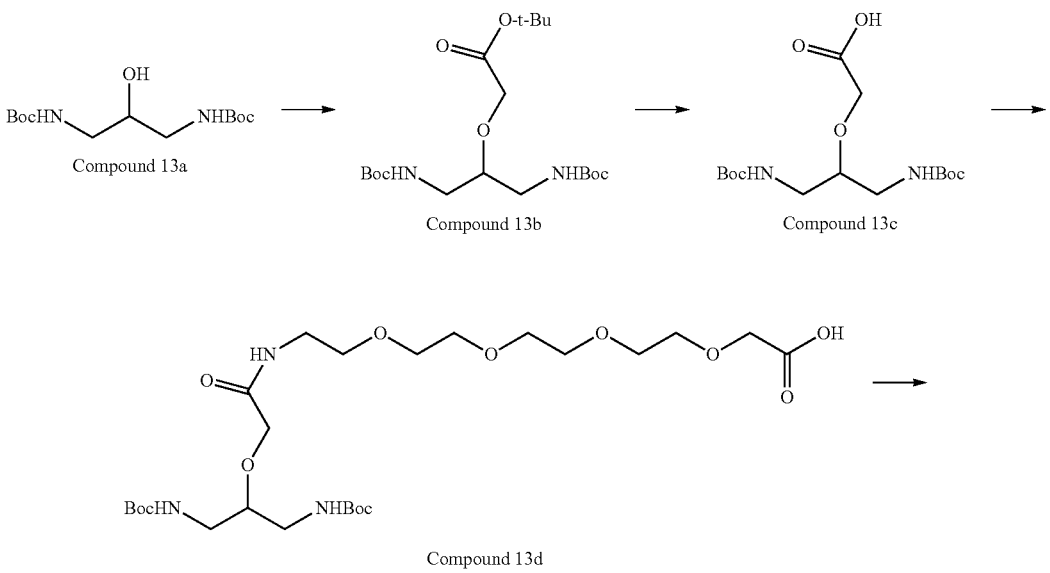

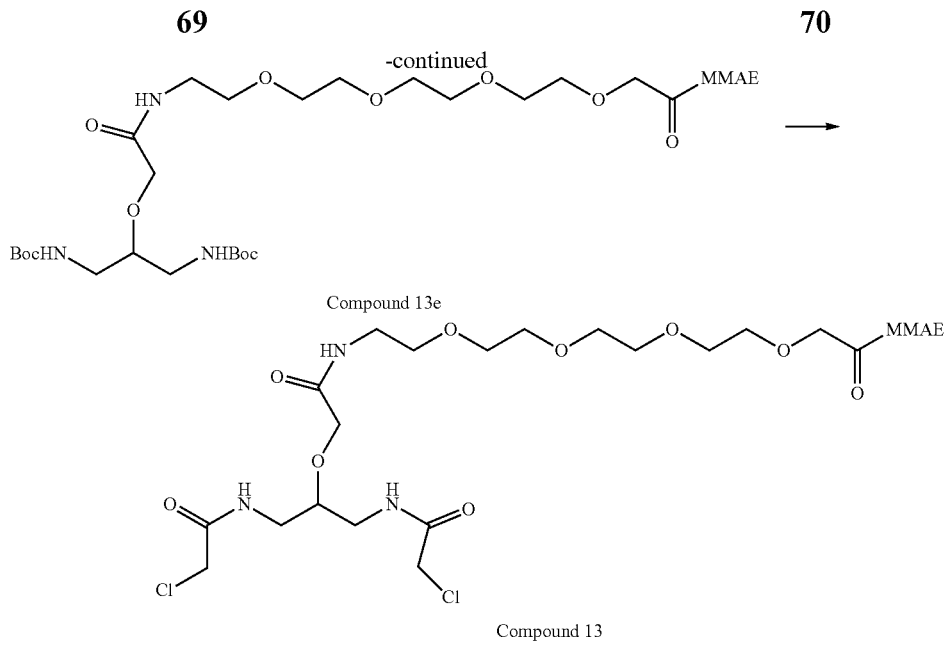

Compound 13

Step 1: Synthesis of Compound 13a
(1.3-Di(Tert-butyloxycarbonylamino)propan-2-ol)

The Compound 13a was prepared according to literature method (Chem. Eur. J. 2004, 10, 1215-1226)

A solution of di-tert-butyl dicarbonate (4.80 g, 22 mmol) in $CH_2Cl_2$ (4 mL) was added slowly to a stirred solution of 1,3-diamino-propanol (901 mg, 10.0 mmol) and triethylamine (164 mL, 1.18 mmol) in THF/MeOH (1:5, 10 mL). The reaction was complete in 2 hours (as monitored by TLC). The solution was concentrated and the oily residue was purified by flash column chromatography (Hexane/EtOAc (1:4)) to give the Boc-protected intermediate Compound 13a as a colorless solid (1.59 g, 55%); 1H NMR (500 MHz, $CDCl_3$) δ=5.16 (bs, 2H), 3.73 (m, 1H), 3.22-3.16 (m, 4H), 1.43 (s, 18H) ppm; M/Z (ES+), 291.7 (M+H), 313.7 (M+Na).

Step 2: Synthesis of Compound 13b (N-(3-(tert-Butoxycarbonylamino)-2-(ethoxycarbonylmethyl-oxy)-prop-1yl) Carbamic Acid tert-butyl Ester)

Tert-Butyl bromoacetate (2.07 g, 10.7 mmol) was added to a stirred solution of Compound 13a (1.23 g, 4.23 mmol) in dry THF (2 mL) at room temperature. Sodium hydride (0.47 g, 4.5 molar equivalent) was added slowly over 1 hour. After an additional 5 hours the reaction mixture was filtered over celite and evaporated. The residue was purified by flash column chromatography (Hexane/EtOAc (8:2)) to give Compound 13b as a colorless oil; $^1$H NMR (500 MHz, CDCl3): =4.21 (q, J=7 Hz, 2H), 4.15 (s, 2H), 3.45 (m, 1H), 3.48-3.06 (m, 4H), 1.42 (s, 18H), 1.27 (t, J=7 Hz, 3H); MS m/z (ES$^-$), 348.2 (M-$^t$-BuO).

Step 3: Synthesis of Compound 13c (N-(3-(tert-Butoxycarbonylamino)-2-(ethoxycarbonylmethyl-oxy)-prop-1yl) Carbamic Acid)

The Compound 13b (30 mmol) was dissolved in THF (100 ml) and MeOH (100 ml), 6 N NaOH (150 ml) was added and the reaction mixture was stirred at RT for 1 hour. The solvent was removed in vacuo, and 6 N HCl (155 ml) was added at 0° C. After extraction with $CH_2Cl_2$, drying over $Na_2SO_4$, filtering off of the drying agent and distilling off of the solvent, the crude product was obtained, which was purified via column chromatography (silica gel, hexane/ethyl acetate 3/1 to 1/3) to give a white solid (3.9 g, 74.5%). 1H NMR (500 MHz, $CDCl_3$): δ 5.21 (br, 1H), 4.72 (br, 1H), 4.62 (br, 1H), 3.92 (s, 2H), 3.71-3.68 (t, 1H), 3.44-3.29 (m, 4H), 1.39 (s, 18H, CH3); MS m/z (ES$^-$), 347.7 (M-1), 273.6 (M-$^t$-BuO).

Step 4: Synthesis of Compound 13d

To a mixture solution of DETA-4 (58 mg, 0.16 mmole) and pentafluorophenol (36.8 mg; 0.20 mmol) in DCM (6 mL) was added DCC (41.2 mg, 0.20 mmole). The mixture was stirred at room temperature for 12 hours. CJ35-5 (62.7 mg, 0.25 mmole), DIPEA (54 mg, 0.41 mmoles) were added. The reaction was left for 3 hours at RT. After the removal of solvent, Compound 13d was purified by preparative HPLC (50% to 35% $CH_3CN$ in $H_2O$+0.1% TFA; UV 220 nm; Inertsil ODS-3 column 30×250 mm; flow rate 31 mL/min; Compound 13d). The entitled Compound 13d was obtained as a white solid (73 mg; 76%). MS (ESI, negative ion): M/Z: 581.1 (M−H)$^+$.

Step 5: Synthesis of Compound 13e

To a solution of Compound 13d (57.5 mg, 0.098 mmole) in 4 mL co-solvent DCM/DMF (1:1) and compound MMAE (70.5 mg, 0.098 mmole) in 2 mL DMF, TBTU (47.6 mg, 0.14 mmole) and DIPEA (31.8 mg, 0.24 mmole) were added. The reaction was gone completion after 4 hours. Solvent was removed under a reduced pressure. Inertsil ODS-3 column 30×250 mm, 10 acetonitrile 50-35%, flow rate 32 mL/min, UV 220, Compound 13e). The entitled Compound 13e was obtained as a white solid 101.6 mg, yield 80.2%. ESI, positive ion: M/Z: 1286.9 (M+1), 1304.9 (M+Na).

Step 6: Synthesis of Linker-Drug 13

To a solution of Compound 13e (12 mg, 0.009 mmole) in 1 mL DCM at 8-10° C. were added dropwise trifloroacetic acid 0.8 mL (10.4 mmole). The ice-water bath was removed after 1 hour and stirring was continued at room temperature for 4 hours. The solvent was removed under reduced pressure, the residue was added 2 mL methanol and slurried for 5 mins then solvent was removed. A minimum of DIW (2 mL) was added and lyophilized to give the crude product Compound 13e-deBoc 11 mg as TFA salt.

To a solution of the TFA salt in 1 mL DCM were added, with stirring at 0-3° C., trimethylamine (20 µL, 0.136 mmole), followed by a solution of bromoacetyl bromide 15 mg (0.074 mmole) in DCM (0.25 mL). After 15 mins stirring, second portion of trimethylamine (10 µL, 0.068 mmole) was added. The cooling bath was removed after 2 hours and stirring was continued for 15 hours. The reaction was checked for completion by HPLC and the mixture was evaporated to dryness. Purification by RP-HPLC (the residue was diluted by 3 mL M.P. solvent, Inertsil ODS-3 column 30×250 mm 10 acetonitrile 43% (0-9 min) 50% (9-15 min) 60% (15-25 min) flow Rate 31 mL/min, UV220 nm) The product-containing fraction (Retention time=14.1 min) were lyophilized to give the Compound 13, i.e. Linker-drug 13 3.5 mg. (ESI, positive ion): M/Z: M+H=1322.7 (Br79, M+1) 1324.7 (Br81, M+1).

Example 14: Preparation of Linker-Drug 14

Linker-drug 14 was synthesized according to the procedures shown in the following scheme.

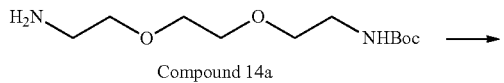

Compound 14a

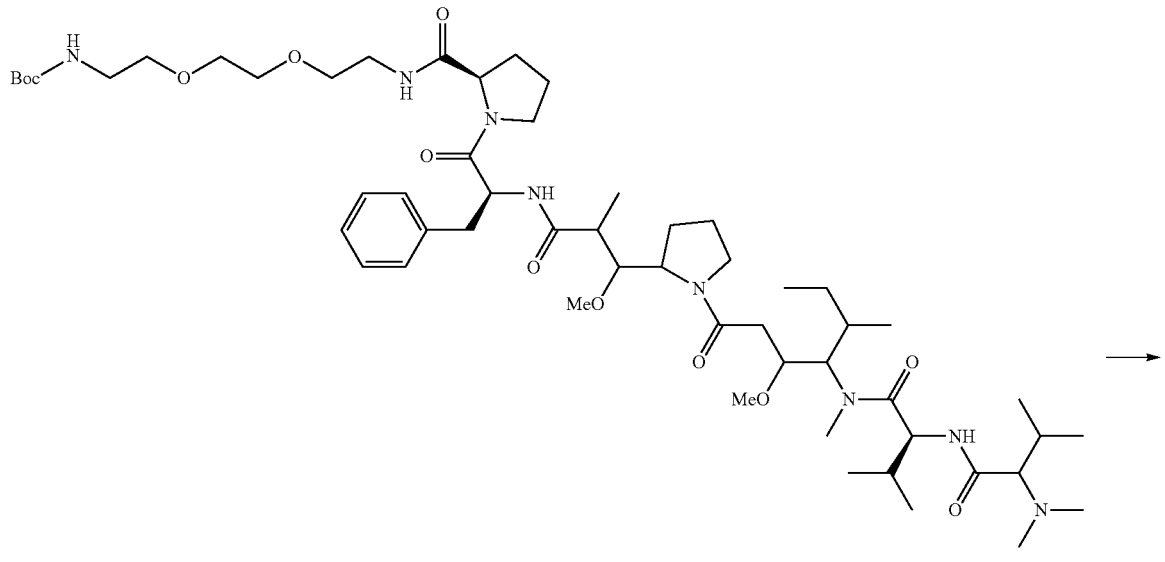

Compound 14b

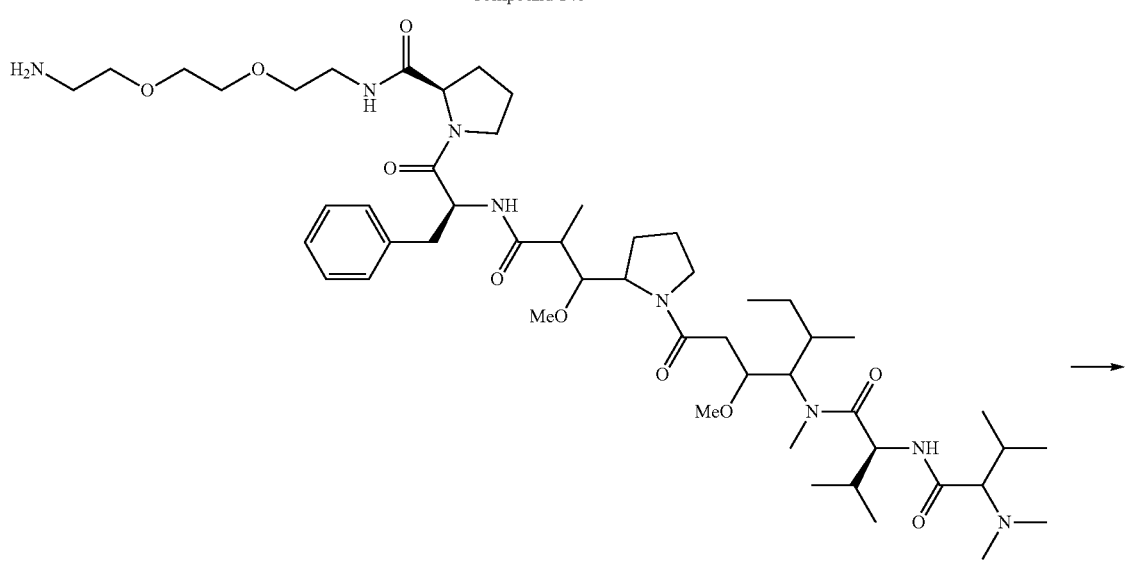

Compound 14c

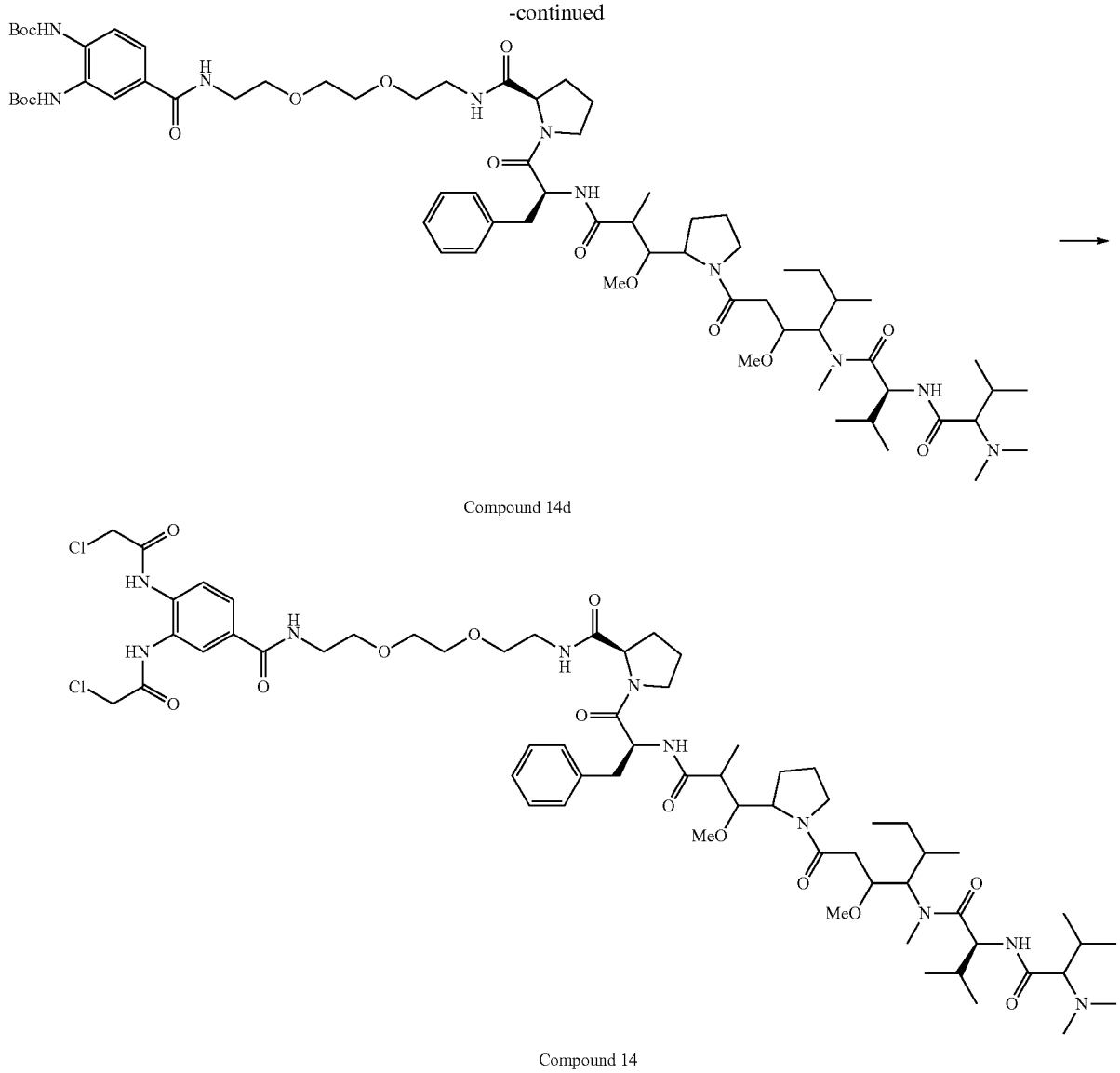

Compound 14d

Compound 14

Step 1: Synthesis of Compound 14a

The 10 g 2,2'-(Ethylenedioxy)bis(ethylamine) in DCM solution (100 mL) was treated with Boc$_2$O (2.25 g, 0.01 mole) for 5 hours at 0° C. and 18 hours at room temperature. The organic phase was washed with 100 ml water, until all the unreacted diamine was extracted. The Boc-protected compound was quantitatively recovered after drying (MgSO$_4$) and concentration under vacuum (2.53 g, 0.01 mole): $^1$H NMR (500 MHz, CDCl$_3$): δ 1.42 (s, 9H), 1.63 (br m, 2H, NH$_2$), 2.86 (t, 2H, J=5.5 Hz), 3.30 (m, 2H), 3.50 (m, 4H), 3.49-3.61 (m, 8H), 5.30 (br s, 1H, NHCO$_2$).

Step 2: Synthesis of Proline-AF

To a solution of Auristatin F (500 mg, 0.58 mmole) in 12 mL DCM and Proline-t-butyl ester (110 mg, 0.64 mmole), HATU (330 mg, 0.86 mmole) and DIPEA (188 mg, 1.45 mmole) were added. The reaction was gone completion after 3-4 hours. Solvent was removed under a reduced pressure. To above solution in DCM (6 mL) was added TFA (2 mL). The mixture was stirred for 5 hours at RT, after which time the solvents were removed in vacuo. Inertsil ODS-3 column 30×250 mm, flow rate 31 mL/min, mobile phase AcN 35% (0-7 min) 43% (7-16 min) 43% (7-16 min), 100% (16 min-), water with 0.1% TFA UV 220 nm, Proline-AF, Retention time 9.1 min). The entitled compound Proline-AF (441.2 mg, 90%) was obtained as a white solid. ESI (positive ion), 844.1 [M+H]$^+$, 866.6 [M+Na]$^+$.

Step 3: Synthesis of Compound 14b

To a solution of Proline-AF (504.3 mg, 0.59 mmole) in 4 mL co-solvent DCM/DMF (1:1) and compound N-Boc-PEG-amine (N-Boc-2,2'-(ethylenedioxy)diethylamine), 163 mg, 0.106 mmole) in 2 mL DMF, HATU (340 mg, 0.89 mmole) and DIPEA (193 mg, 1.49 mmole) were added. The reaction was gone completion after 2 hours. Solvent was removed under a reduced pressure. Inertsil ODS-3 column 30×250 mm, 10 μm, AcN 43% (0-15 min) 100% (15 min-), flow rate 32 mL/min, UV 220, Compound 14b, RT 11.5 min). The entitled Compound 14b was obtained as a white solid 530 mg, yield 82.8%. ESI, positive ion: M/Z: 1074.6 [M+H]$^+$, 1096.9 [M+Na]$^+$.

Step 4: Synthesis of Compound 14c

To a solution of the Compound 14b (530 mg) in DCM (4 mL) was added TFA (2 mL). The mixture was stirred for 1.6 hours at 0° C., after which time the solvents were removed in vacuo. The crude product of Compound 14c (TFA salt) was used without further purification. ESI, positive ion: M/Z: 974.8 [M+H]$^+$, 996.9 [M+Na]$^+$.

Step 5: Synthesis of Compound 14d

To a mixture solution of N-Boc-3,4-Diaminobenzoic acid (1 g, 2.84 mmole) and pentafluorophenol (784 mg; 4.26 mmol) in DCM (18 mL) was added DCC (880 mg, 4.27 mmole). The mixture was stirred at room temperature for 12 hours, the precipitate was filtered and concentrated in vacuo. The column was eluted with n-Hexane/EtOAc (4:1). The fractions containing the target compound were collected and concentrated under reduced pressure to produce N-Boc-3, 4-Diaminobenzoic acid PFP ester (11-1, 1.47 g, 2.84 mmole, yield 80%); $^1$H-NMR (500 MHz; CDCl3) d: 8.12 (s; 1H); 7.97 (s; 2H), 7.25 (s; 1H), 1.5 (s, 18H), ESI, negative ion): M/Z: 517.9 (M$^-$).

To a solution of N-Boc-3,4-Diaminobenzoic acid PFP ester (255 mg, 0.49 mmole) in 4 mL co-solvent DCM/DMF (1:1) and Compound 14c (480.6 mg, 0.49 mmole) in 2 mL DMF, and DIPEA (317.5 mg, 2.46 mmole) were added. The reaction was gone completion after 5 hours. Solvent was removed under a reduced pressure. Inertsil ODS-3 column 30×250 mm, 10 µm, AcN 35% (0-5 min) 43% (5-11 min) 50% (11-20 min) 55% (20-25 min) 65% (25-30 min) 100% (30 min-), flow rate 32 mL/min, UV 220, Compound 14d, retention time 18.1 min). The entitled Compound 14d (450 mg, 0.344 mmole, yield 70%) was obtained as a white solid. ESI (positive ion): 1309.0 [M+H]$^+$, 1331.0 [M+Na]$^+$.

Step 5: Synthesis of Linker-Drug 14

To a solution Compound 14d (25 mg, 19 mole) in 4 mL DCM at 20-23° C. water bath were added dropwise trifloroacetic acid 2 mL (10.4 mmole). The water bath was removed and stirring was continued for 2 hours. The solvent was removed under reduced pressure, the residue was added 2 mL methanol and slurried for 5 mins then solvent was removed. A minimum of DIW (2 mL) was added and lyophilized to give the crude product Compound 14d-deBoc as TFA salt. ESI (Positive ion): 1108.9 [M+H]$^+$, 1130.9 [M+Na]$^+$.

To a solution of the TFA salt (24 mg, 19 mole) in DCM/DMF (1.2/0.5 mL) solution were added, with stirring at 0-5° C., trimethylamine (40 µL, 0.288 mmole) in DCM (0.2 mL), followed by a solution of chloroacetyl chloride 21 mg (0.185 mmole) in DCM (0.3 mL). The cooling bath was removed after 2 hours and stirring was continued at RT. for 15 hours. The reaction was checked for completion by HPLC and the mixture was evaporated to dryness. Purification by RP-HPLC (the residue was diluted by 3.5 mL M.P. solvent, Inertsil ODS-3 column 30×250 mm, 10 um; flow rate 31 mL/min, M.P. from AcN 35% (0-5.5 min) 43% (5.5-16 min) 100% (16 min-), with 0.1% TFA, UV220 nm) and the product-containing fraction (retention time 10.81 min) were lyophilized to give the Compound 14, i.e. Linker-drug 14 (20 mg, 83% yield). ESI, positive ion: M/Z: 1260.8 [M+H]$^+$, 1282.9 [M+Na]$^+$=1282.9.

Example 15: Preparation of Linker-Drug 15

Linker-drug 15 was synthesized according to the procedures shown in the following scheme.

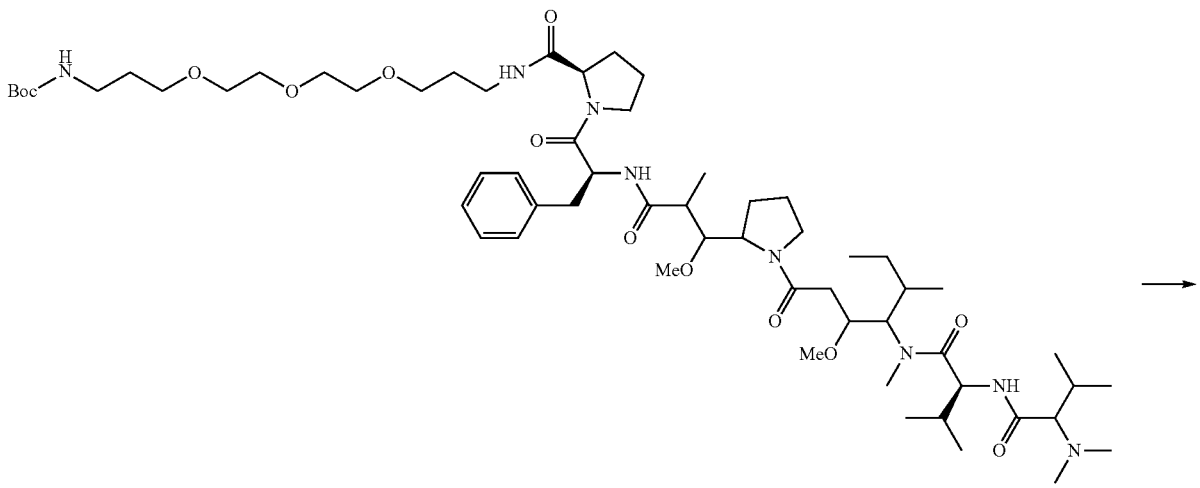

Compound 15a

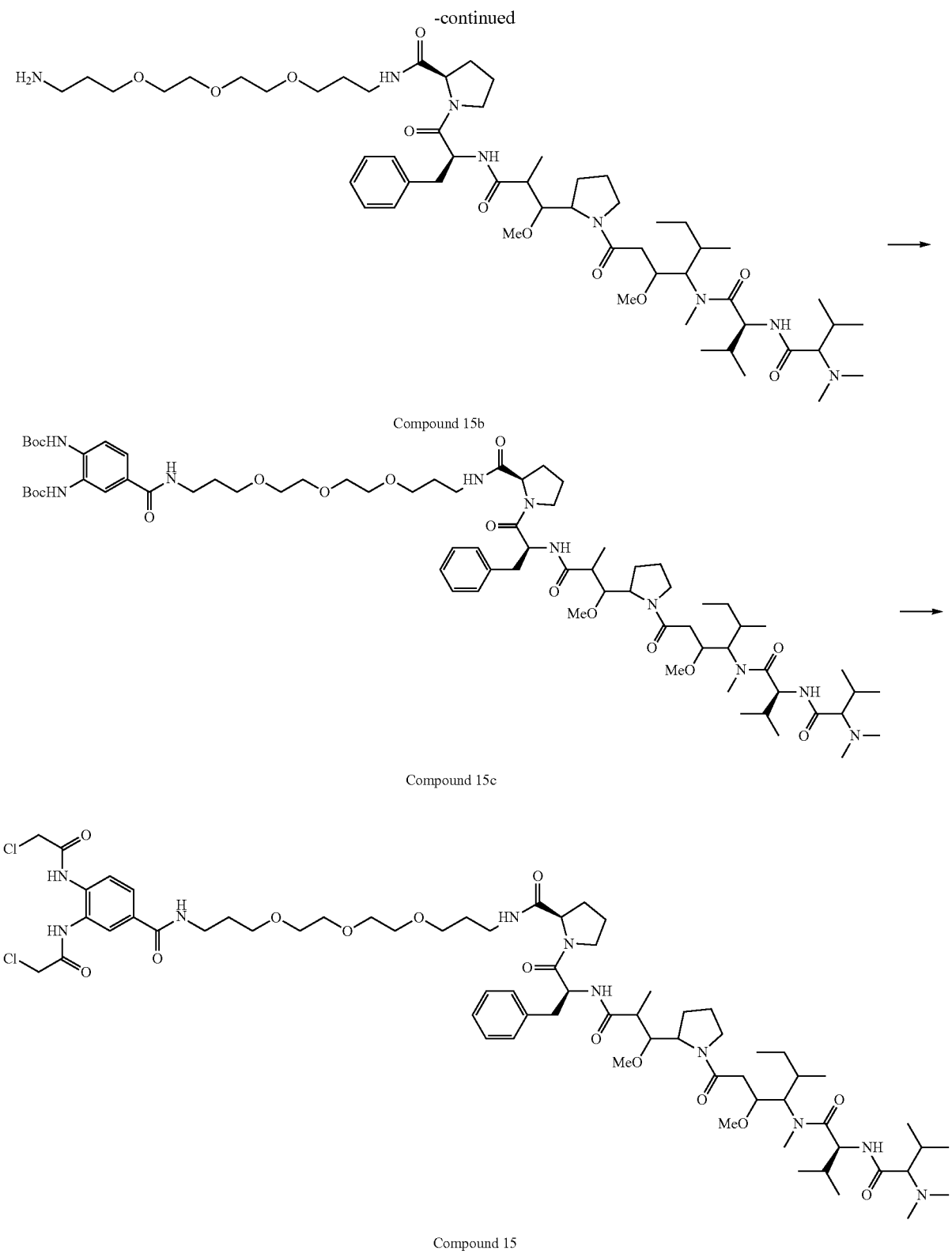
Step 1: Synthesis of Compound 15a
To a solution of Proline-AF (51.3 mg, 0.06 mmole) in DCM 6 mL and compound N-Boc-1,6-hexanediamine, CAS: 194920-62-2 (22.4 mg, 0.07 mmole) in 2 mL DCM, HATU (34.2 mg, 0.09 mmole) and DIPEA (19.3 mg, 0.15 mmole) were added. The reaction was gone completion after 4 hours. Solvent was removed under a reduced pressure. Inertsil ODS-3 column 30×250 mm, flow rate 31 mL/min, mobile phase from AcN 35% (0-5 min) 43% (5-21 min)

100% (21 min-), 0.1% TFA, UV 220 nm, Compound 15a, RT 13.6 min). The entitled Compound 15a was obtained as a white solid 52 mg, yield 74.6%. ESI, positive ion: M/Z: 1146.7 [M+1]$^+$, 1169.0 [M+Na]$^+$.

Step 2: Synthesis of Compound 15b

To a solution of the Compound 15a (52 mg, 0.05 mmole) in DCM (4 mL) was added TFA (2 mL). The mixture was stirred for 1 hour at RT, after which time the solvents were removed in vacuo. The crude product of Compound 15b was used without further purification. ESI, positive ion: M/Z: 1046.9 [M+1]$^+$, 1069.0 [M+Na]$^+$.

Step 3: Synthesis of Compound 15c

To a mixture solution of N-Boc-3,4-Diaminobenzoic acid (16 mg, 0.04 mmole) and pentafluorophenol (12.5 mg; 0.06 mmol) in DCM (18 mL) was added DCC (12.3 mg, 0.06 mmole). The mixture was stirred at room temperature for 12 hours, the precipitate was filtered and concentrated in vacuo. The column was eluted with n-Hexane/EtOAc (4:1). The fractions containing the target compound were collected and concentrated under reduced pressure to produce N-Boc-3,4-Diaminobenzoic acid PFP ester.

To a solution of N-Boc-3,4-Diaminobenzoic acid PFP ester was added Compound 15b (47.4 mg, 0.03 mmole) in 2 mL DMF, and DIPEA (29.3 mg, 0.23 mmole) were added. The reaction was gone completion after 2 hours. Solvent was removed under a reduced pressure. Inertsil ODS-3 column 30×250 mm, 10 CAN 43% (0-5 min) 50% (5-10 min) 55% (10-15 min) 65% (15-20 min) 100% (20 min-), flow rate 32 mL/min, UV 220, T69-3, RT 13.9 min). The entitled Compound 15c (28.9 mg, 0.022 mmole, yield 50%) was obtained as a white solid. ESI (positive ion): 1380.9 [M+1]$^+$, 1403.2 [M+Na]$^+$.

Step 4: Synthesis of Linker-Drug 15

To a solution Compound 15c (8.6 mg, 6 mole) in 4 mL DCM at 20-23° C. were added dropwise trifloroacetic acid 2 mL (10.4 mmole). The water bath was removed and stirring was continued for 2 hours. The solvent was removed under reduced pressure, the residue was added 2 mL methanol and stirred for 5 mins then solvent was removed. A minimum of DIW (2 mL) was added and lyophilized to give the crude product of Compound 15c-deBoc (8.1 mg) as TFA salt. ESI (positive ion): 1277.0 [M+1]$^+$, 1298.9 [M+Na]$^+$.

To a solution of the TFA salt (8.1 mg, 6 mole) in DCM/DMF (1.2/0.5 mL) solution were added, with stirring at 0-5° C., trimethylamine (45 μL, 0.324 mole) in DCM (0.2 mL), followed by a solution of chloroacetyl chloride (21 mg, 0.185 mmole) in DCM (0.3 mL). The cooling bath was removed after 2 hours and stirring was continued at room temperature for 15 hours. The reaction was checked for completion by HPLC and the mixture was evaporated to dryness. Purification by RP-HPLC (the residue was diluted by 4 mL M.P. solvent, Inertsil ODS-3 column 30×250 mm, 10 μm; flow rate 31 mL/min, M.P. from CAN 35% (0-5 min) 43% (5-15 min) 100% (15 min-), with 0.1% TFA, UV 220 nm) and the product-containing fraction (retention time=11.45 min) were lyophilized to give the Compound 15, i.e. Linker-drug 15 (6 mg, 4.5 mole, 75% yield). ESI, positive ion: M/Z: 1333.0 [M+H]$^+$, 1355.0 [M+Na]$^+$.

Example 16: Preparation of Linker-Drug 16

Linker-drug 16 was synthesized according to the procedures shown in the following scheme.

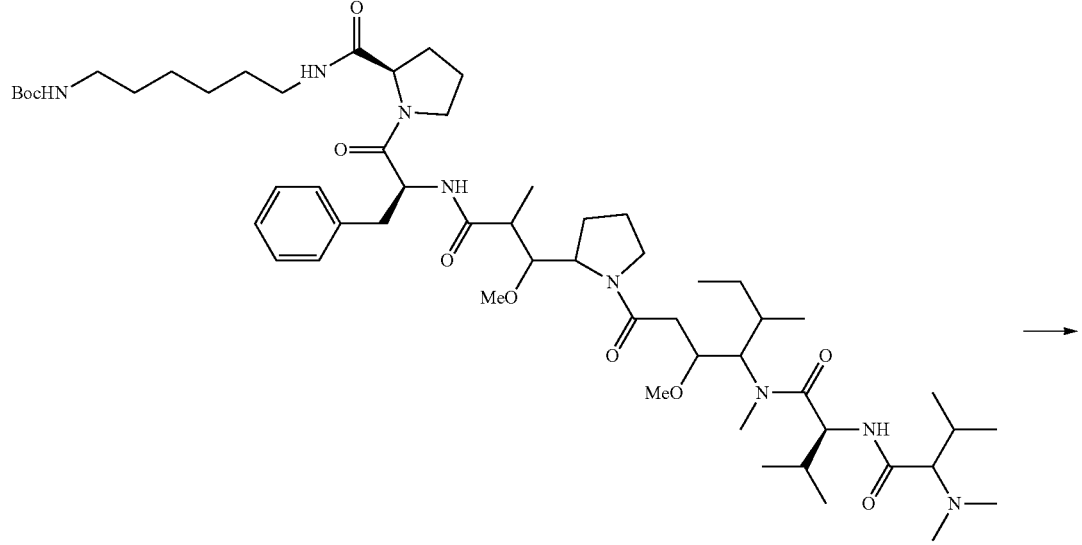

Compound 16a

-continued
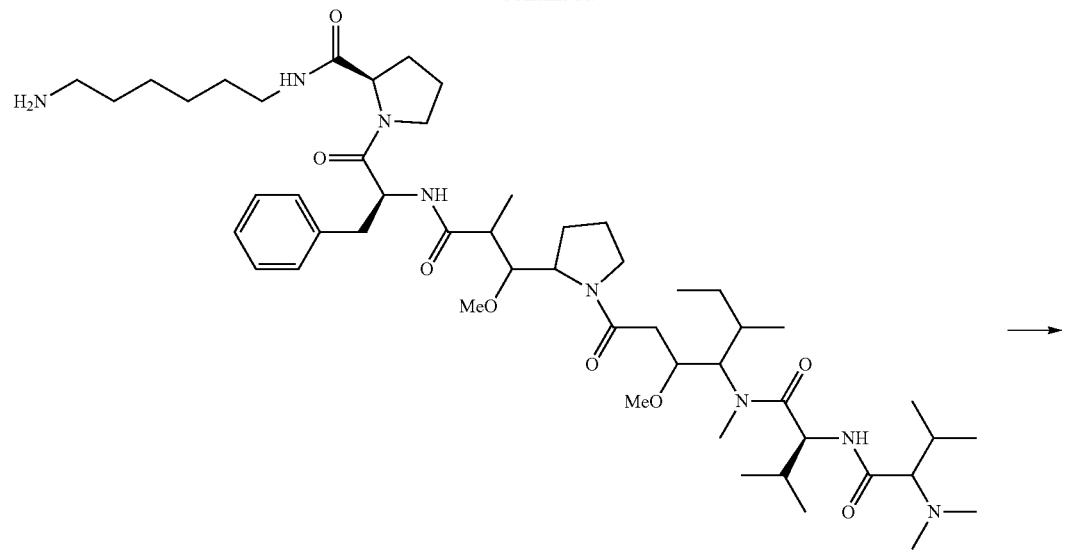
Compound 16b
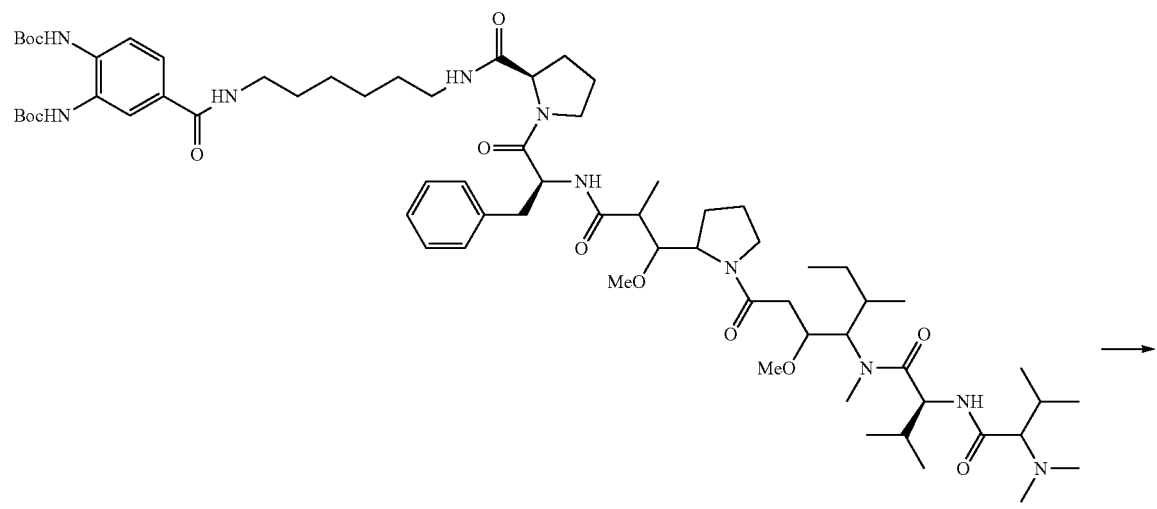
Compound 16c

-continued

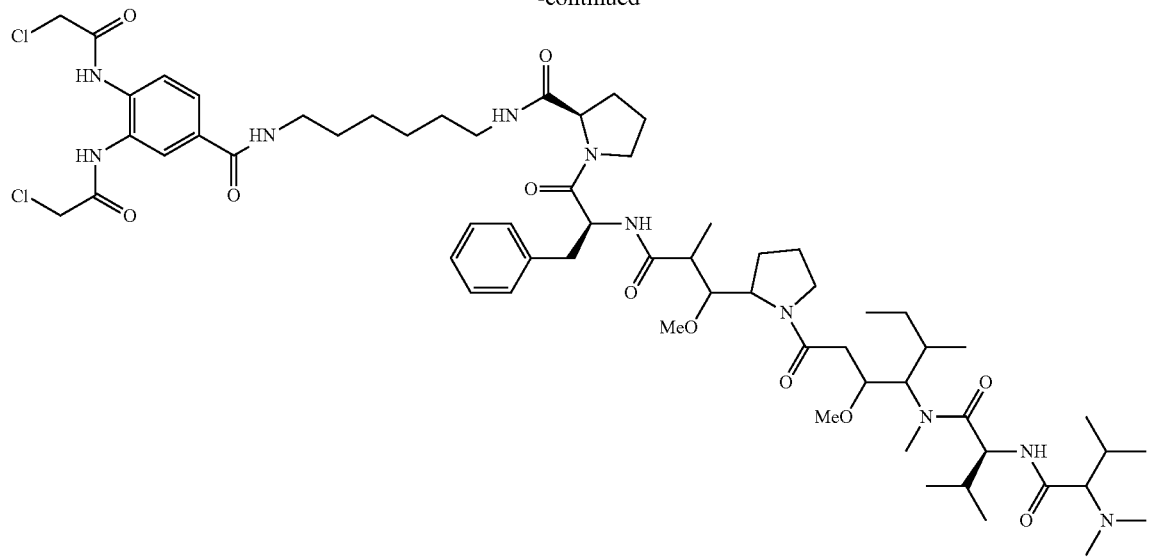

Compound 16

Step 1: Synthesis of Compound 16a

To a solution of Proline-Auristatin F (117 mg, 0.14 mmole) in 8 mL DCM and N-Boc-1,6-hexanediamine (45 mg, 0.21 mmole), HATU (80 mg, 0.21 mmole) and DIPEA (45 mg, 0.35 mmole) were added. The reaction was gone completion after 1 hour. Solvent was removed under a reduced pressure. Inertsil ODS-3 column 30×250 mm, flow rate 31 mL/min, mobile phase AcN 43% (0-10 min) 50% (10-17 min) 100% (17 min-), 0.1% TFA, UV 220 nm, Compound 16a, RT 14.4 min). The entitled Compound 16a was obtained as a white solid 137.8 mg, yield 95%. ESI, positive ion: M/Z: 1042.4 $[M+H]^+$, 1064.9 $[M+Na]^+$.

Step 2: Synthesis of Compound 16b

To a solution of the Compound 16a (137.8 mg, 0.13 mmole) in DCM (4 mL) was added TFA (2 mL). The mixture was stirred for 1 hour at RT, after which time the solvents were removed in vacuo. The crude product of Compound 16b was used without further purification. ESI, positive ion: M/Z: 942.6 $[M+H]^+$, 964.8 $[M+Na]^+$.

Step 3: Synthesis of Compound 16c

To a mixture solution of N-Boc-3,4-Diaminobenzoic acid (12.7 mg, 0.03 mmole) and pentafluorophenol (10 mg; 0.05 mmol) in DCM (6 mL) was added DCC (11.1 mg, 0.05 mmole). The mixture was stirred at room temperature for 12 hours, the precipitate was filtered and concentrated in vacuo. To a solution of PFP ester was added Compound 16b (33.9 mg, 0.03 mmole) and DIPEA (27.3 mg, 0.18 mmole) were added. The reaction was left for 1 hour at RT. After the removal of solvent, Compound 16c was purified by preparative HPLC (Inertsil ODS-3 column, size 30×250 mm, flow rate 31 mL/min, mobile phase: AcN 43% (0-5 min), 50% (5-10 min), 55% (10-20 min), 100% (20 min-), water with 0.1% TFA, UV 220 nm, Compound 16c, RT 15.2 min). The entitled Compound 16c was obtained as a white solid (32 mg, 70%). ESI, positive ion: M/Z: 1277.0 $[M+H]^+$, 1299.0 $[M+Na]^+$.

Step 4: Synthesis of Linker-Drug 16

To a solution of Compound 16c (7.5 mg, 5.8 mole) in 4 mL DCM at 20-23° C. water bath were added dropwise trifloroacetic acid 2 mL (10.4 mmole). The water bath was removed and stirring was continued for 2 hours. The solvent was removed under reduced pressure, the residue was added 2 mL methanol and stirred for 5 mins then solvent was removed. A minimum of water (2 mL) was added and lyophilized to give the crude product Compound 16c-deBoc as TFA salt, ESI for positive ion, M/Z: 1077.0 $[M+H]^+$, 1098.9 $[M+Na]^+$.

To a solution of the TFA salt (7 mg, 5.8 mole) in DCM/DMF (1.0/0.5 mL) solution were added, with stirring at 0-5° C., trimethylamine (40 μL, 0.288 mmole) in DCM (0.2 mL), followed by a solution of chloroacetyl chloride 18 mg (0.159 mmole) in DCM (0.3 mL). The cooling bath was removed after 2 hours and stirring was continued at RT for 15 hours. The reaction was checked for completion by HPLC and the mixture was evaporated to dryness. Purification by RP-HPLC (the residue was diluted by 3.5 mL M.P. solvent, Inertsil ODS-3 column 30×250 mm, 10 μm; flow rate 31 mL/min, M.P. from 35% gradient to 43% AcN/$H_2O$ with 0.1% TFA, UV220 nm) and the product-containing fraction (retention time is 12.27 min) were lyophilized to give the Compound 16, i.e. Linker-drug 16 (5 mg, 4.1 mole, 70% yield). ESI, positive ion: M/Z: $[M+H]^+$=1228.9, 1250.9 $[M+Na]^+$.

<Reduction of Antibody>

Herceptin was treated with 2.0-5.5 molar equivalent of TCEP at 37° C. for 2 hours for reduction. After desalting, the thiol concentration of Herceptin was determined by DTNB and the protein concentration was measured by UV 280 nm to calculate the number of SH/IgG. The band profile of the reduced Herceptin was obtained by CE. It was determined that 4 pairs of interchain disulfide bonds could be reduced by 4.5-5.0 molar equivalent of TCEP to obtain 8 free thiols.

<Antibody-Drug Conjugate (ADC)>

Capillary electrophoresis (CE) and hydrophobic interaction chromatography (HIC) were respectively used to determine the degree of cross-linking and average drug-to-antibody ratio (DAR).

HIC (Hydrophobic Interaction Chromatography) Analysis

An Agilent HPLC with the Butyl NPR (4.6×35 mm) TOSOH column was used to analyze the drug-to-antibody ratio (DAR) profile. The mobile phase A consisted of 25 mM sodium phosphate, 1.5 M ammonium sulfate, pH 6.95, and mobile phase B consisted of 25 mM sodium phosphate, 25% isopropanol, pH 6.95. 10 µL of samples were injected into the column at a flow rate of 0.8 mL/min and separated under gradient mode in 20 minutes (Table 2). Absorbance was detected at 280 nm.

TABLE 2

| Time (min) | mobile phase A: 25 mM NaH$_2$PO$_4$, 1.5M (NH$_4$)$_2$SO$_4$, pH 6.95 | mobile phase B: 25 mM NaH$_2$PO$_4$, 25% IPA, pH 6.95 |
| --- | --- | --- |
| 0 | 95 | 5 |
| 15 | 30 | 70 |
| 17 | 0 | 100 |
| 17.1 | 95 | 5 |
| 20 | 95 | 5 |

Example 17: Herceptin-Linker-Drug 1

Frozen crystal of antibody Herceptin (bought from Roche) was dissolved in DIW (initial concentration: 11.36 mg/mL). 40 µL of the antibody solution was treated with 0.77 µL of TCEP (5 molar equivalent) and stirred at 37° C. for 2 hours. A desalting column was used to remove extra TCEP in the reduced Herceptin and the buffer was changed to borate buffer. 2.618 µL (17 molar equivalent) of 20 mM of Linker-drug 1 prepared in DMSO was added into the antibody solution at 25-40° C. for 2 hours (final concentration of organic solvent in the mixture solution was about 4.9%) to obtain the antibody-drug conjugate (ADC). A desalting column (ThermoFisher Scientific, MWCO: 40K) was used to purify the product ADC Herceptin-Linker-drug 1. During elution, the buffer was changed to PBS buffer (2.67 mM KCl, 1.47 mM KH$_2$PO$_4$, 137.93 mM NaCl, 8.06 mM Na$_2$HPO$_4$-7H$_2$O).

FIG. 1 shows that the average DAR of Herceptin-Linker-drug 1 is about 3.9, and the D4 ratio is about 65%.

Example 18: Herceptin-Linker-Drug 2

Frozen crystal of antibody Herceptin (bought from Roche) was dissolved in DIW (initial concentration: 11.36 mg/mL). 40 µL of the antibody solution was treated with 3.07 µL of TCEP (5 molar equivalent) and stirred at 37° C. for 2 hours. A desalting column was used to remove extra TCEP in the reduced Herceptin and the buffer was changed to borate buffer. 2.8 µL of DMSO was added and mixed evenly. Then, 1.386 µL (9 molar equivalent) of 20 mM of Linker-drug 2 prepared in DMSO was added into the antibody solution at 0-4° C. for 24 hours (final concentration of organic solvent in the mixture solution was about 7.6%) to obtain the antibody-drug conjugate (ADC). A desalting column (ThermoFisher Scientific, MWCO: 40K) was used to purify the product ADC Herceptin-Linker-drug 2. During elution, the buffer was changed to PBS buffer (2.67 mM KCl, 1.47 mM KH$_2$PO$_4$, 137.93 mM NaCl, 8.06 mM Na$_2$HPO$_4$-7H$_2$O).

FIG. 1 shows that the average DAR of Herceptin-Linker-drug 2 is about 4.3, and the D4 ratio is about 60%.

Example 19: Herceptin-Linker-Drug 3

Frozen crystal of antibody Herceptin (bought from Roche) was dissolved in DIW (initial concentration: 11.36 mg/mL). 40 µL of the antibody solution was treated with 3.07 µL of TCEP (5 molar equivalent) and stirred at 37° C. for 2 hours. A desalting column was used to remove extra TCEP in the reduced Herceptin and the buffer was changed to borate buffer. 3.234 µL (21 molar equivalent) of 20 mM of Linker-drug 3 prepared in DMSO was added into the antibody solution at 0-4° C. for 24 hours (final concentration of organic solvent in the mixture solution was about 5.9%) to obtain the antibody-drug conjugate (ADC). A desalting column (ThermoFisher Scientific, MWCO: 40K) was used to purify the product ADC Herceptin-Linker-drug 3. During elution, the buffer was changed to PBS buffer (2.67 mM KI, 1.47 mM KH$_2$PO$_4$, 137.93 mM NaCl, 8.06 mM Na$_2$HPO$_4$-7H$_2$O).

Figure 3:
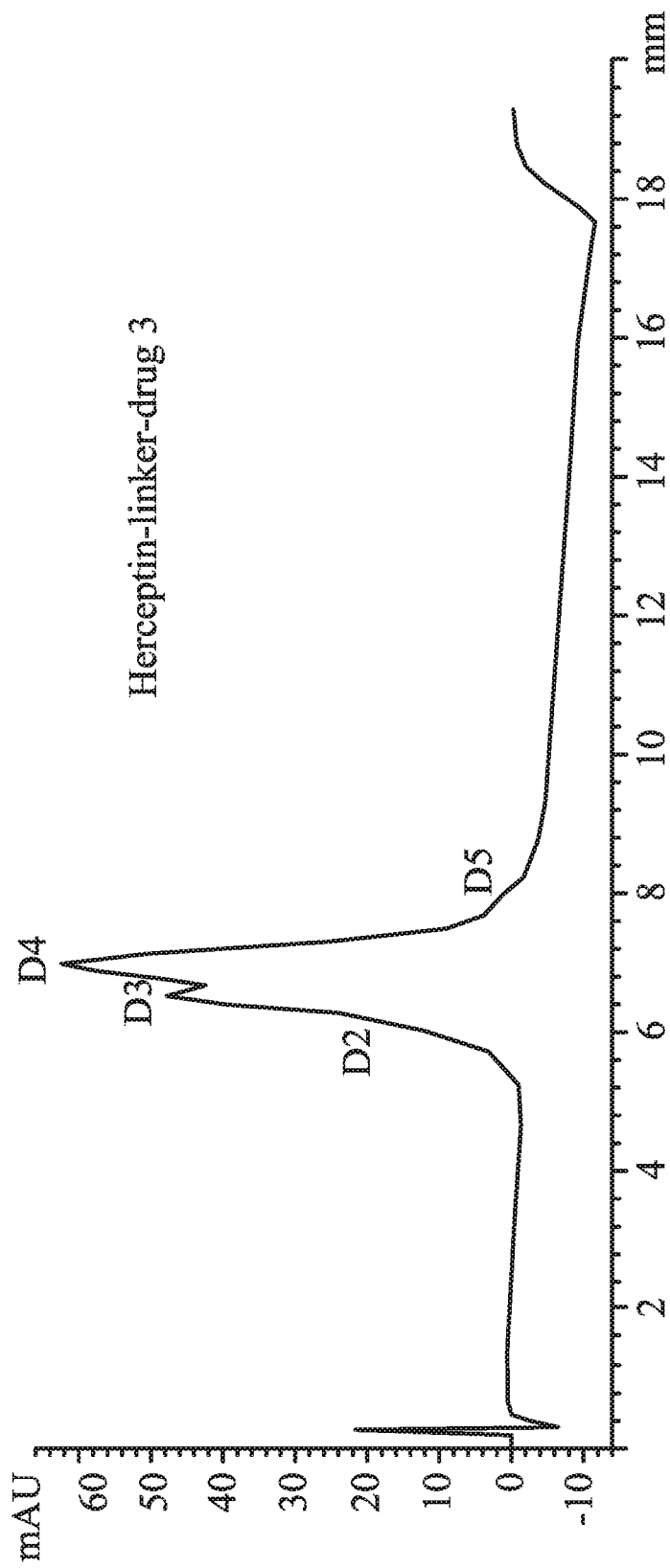
FIG. 3 shows a HIC profile of Herceptin-Linker-drug 3 in accordance with one embodiment of the present disclosure.

FIG. 3 shows that the average DAR of Herceptin-Linker-drug 3 is about 3.6, and the D4 ratio is about 31%.

Example 20: Herceptin-Linker-Drug 5

Frozen crystal of antibody Herceptin (bought from Roche) was dissolved in DIW (initial concentration: 11.36 mg/mL). 40 µL of the antibody solution was treated with 3.07 µL of TCEP (5 molar equivalent) and stirred at 37° C. for 2 hours. A desalting column was used to remove extra TCEP in the reduced Herceptin and the buffer was changed to borate buffer. 1.386 µL (9 molar equivalent) of 20 mM of Linker-drug 5 prepared in DMSO was added into the antibody solution at 0-4° C. for 24 hours (final concentration of organic solvent in the mixture solution was about 2.7%) to obtain the antibody-drug conjugate (ADC). A desalting column (ThermoFisher Scientific, MWCO: 40K) was used to purify the product ADC Herceptin-Linker-drug 5. During elution, the buffer was changed to PBS buffer (2.67 mM KCl, 1.47 mM KH$_2$PO$_4$, 137.93 mM NaCl, 8.06 mM Na$_2$HPO$_4$-7H$_2$O).

Figure 4:
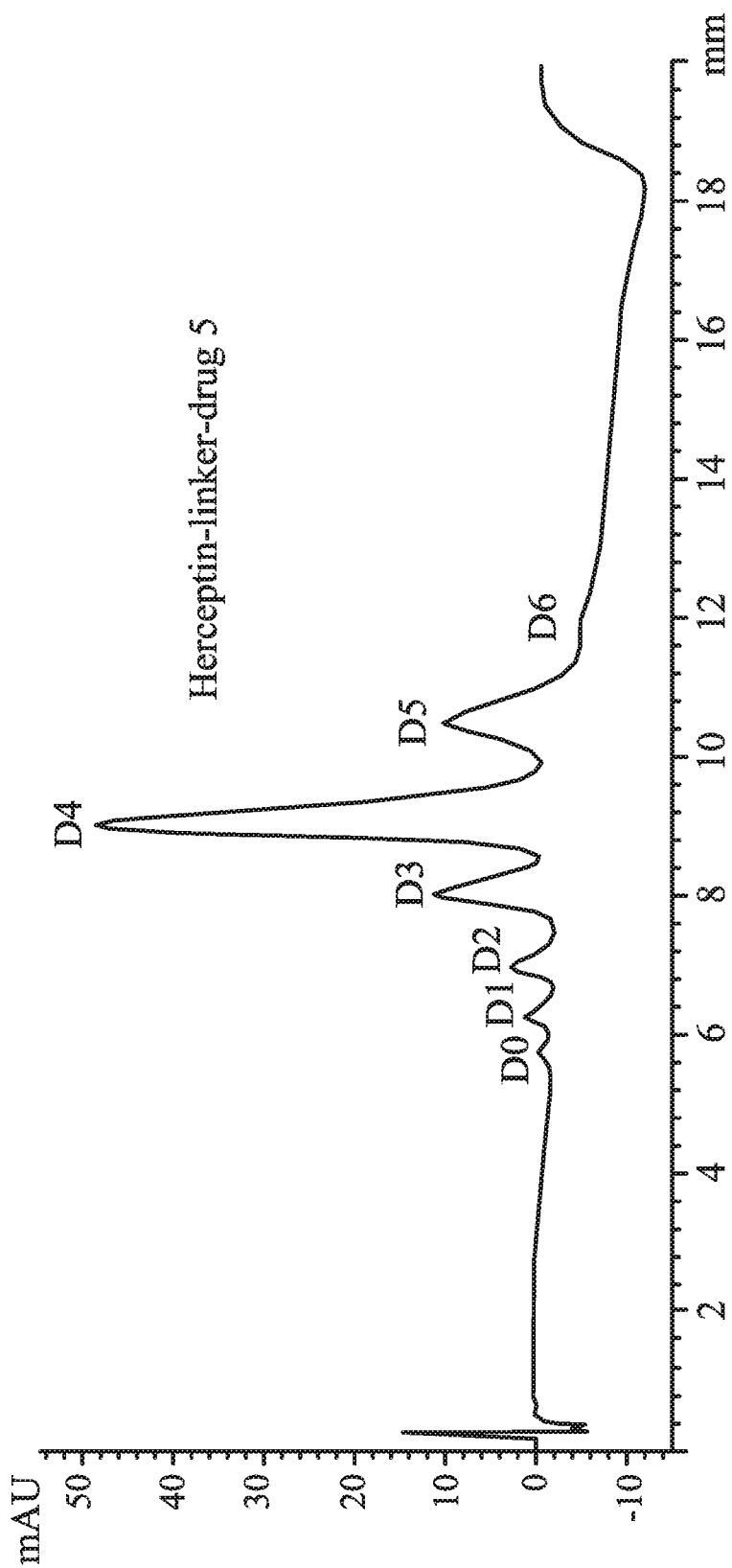
FIG. 4 shows a HIC profile of Herceptin-Linker-drug 5 in accordance with one embodiment of the present disclosure.

FIG. 4 shows that the average DAR of Herceptin-Linker-drug 5 is about 4.0, and the D4 ratio is about 54%.

Example 21: Herceptin-Linker-Drug 7

Frozen crystal of antibody Herceptin (bought from Roche) was dissolved in DIW (initial concentration: 11.36 mg/mL). 40 µL of the antibody solution was treated with 3.07 µL of TCEP (5 molar equivalent) and stirred at 37° C. for 2 hours. A desalting column was used to remove extra TCEP in the reduced Herceptin and the buffer was changed to borate buffer. 9.9 µL of DMSO was added and mixed evenly. Then, 1.694 µL (11 molar equivalent) of 20 mM of Linker-drug 7 prepared in DMSO was added into the antibody solution at 0-4° C. for 24 hours (final concentration of organic solvent in the mixture solution was about 18.3%) to obtain the antibody-drug conjugate (ADC). A desalting column (ThermoFisher Scientific, MWCO: 40K) was used to purify the product ADC Herceptin-Linker-drug 7. During elution, the buffer was changed to PBS buffer (2.67 mM KCl, 1.47 mM KH$_2$PO$_4$, 137.93 mM NaCl, 8.06 mM Na$_2$HPO$_4$-7H$_2$O).

Figure 5:
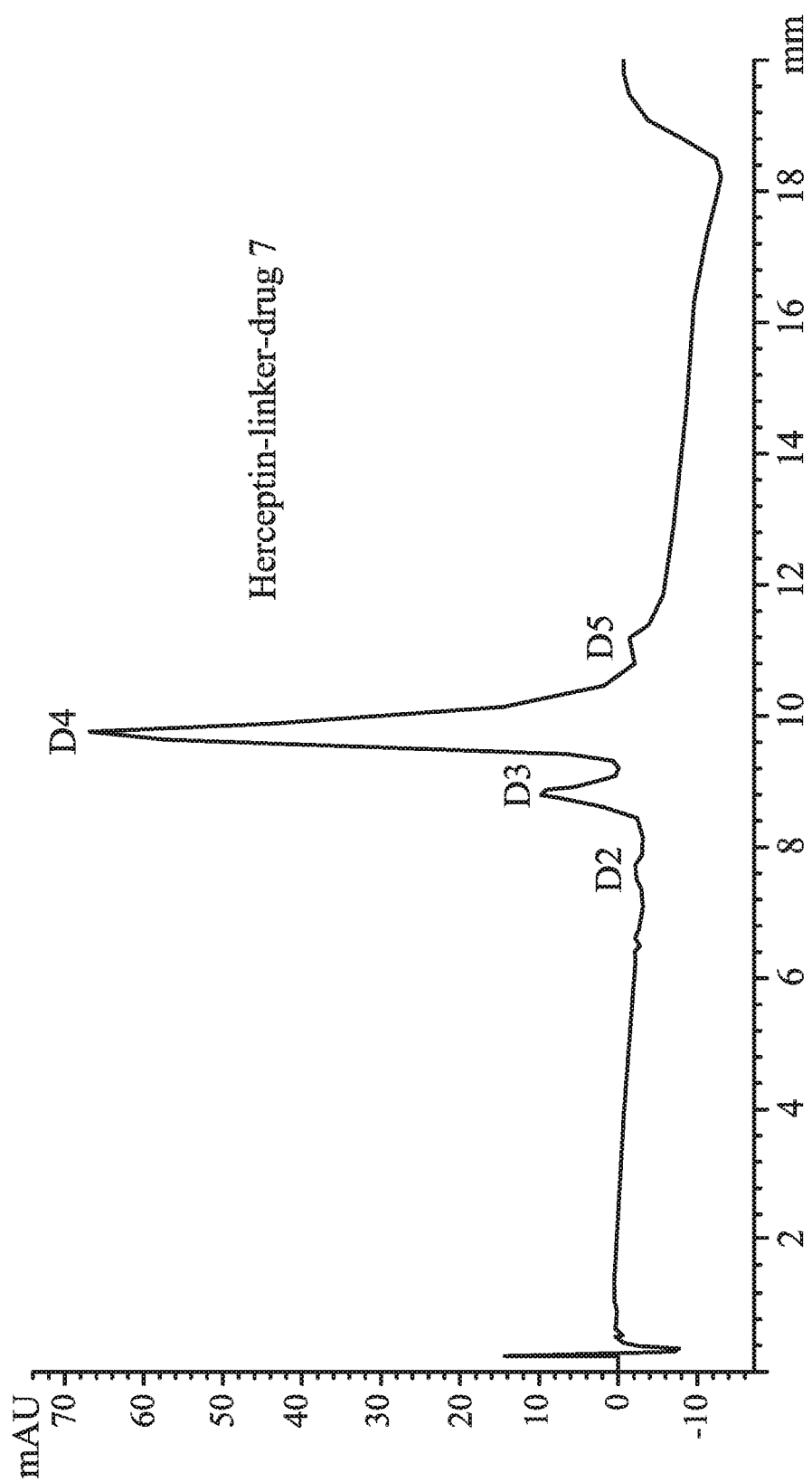
FIG. 5 shows a HIC profile of Herceptin-Linker-drug 7 in accordance with one embodiment of the present disclosure.

FIG. 5 shows that the average DAR of Herceptin-Linker-drug 7 is about 3.9, and the D4 ratio is about 77%.

Example 22: Herceptin-Linker-Drug 8

Frozen crystal of antibody Herceptin (bought from Roche) was dissolved in DIW (initial concentration: 11.36 mg/mL). 440 µL of the antibody solution was treated with 33.78 µL of TCEP (5 molar equivalent) and stirred at 37° C. for 2 hours. A desalting column was used to remove extra TCEP in the reduced Herceptin and the buffer was changed to borate buffer. 76.1 μL of DMSO was added and mixed evenly. Then, 15.25 μL (9 molar equivalent) of 20 mM of Linker-drug 8 prepared in DMSO was added into the antibody solution at 25-40° C. for 2 hours (final concentration of organic solvent in the mixture solution was about 12.8%) to obtain the antibody-drug conjugate (ADC). A desalting column (ThermoFisher Scientific, MWCO: 40K) was used to purify the product ADC Herceptin-Linker-drug 8. During elution, the buffer was changed to PBS buffer (2.67 mM KCl, 1.47 mM $KH_2PO_4$, 137.93 mM NaCl, 8.06 mM $Na_2HPO_4$-$7H_2O$).

Figure 6:
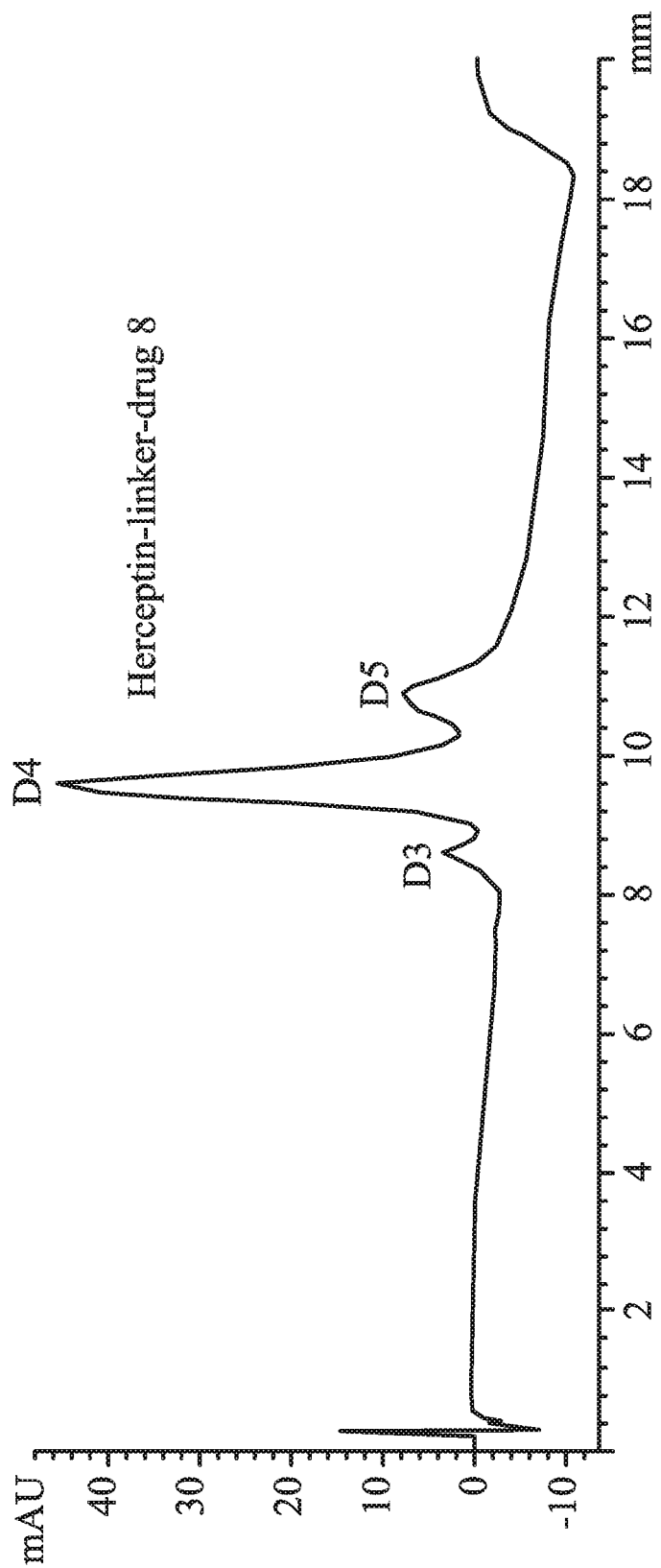
FIG. 6 shows a HIC profile of Herceptin-Linker-drug 8 in accordance with one embodiment of the present disclosure.

FIG. 6 shows that the average DAR of Herceptin-Linker-drug 8 is about 4.2, and the D4 ratio is about 65%.

Example 23: Herceptin-Linker-Drug 9

Frozen crystal of antibody Herceptin (bought from Roche) was dissolved in DIW (initial concentration: 11.36 mg/mL). 40 μL of the antibody solution was treated with 3.07 μL of TCEP (5 molar equivalent) and stirred at 37° C. for 2 hours. A desalting column was used to remove extra TCEP in the reduced Herceptin and the buffer was changed to borate buffer. 12.5 μL of DMSO was added and mixed evenly. Then, 0.924 μL (6 molar equivalent) of 20 mM of Linker-drug 9 prepared in DMSO was added into the antibody solution at 25-40° C. for 2 hours (final concentration of organic solvent in the mixture solution was about 28.9%) to obtain the antibody-drug conjugate (ADC). A desalting column (ThermoFisher Scientific, MWCO: 40K) was used to purify the product ADC Herceptin-Linker-drug 9. During elution, the buffer was changed to PBS buffer (2.67 mM KCl, 1.47 mM $KH_2PO_4$, 137.93 mM NaCl, 8.06 mM $Na_2HPO_4$-$7H_2O$).

Figure 7:
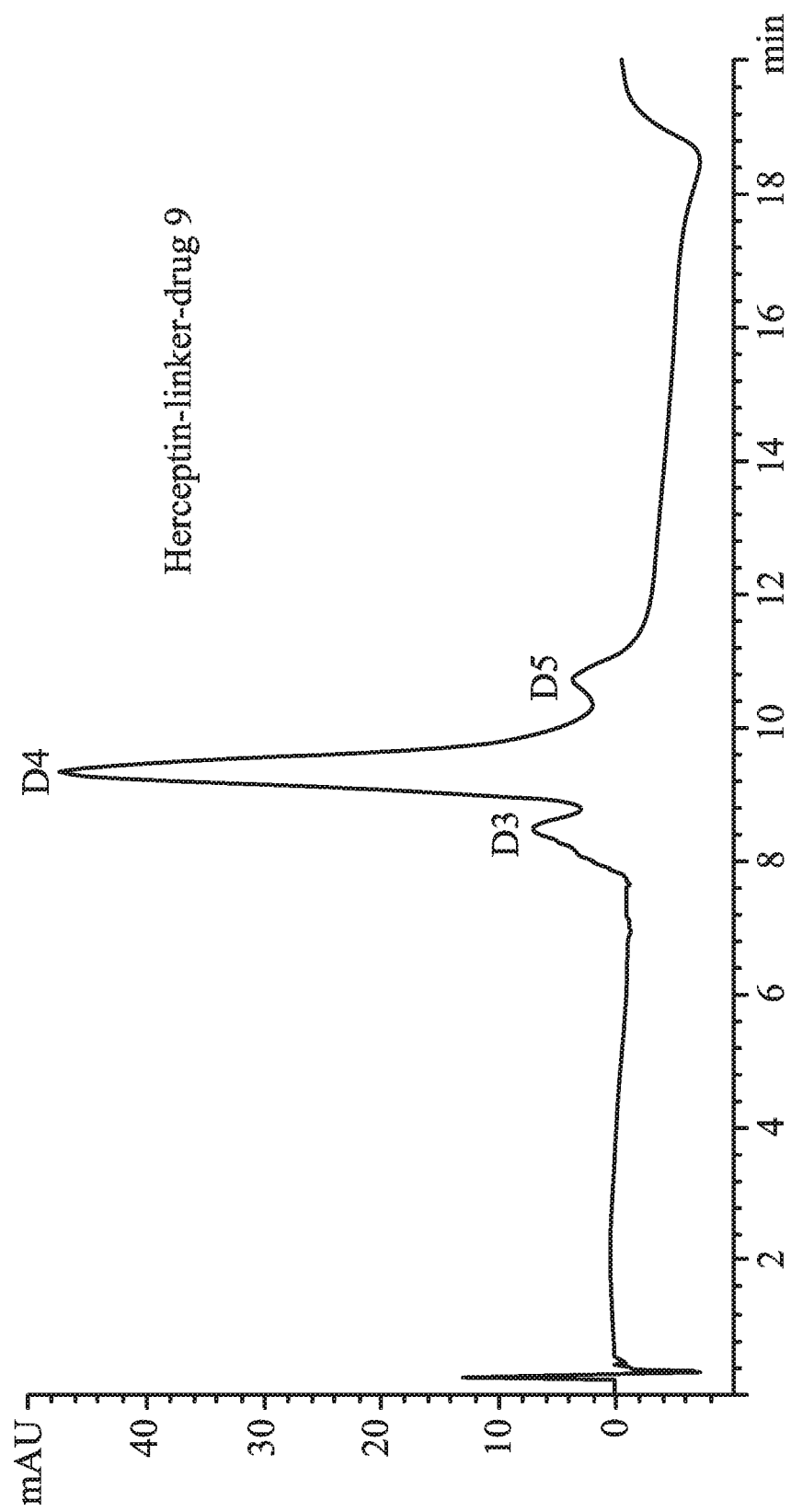
FIG. 7 shows a HIC profile of Herceptin-Linker-drug 9 in accordance with one embodiment of the present disclosure.

FIG. 7 shows that the average DAR of Herceptin-Linker-drug 9 is about 4.0, and the D4 ratio is about 70%.

Example 24: Herceptin-Linker-Drug 11

Frozen crystal of antibody Herceptin (bought from Roche) was dissolved in DIW (initial concentration: 11.36 mg/mL). 40 μL of the antibody solution was treated with 3.07 μL of TCEP (5 molar equivalent) and stirred at 37° C. for 2 hours. A desalting column was used to remove extra TCEP in the reduced Herceptin and the buffer was changed to borate buffer. 1.078 μL (7 molar equivalent) of 20 mM of Linker-drug 11 prepared in DMSO was added into the antibody solution at 0-4° C. for 2 hours (final concentration of organic solvent in the mixture solution was about 2.1%) to obtain the antibody-drug conjugate (ADC). A desalting column (ThermoFisher Scientific, MWCO: 40K) was used to purify the product ADC Herceptin-Linker-drug 11. During elution, the buffer was changed to PBS buffer (2.67 mM KCl, 1.47 mM $KH_2PO_4$, 137.93 mM NaCl, 8.06 mM $Na_2HPO_4$-$7H_2O$).

Figure 8:
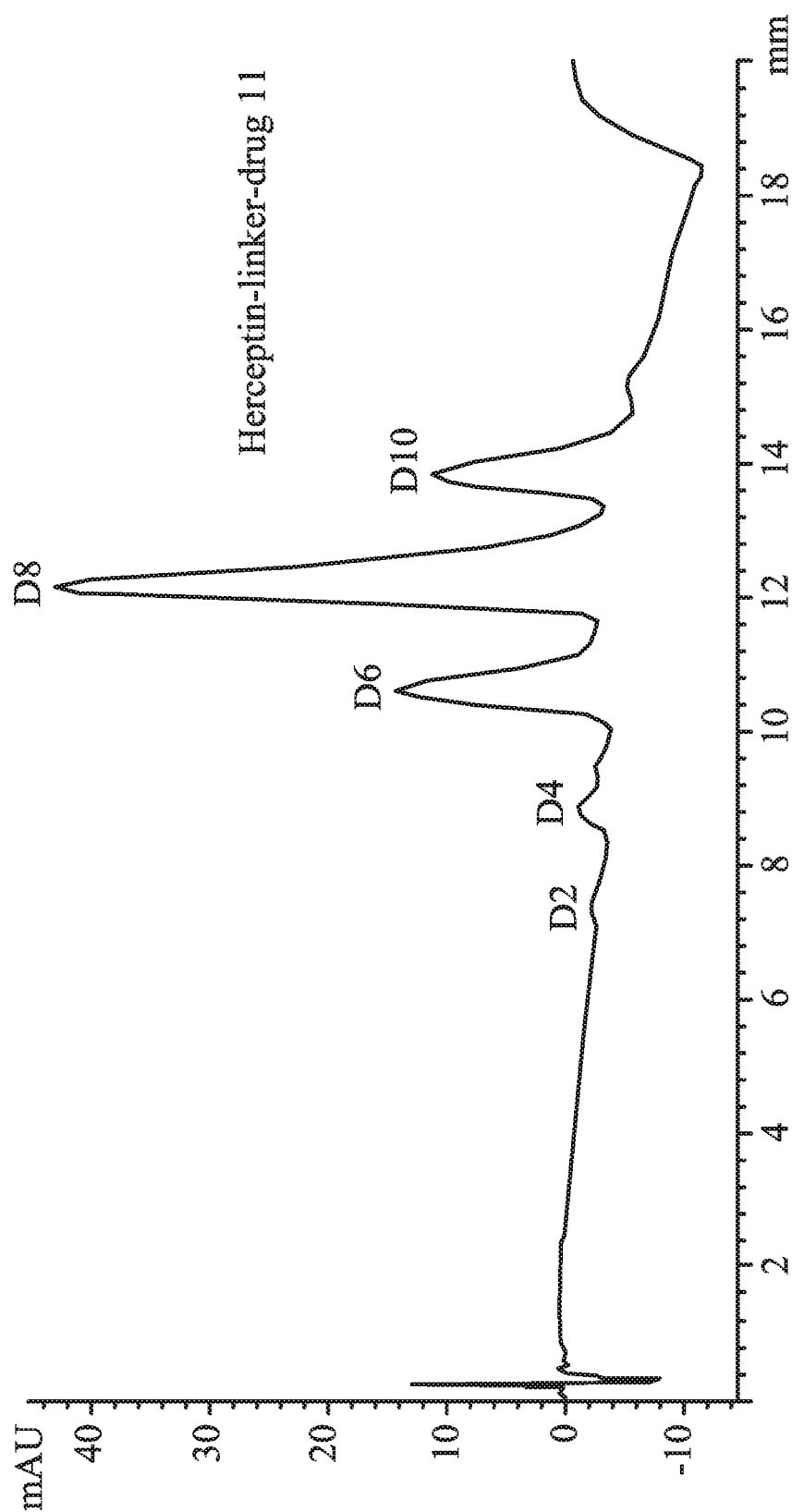
FIG. 8 shows a HIC profile of Herceptin-Linker-drug 11 in accordance with one embodiment of the present disclosure.

FIG. 8 shows that the average DAR of Herceptin-Linker-drug 11 is about 8.0, and the D8 ratio is about 53%. The linker unit of Herceptin-Linker-drug 11 conjugates 2 drug units. Therefore, the average DAR of Herceptin-Linker-drug 11 is twice more than other ADCs.

Example 25: Herceptin-Linker-Drug 12

Frozen crystal of antibody Herceptin (bought from Roche) was dissolved in DIW (initial concentration: 11.36 mg/mL). 40 μL of the antibody solution was treated with 3.07 μL of TCEP (5 molar equivalent) and stirred at 37° C. for 2 hours. A desalting column was used to remove extra TCEP in the reduced Herceptin and the buffer was changed to borate buffer. 2.615 μL (17 molar equivalent) of 20 mM of Linker-drug 12 prepared in DMSO was added into the antibody solution at 25-40° C. for 2 hours (final concentration of organic solvent in the mixture solution was about 4.9%) to obtain the antibody-drug conjugate (ADC). A desalting column (ThermoFisher Scientific, MWCO: 40K) was used to purify the product ADC Herceptin-Linker-drug 12. During elution, the buffer was changed to PBS buffer (2.67 mM KCl, 1.47 mM $KH_2PO_4$, 137.93 mM NaCl, 8.06 mM $Na_2HPO_4$-$7H_2O$).

Figure 9:
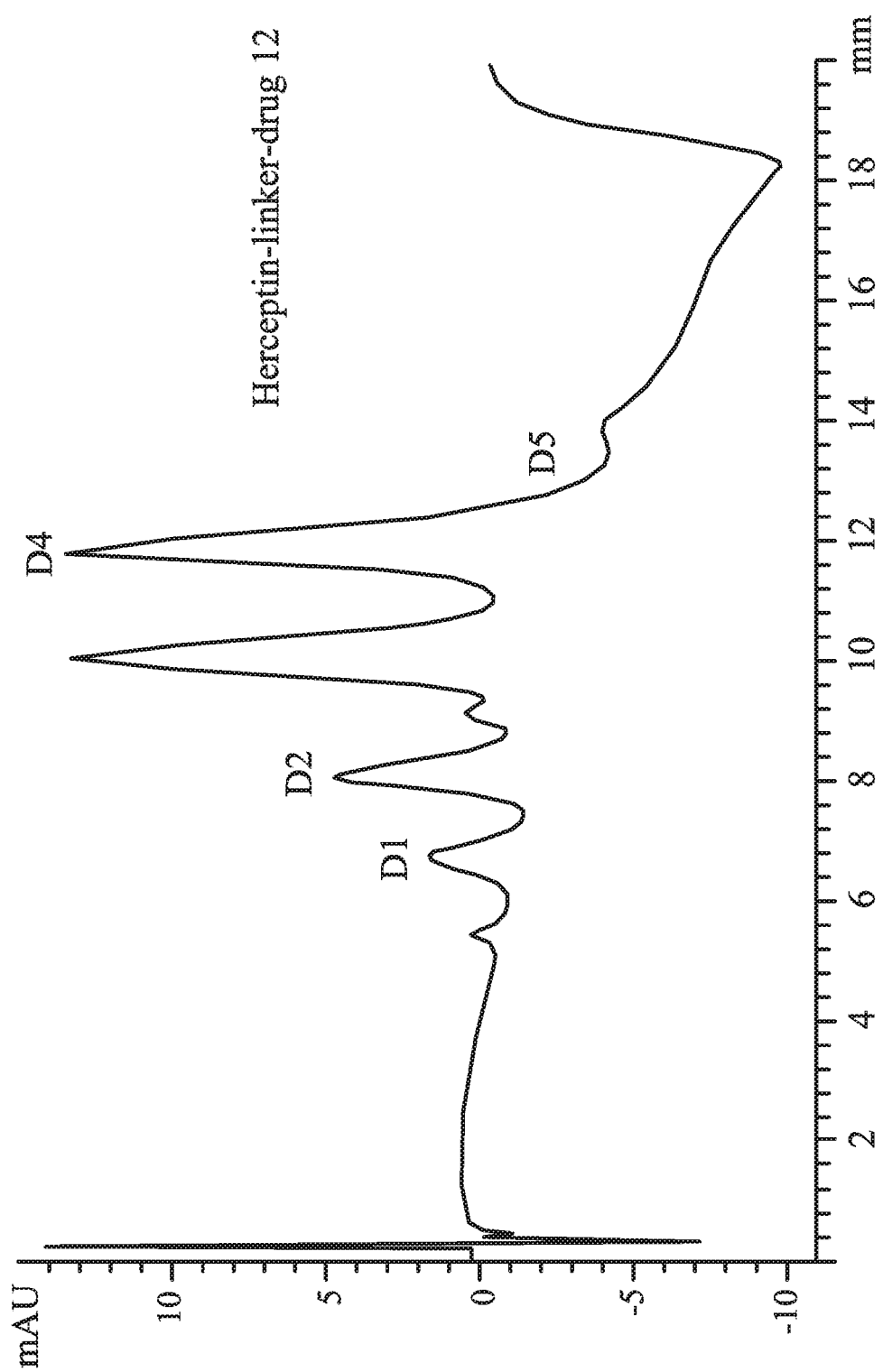
FIG. 9 shows a HIC profile of Herceptin-Linker-drug 12 in accordance with one embodiment of the present disclosure.

FIG. 9 shows that the average DAR of Herceptin-Linker-drug 12 is about 3.2, and the D4 ratio is about 38%.

Example 26: Herceptin-Linker-Drug 13

Frozen crystal of antibody Herceptin (bought from Roche) was dissolved in DIW (initial concentration: 11.36 mg/mL). 40 μL of the antibody solution was treated with 3.07 μL of TCEP (5 molar equivalent) and stirred at 37° C. for 2 hours. A desalting column was used to remove extra TCEP in the reduced Herceptin and the buffer was changed to borate buffer. 0.924 μL (6 molar equivalent) of 20 mM of Linker-drug 13 prepared in DMSO was added into the antibody solution at 25-40° C. for 2 hours (final concentration of organic solvent in the mixture solution was about 1.8%) to obtain the antibody-drug conjugate (ADC). A desalting column (ThermoFisher Scientific, MWCO: 40K) was used to purify the product ADC Herceptin-Linker-drug 13. During elution, the buffer was changed to PBS buffer (2.67 mM KCl, 1.47 mM $KH_2PO_4$, 137.93 mM NaCl, 8.06 mM $Na_2HPO_4$-$7H_2O$).

Figure 10:
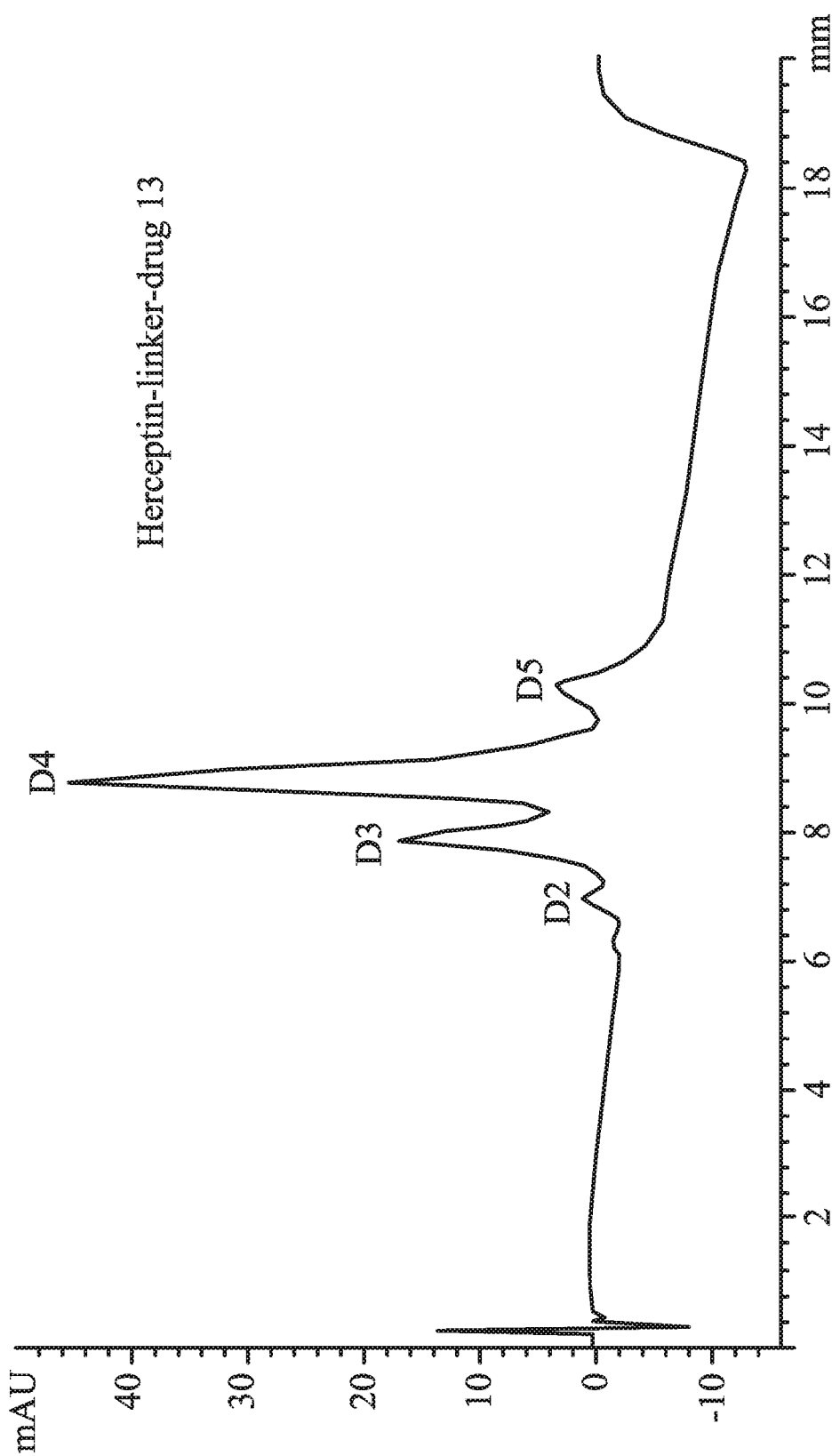
FIG. 10 shows a HIC profile of Herceptin-Linker-drug 13 in accordance with one embodiment of the present disclosure.

FIG. 10 shows that the average DAR of Herceptin-Linker-drug 13 is about 3.9, and the D4 ratio is about 58%.

Example 27: Herceptin-Linker-Drug 14

Frozen crystal of antibody Herceptin (bought from Roche) was dissolved in DIW (initial concentration: 11.36 mg/mL). 40 μL of the antibody solution was treated with 0.77 μL of TCEP (5 molar equivalent) and stirred at 37° C. for 2 hours. A desalting column was used to remove extra TCEP in the reduced Herceptin and the buffer was changed to borate buffer. 2.002 μL (13 molar equivalent) of 20 mM of Linker-drug 14 prepared in DMSO was added into the antibody solution at 0-4° C. for 24 hours (final concentration of organic solvent in the mixture solution was about 3.8%) to obtain the antibody-drug conjugate (ADC). A desalting column (ThermoFisher Scientific, MWCO: 40K) was used to purify the product ADC Herceptin-Linker-drug 14. During elution, the buffer was changed to PBS buffer (2.67 mM KCl, 1.47 mM $KH_2PO_4$, 137.93 mM NaCl, 8.06 mM $Na_2HPO_4$-$7H_2O$).

Figure 11:
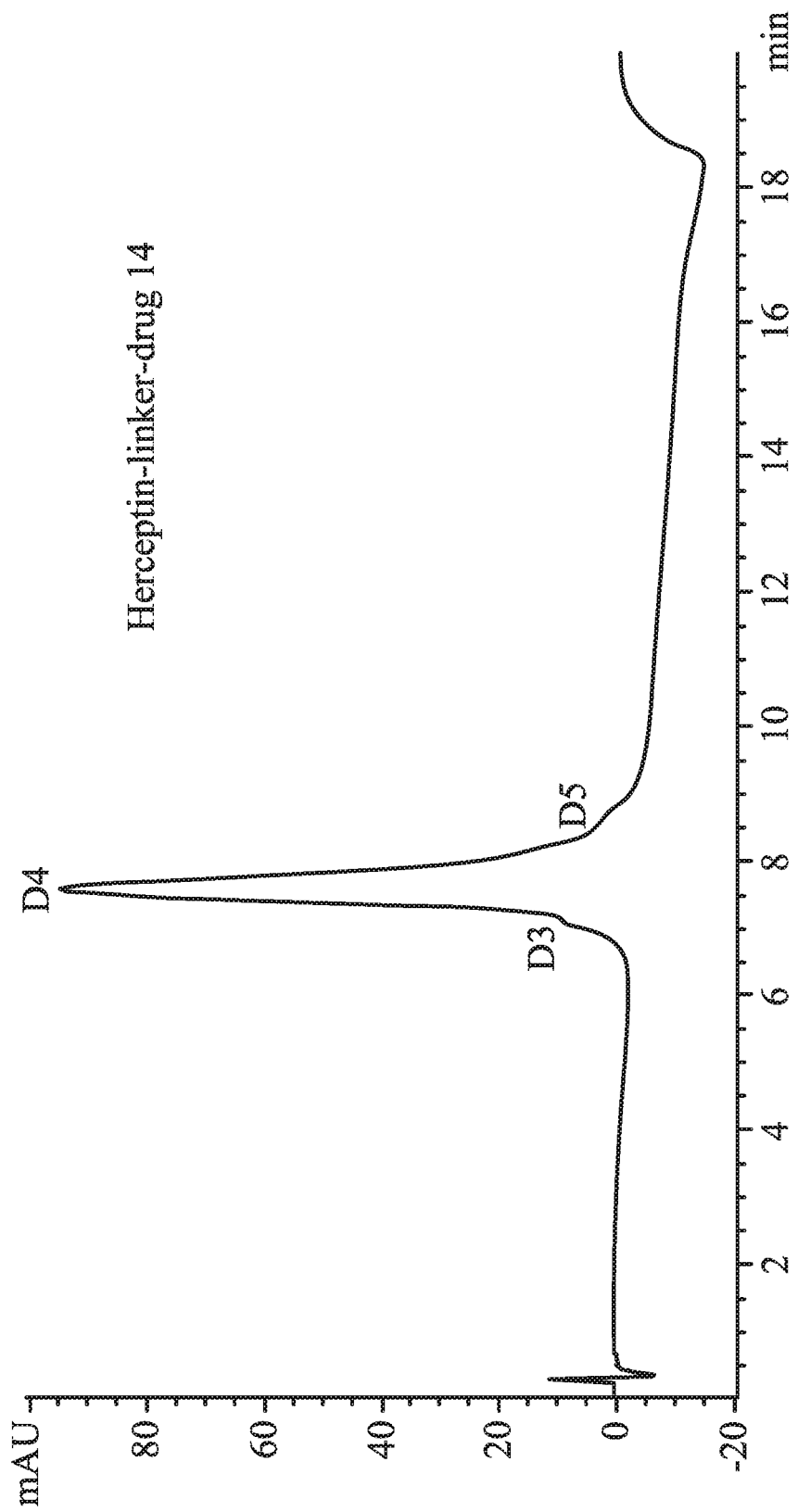
FIG. 11 shows a HIC profile of Herceptin-Linker-drug 14 in accordance with one embodiment of the present disclosure.

FIG. 11 shows that the average DAR of Herceptin-Linker-drug 14 is about 4.0, and the D4 ratio is about 87%.

Example 28: Herceptin-Linker-Drug 15

Frozen crystal of antibody Herceptin (bought from Roche) was dissolved in DIW (initial concentration: 11.36 mg/mL). 40 μL of the antibody solution was treated with 0.77 μL of TCEP (5 molar equivalent) and stirred at 37° C. for 2 hours. A desalting column was used to remove extra TCEP in the reduced Herceptin and the buffer was changed to borate buffer. 2.002 μL (13 molar equivalent) of 20 mM of Linker-drug 15 prepared in DMSO was added into the antibody solution at 0-4° C. for 24 hours (final concentration of organic solvent in the mixture solution was about 3.8%) to obtain the antibody-drug conjugate (ADC). A desalting column (ThermoFisher Scientific, MWCO: 40K) was used to purify the product ADC Herceptin-Linker-drug 15. During elution, the buffer was changed to PBS buffer (2.67 mM KCl, 1.47 mM $KH_2PO_4$, 137.93 mM NaCl, 8.06 mM $Na_2HPO_4\text{-}7H_2O$).

Figure 12:
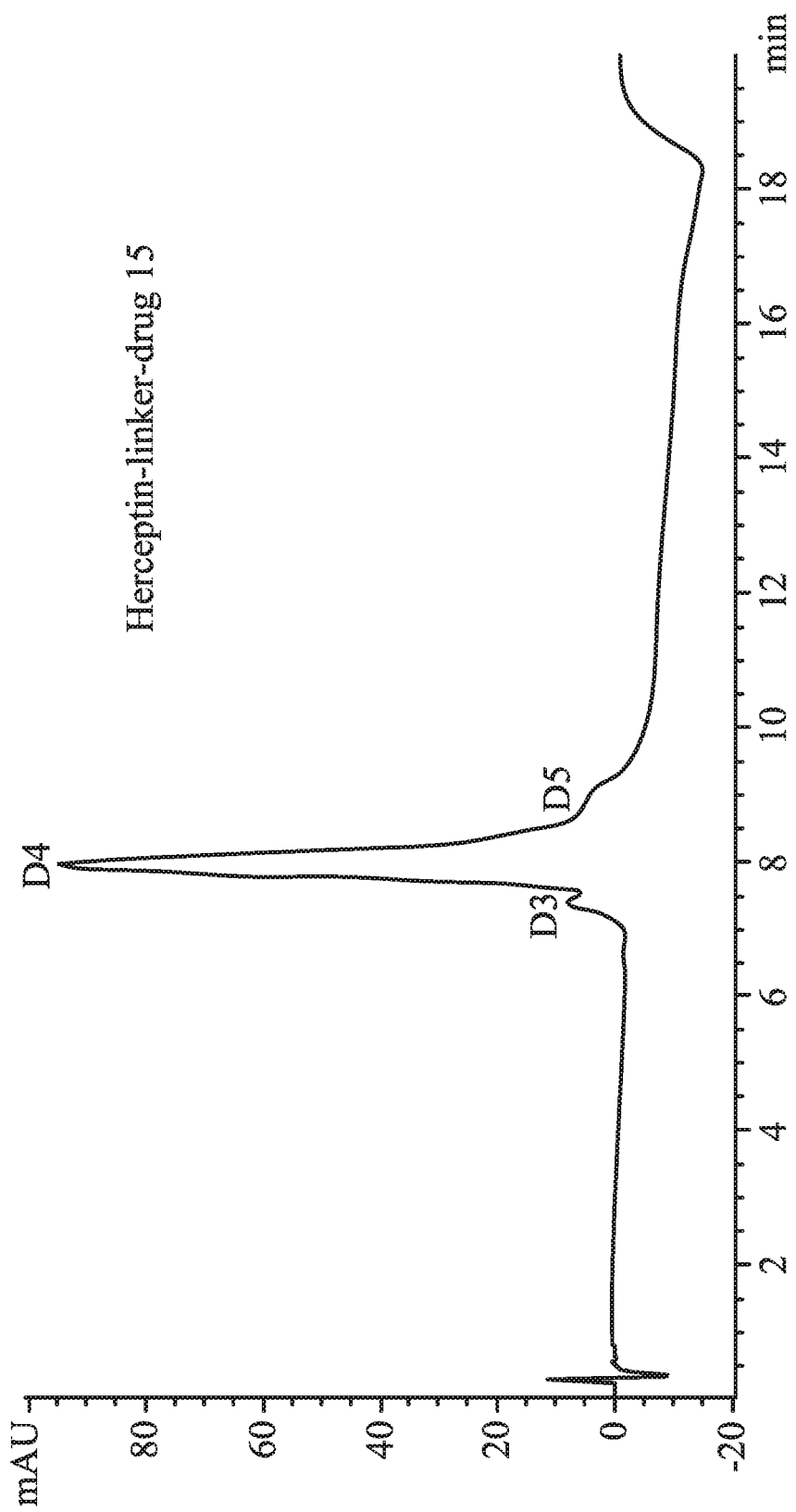
FIG. 12 shows a HIC profile of Herceptin-Linker-drug 15 in accordance with one embodiment of the present disclosure.

FIG. 12 shows that the average DAR of Herceptin-Linker-drug 15 is about 4.0, and the D4 ratio is about 82%.

Example 29: Herceptin-Linker-Drug 16

Frozen crystal of antibody Herceptin (bought from Roche) was dissolved in DIW (initial concentration: 11.36 mg/mL). 40 μL of the antibody solution was treated with 3.07 μL of TCEP (5 molar equivalent) and stirred at 37° C. for 2 hours. A desalting column was used to remove extra TCEP in the reduced Herceptin and the buffer was changed to borate buffer. 16.0 μL of DMSO was added and mixed evenly. Then, 2.002 μL (13 molar equivalent) of 20 mM of Linker-drug 16 prepared in DMSO was added into the antibody solution at 0-4° C. for 24 hours (final concentration of organic solvent in the mixture solution was about 26.4%) to obtain the antibody-drug conjugate (ADC). A desalting column (ThermoFisher Scientific, MWCO: 40K) was used to purify the product ADC Herceptin-Linker-drug 16. During elution, the buffer was changed to PBS buffer (2.67 mM KCl, 1.47 mM $KH_2PO_4$, 137.93 mM NaCl, 8.06 mM $Na_2HPO_4\text{-}7H_2O$).

Figure 13:
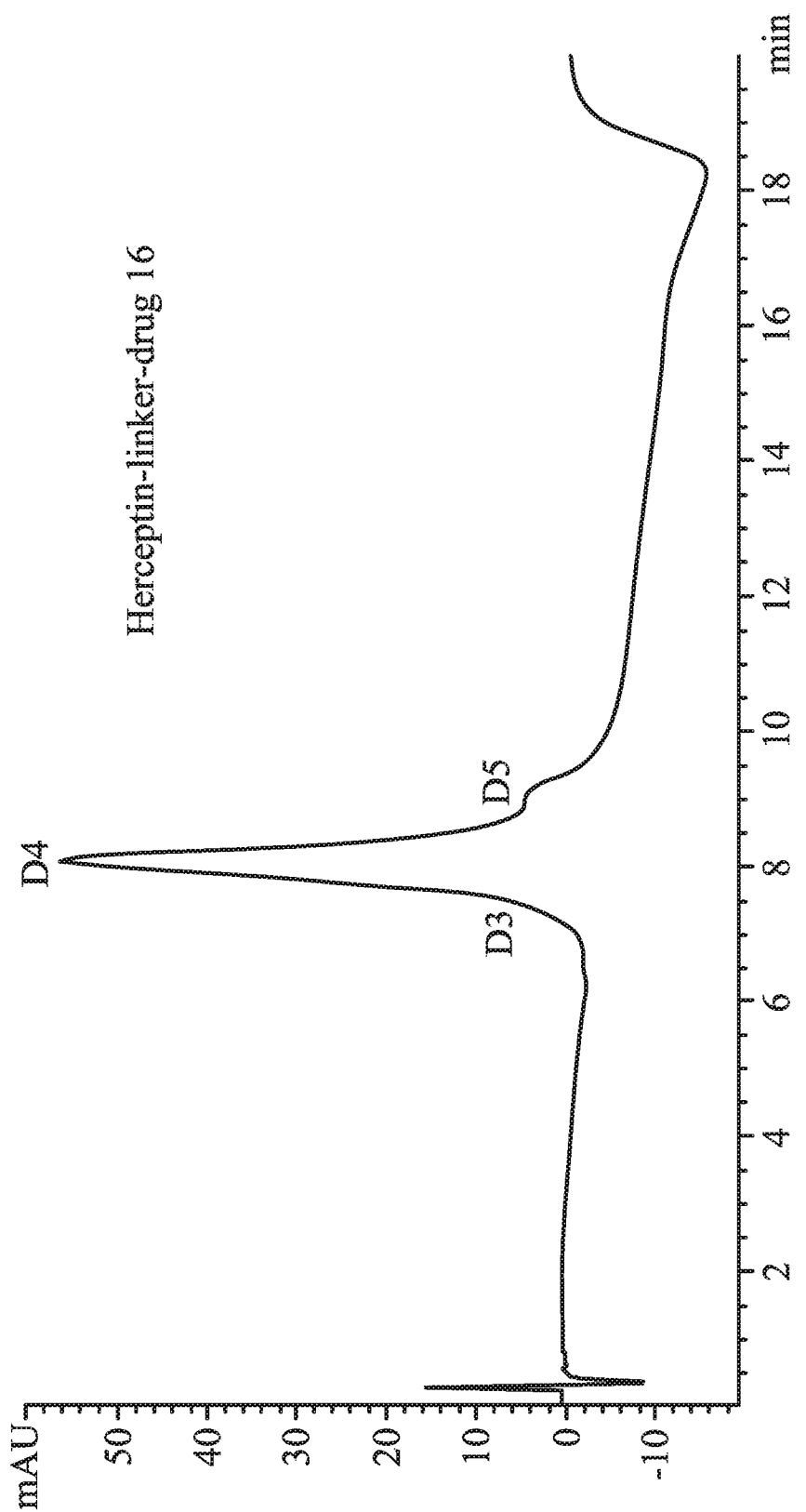
FIG. 13 shows a HIC profile of Herceptin-Linker-drug 16 in accordance with one embodiment of the present disclosure.
Figure 14:
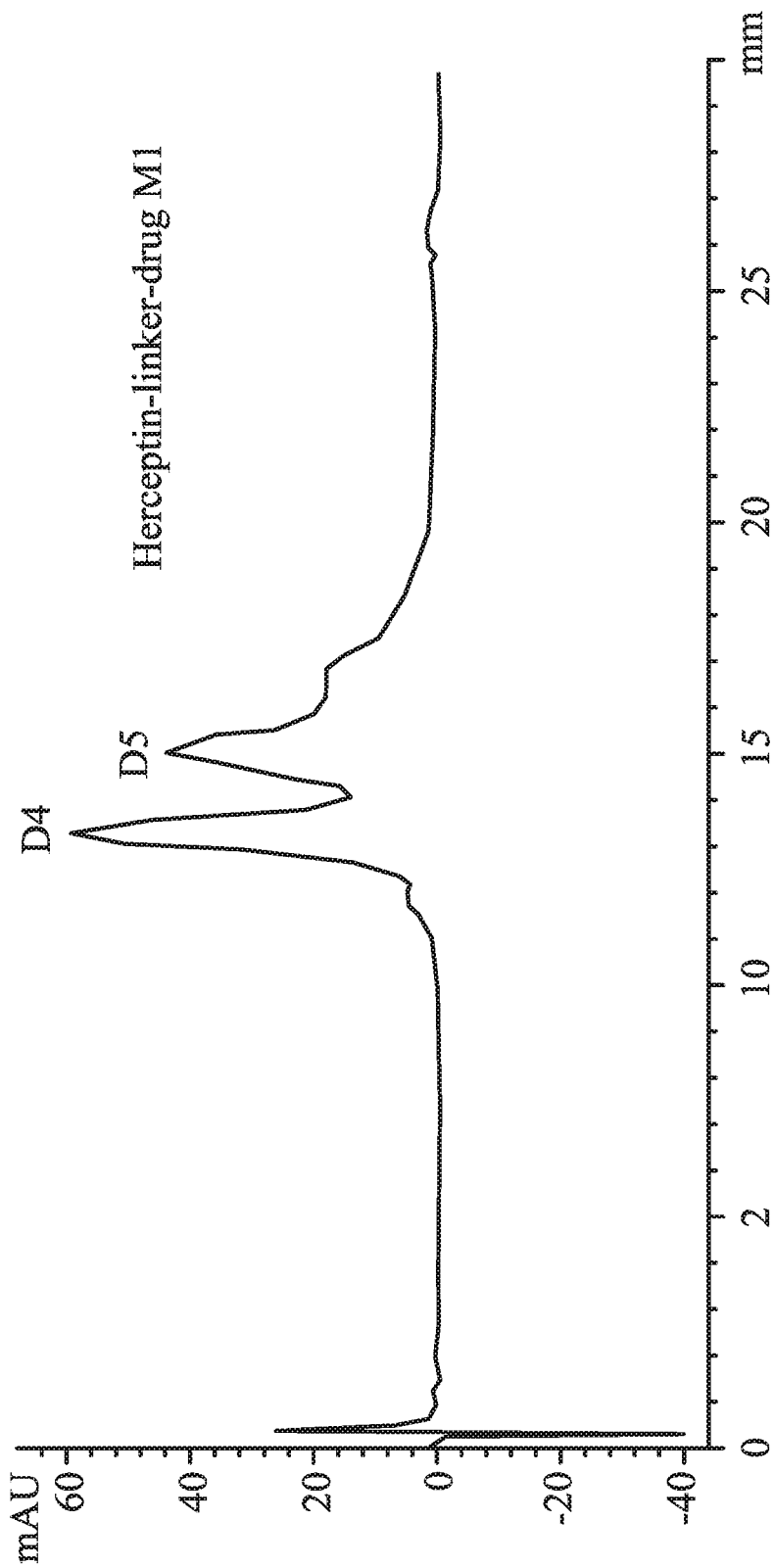
FIG. 14 shows a HIC profile of Herceptin-Linker-drug M1 in accordance with one embodiment of the present disclosure.

FIG. 13 shows that the average DAR of Herceptin-Linker-drug 16 is about 4.0, and the D4 ratio is about 81%.

<Storage Test>

20 mM Linker-drug 7 was stored in DMSO for 0, 21, 92 and 99 days at −20° C. LC-MS was used to analyze the purity of Linker-drug 7. The condition of LC-MS analysis was as follows.

Column: 4.6 mm×20 mm XBridge C18 column (Waters, Milford USA)
Flow rate: 700 μl/min
Linear gradient: 5 to 70% solvent B (100% acetonitrile with 0.1% formic acid)
Solvent A (0.1% formic acid in dd$H_2O$)
Solvent B (100% acetonitrile with 0.1% formic acid)

Figure 15:
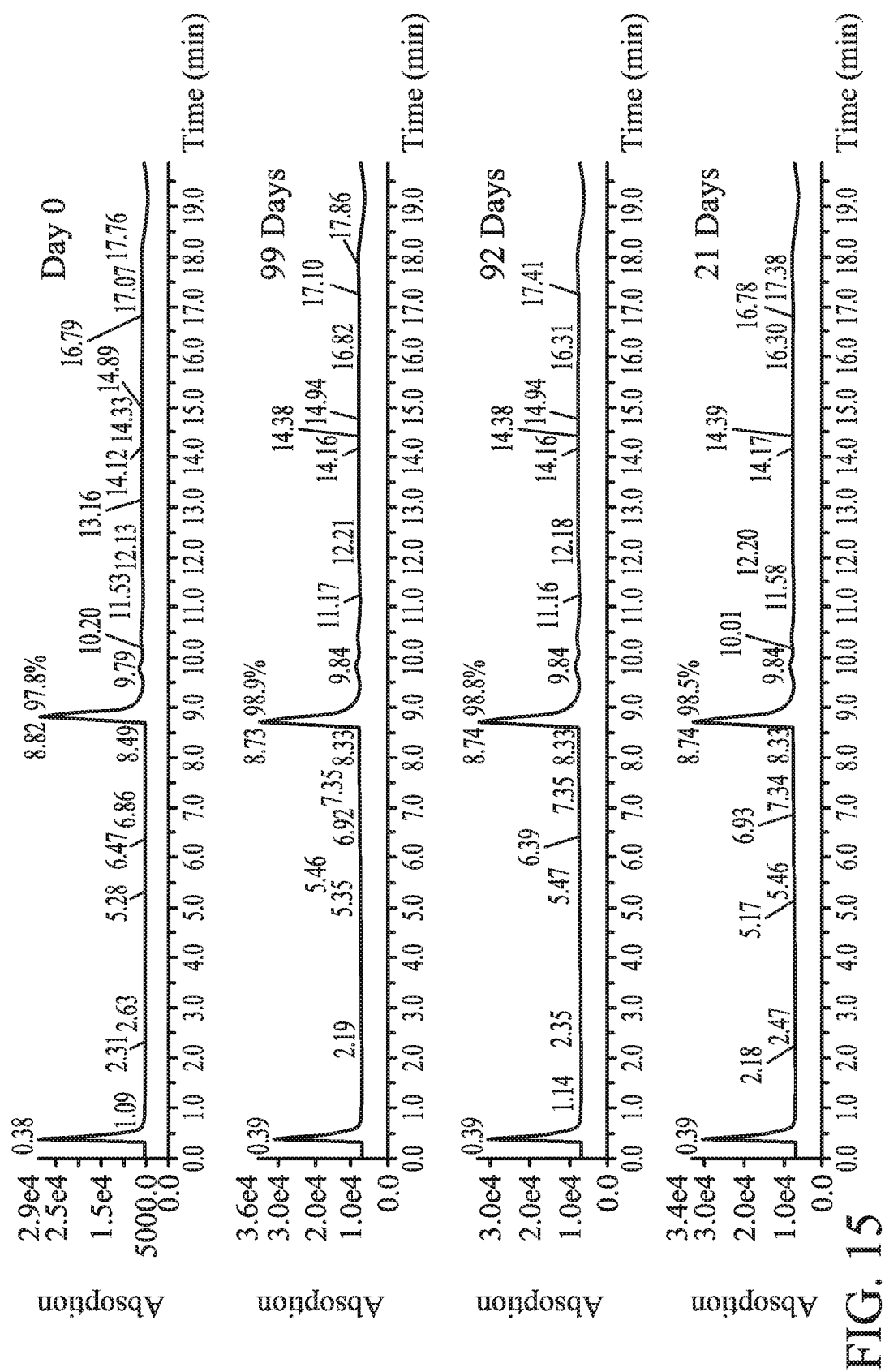
FIG. 15 shows results of s storage test of Herceptin-Linker-drug 7 in accordance with one embodiment of the present disclosure.

As shown in FIG. 15, the result of LC-MS analysis of Linker-drug 7 in different storage conditions shows that Linker-drug 7 was stable when dissolved in DMSO.

<Potency Test>

HER2-negative cell lines MDA-MB-468, HER2 moderate-expressing breast cancer cell lines JIMT-1 with anti-Herceptin® drug resistance, and HER2 high-expressing breast cancer cell lines BT-474 were treated with ADCs to analyze the selective toxicity of ADCs in these cells.

Cells were seeded in Corning CellBIND 96-well plates at densities of 6×10³ cells/well. After incubation overnight at 37° C., 5% $CO_2$ incubator, different concentrations of ADCs were added to the cells in serial dilutions. The cells were then incubated for 72-120 hours at 37° C., 5% $CO_2$ incubator. After 72-120 hours, the old medium was removed and the cells were rinsed once and treated with 10-fold diluted CCK-8 reagent at 37° C. for 4 hours. The 96-well plates were put in the ELISA reader to measure the absorbance wavelength at 450 nm. Cell viability was calculated by the following equation: Cell Viability (%)=(Intensity of sample/Intensity of control)×100%. IC50 values of the ADC samples were calculated using SigmaPlot software.

Figure 16:
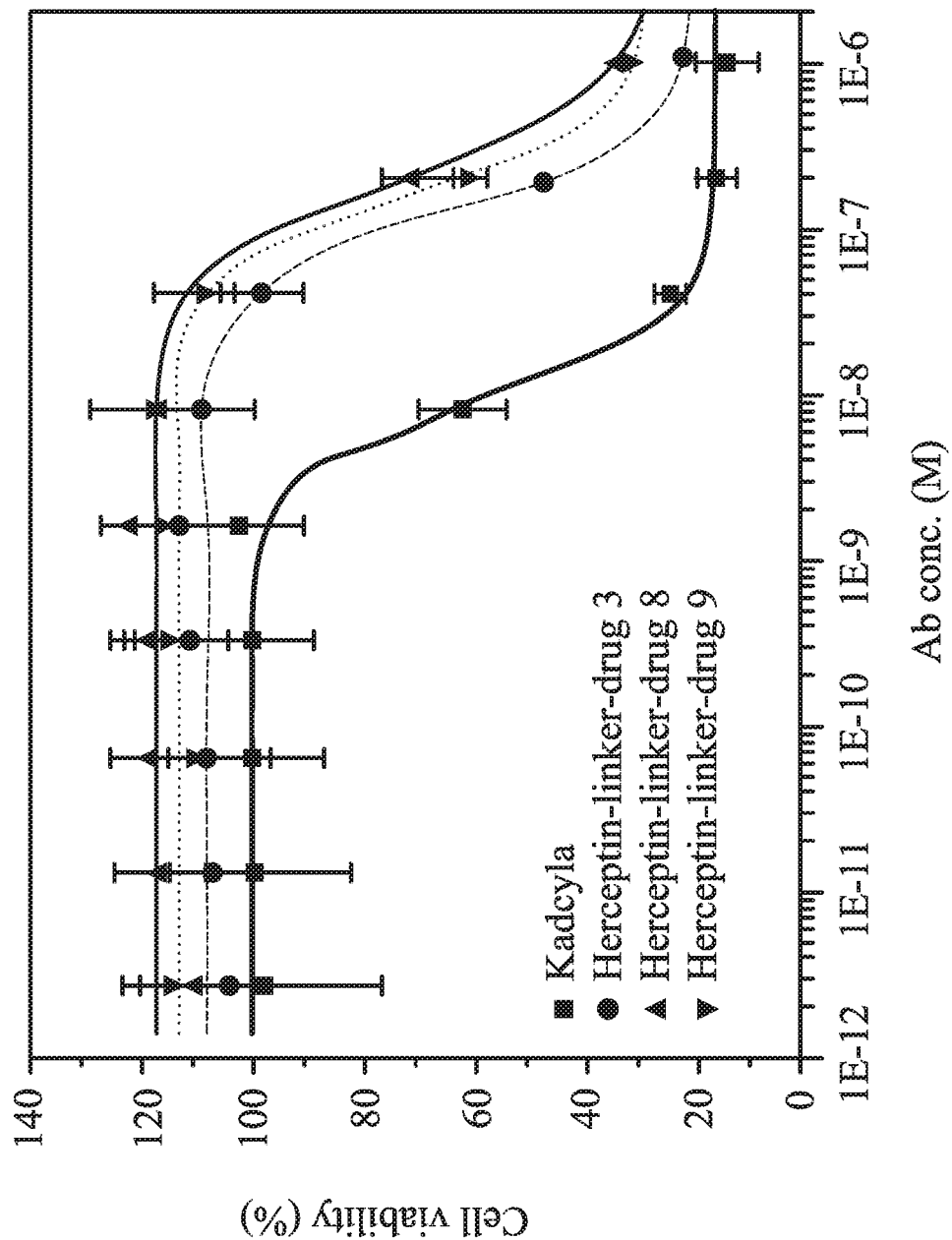
FIG. 16 shows the cell viability of MDA-MB-468 cells treated with ADCs (Herceptin-Linker-drug 3, Herceptin-Linker-drug 8, Herceptin-Linker-drug 9)

According to Table 3 and FIG. 16, the toxicity of Herceptin-Linker-drug 3, Herceptin-Linker-drug 8, and Herceptin-Linker-drug 9 in HER2-negative cell lines MDA-MB-468 is significantly lower than that of commercial Kadcyla.

Figure 17:
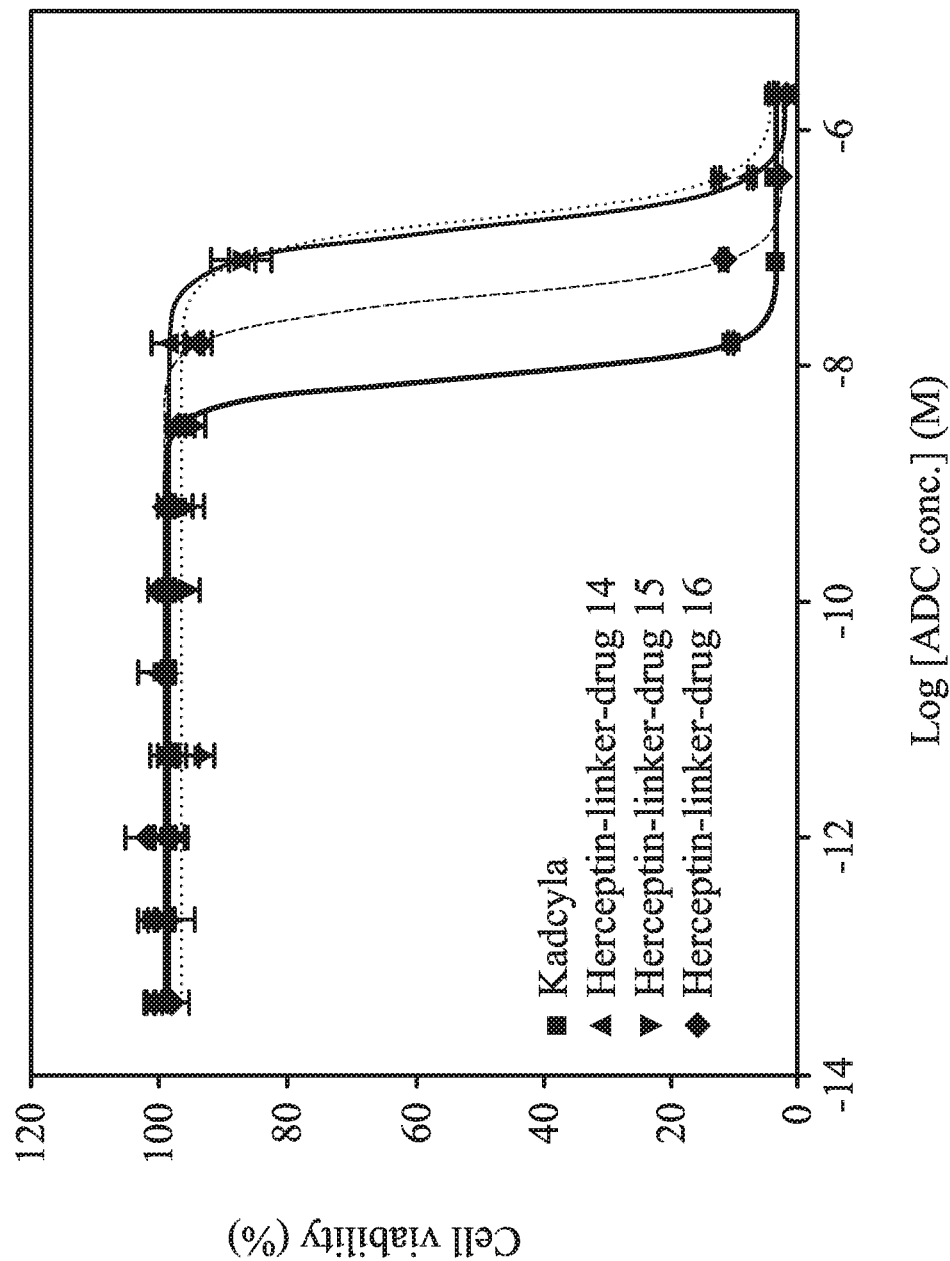
FIG. 17 shows the cell viability of MDA-MB-468 cells treated with ADCs (Herceptin-Linker-drug 14, Herceptin-Linker-drug 15, Herceptin-Linker-drug 16)

According to Table 4 and FIG. 17, the toxicity of Herceptin-Linker-drug 14, Herceptin-Linker-drug 15, and Herceptin-Linker-drug 16 in HER2-negative cell lines MDA-MB-468 is significantly lower than that of commercial Kadcyla.

Figure 18A:
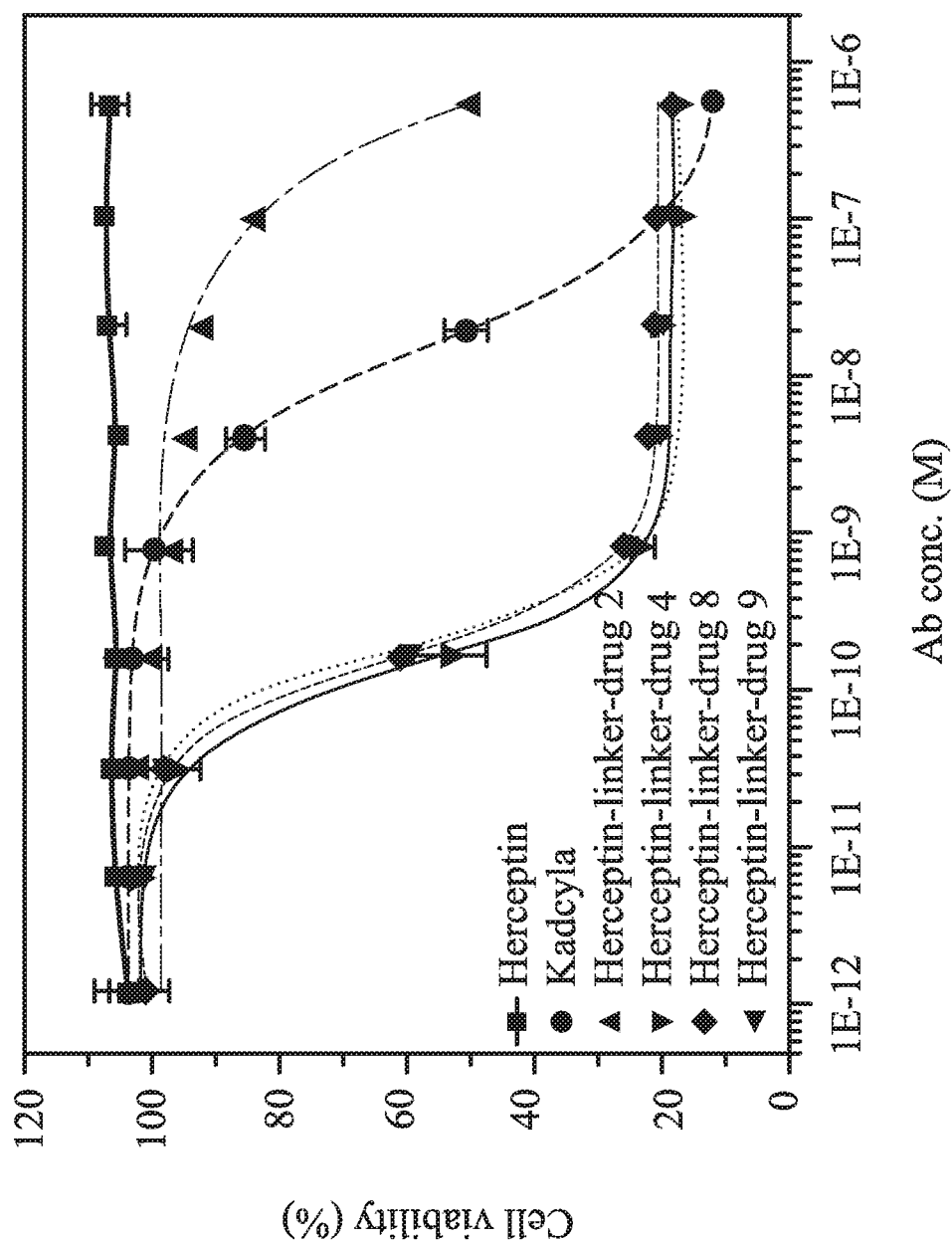
FIG. 18A shows the cell viability of JIMT-1 cells treated with ADCs (Herceptin-Linker-drug 2, Herceptin-Linker-drug 4, Herceptin-Linker-drug 8, Herceptin-Linker-drug 9)
Figure 18B:
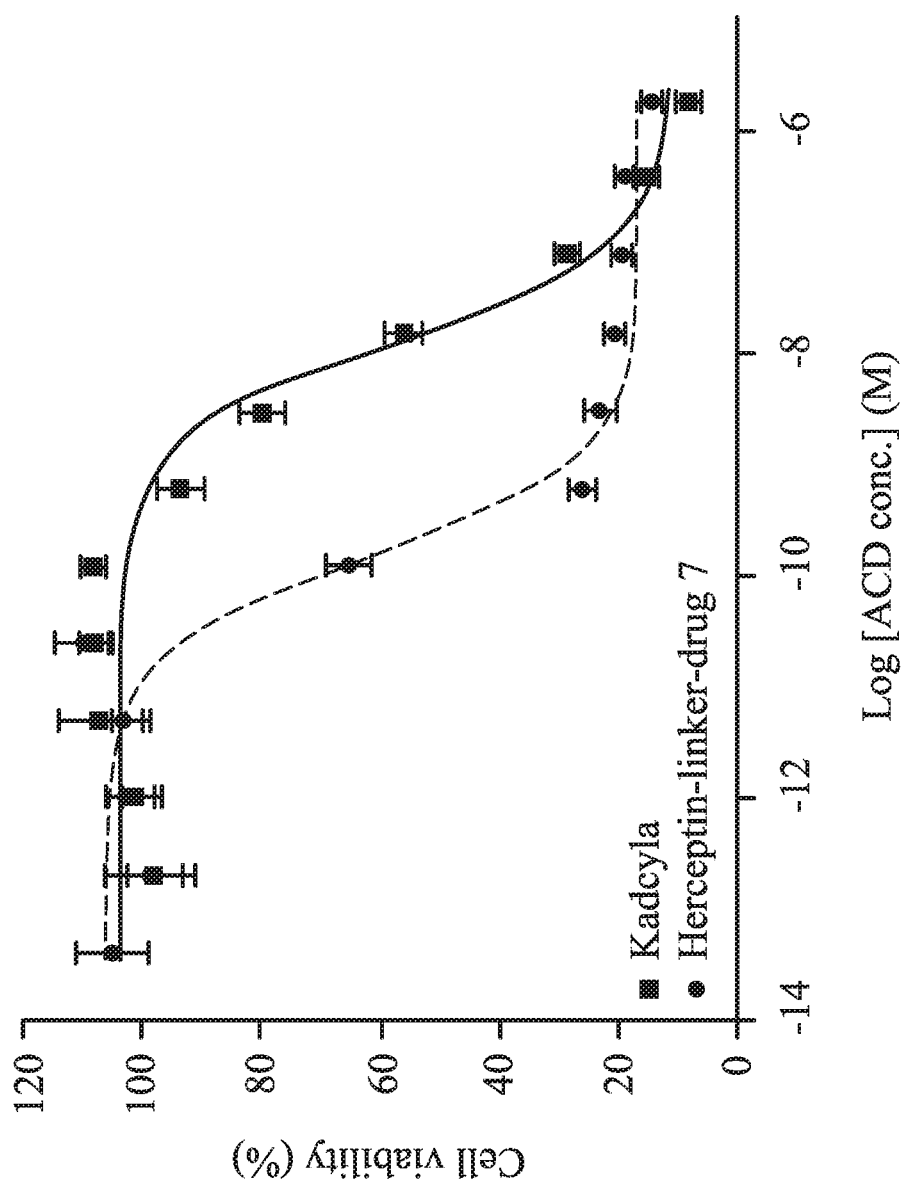
FIG. 18B shows the cell viability of JIMT-1 cells treated with ADC (Herceptin-Linker-drug 7)
Figure 18C:
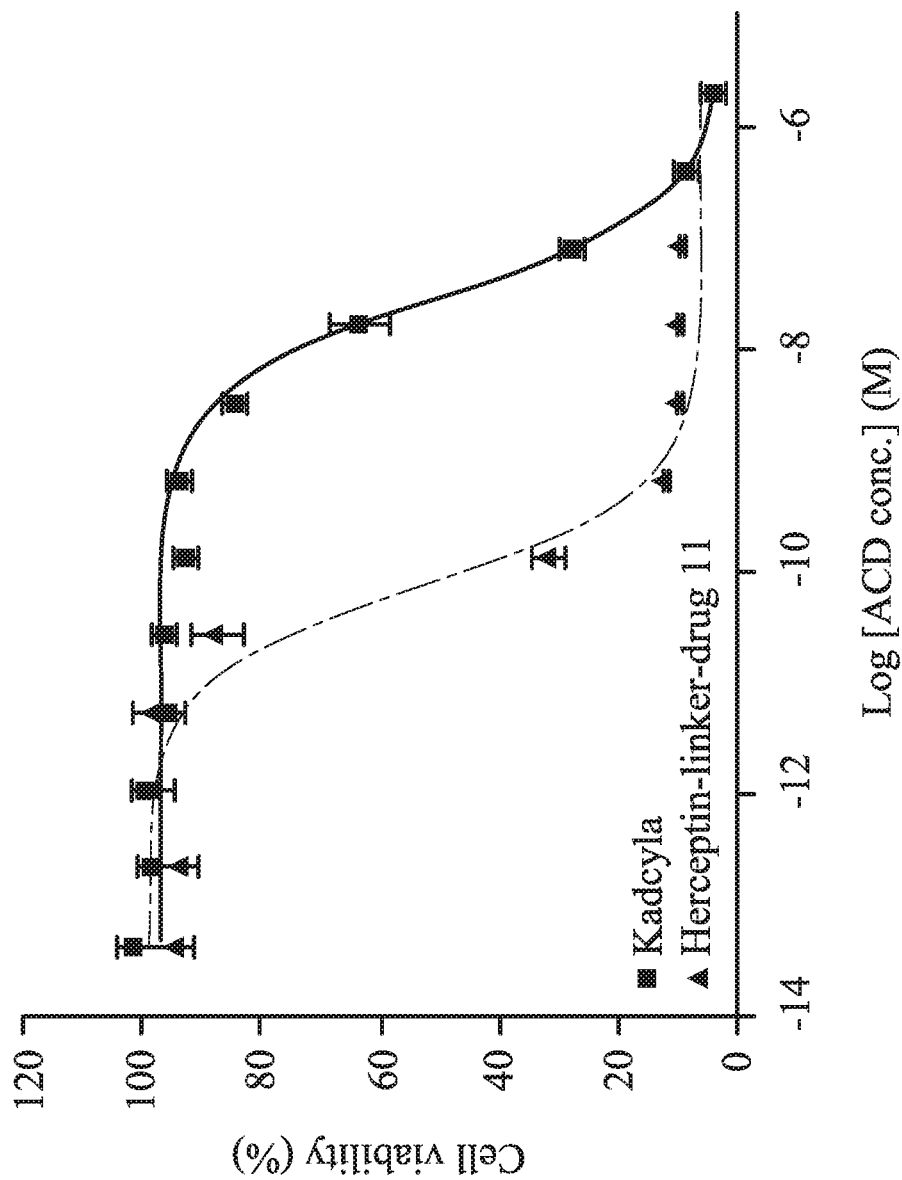
FIG. 18C shows the cell viability of JIMT-1 cells treated with ADC (Herceptin-Linker-drug 11)

Also, Table 3 and FIGS. 18A-18C show the IC50 values of Herceptin-Linker-drug 4, Herceptin-Linker-drug 7, Herceptin-Linker-drug 8, Herceptin-Linker-drug 9, and Herceptin-Linker-drug 11 in HER2 moderate-expressing breast cancer cell lines JIMT-1 are less than 0.5 nM. The potency of these ADCs in JIMT-1 cells is better than that of commercial Kadcyla. In particular, FIG. 18C shows the cell toxicity of Herceptin-Linker-drug 11, which has a high DAR value (DAR is about 8), is superior to the cell toxicity of other ADCs.

Figure 19:
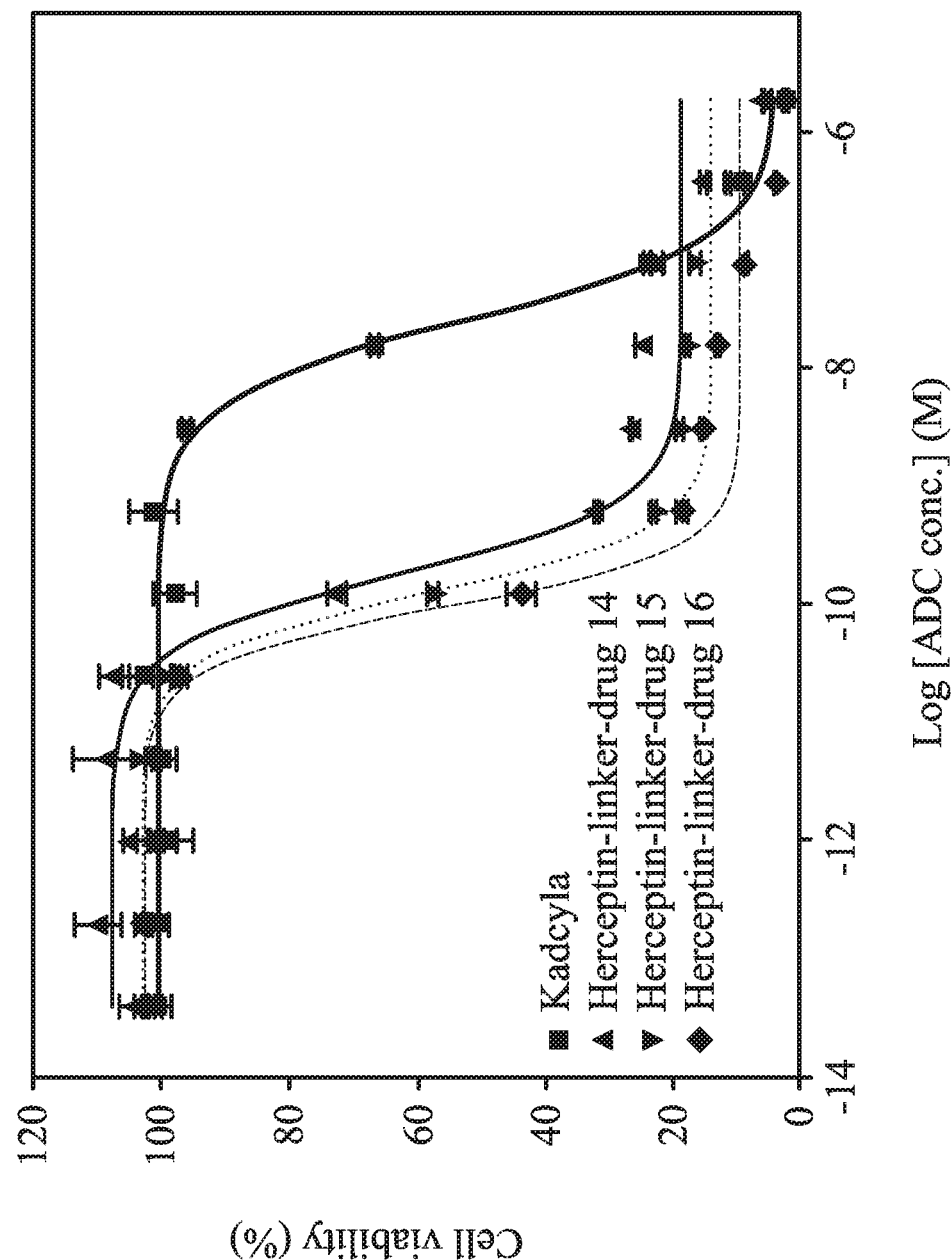
FIG. 19 shows the cell viability of JIMT-1 cells treated with ADC (Herceptin-Linker-drug 14, Herceptin-Linker-drug 15, Herceptin-Linker-drug 16)

Table 4 and FIG. 19 show the IC50 values of Herceptin-Linker-drug 14, Herceptin-Linker-drug 15, and Herceptin-Linker-drug 16 in HER2 moderate-expressing breast cancer cell lines JIMT-1 are less than 0.5 nM. The potency of these ADCs in JIMT-1 cells is better than that of commercial Kadcyla.

Figure 20A:
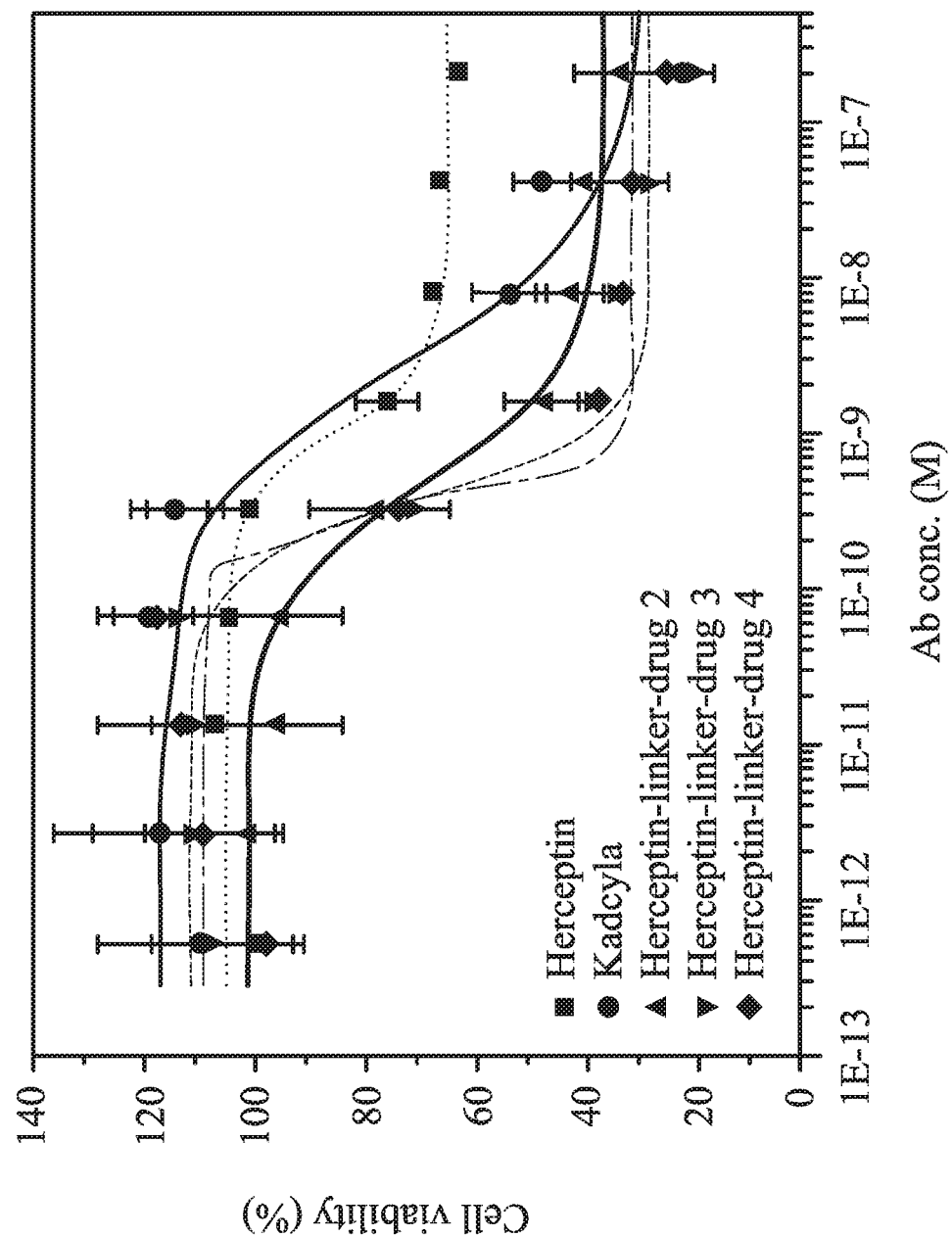
FIG. 20A shows the cell viability of BT-474 cells treated with ADC (Herceptin-Linker-drug 2, Herceptin-Linker-drug 3, Herceptin-Linker-drug 4)
Figure 20B:
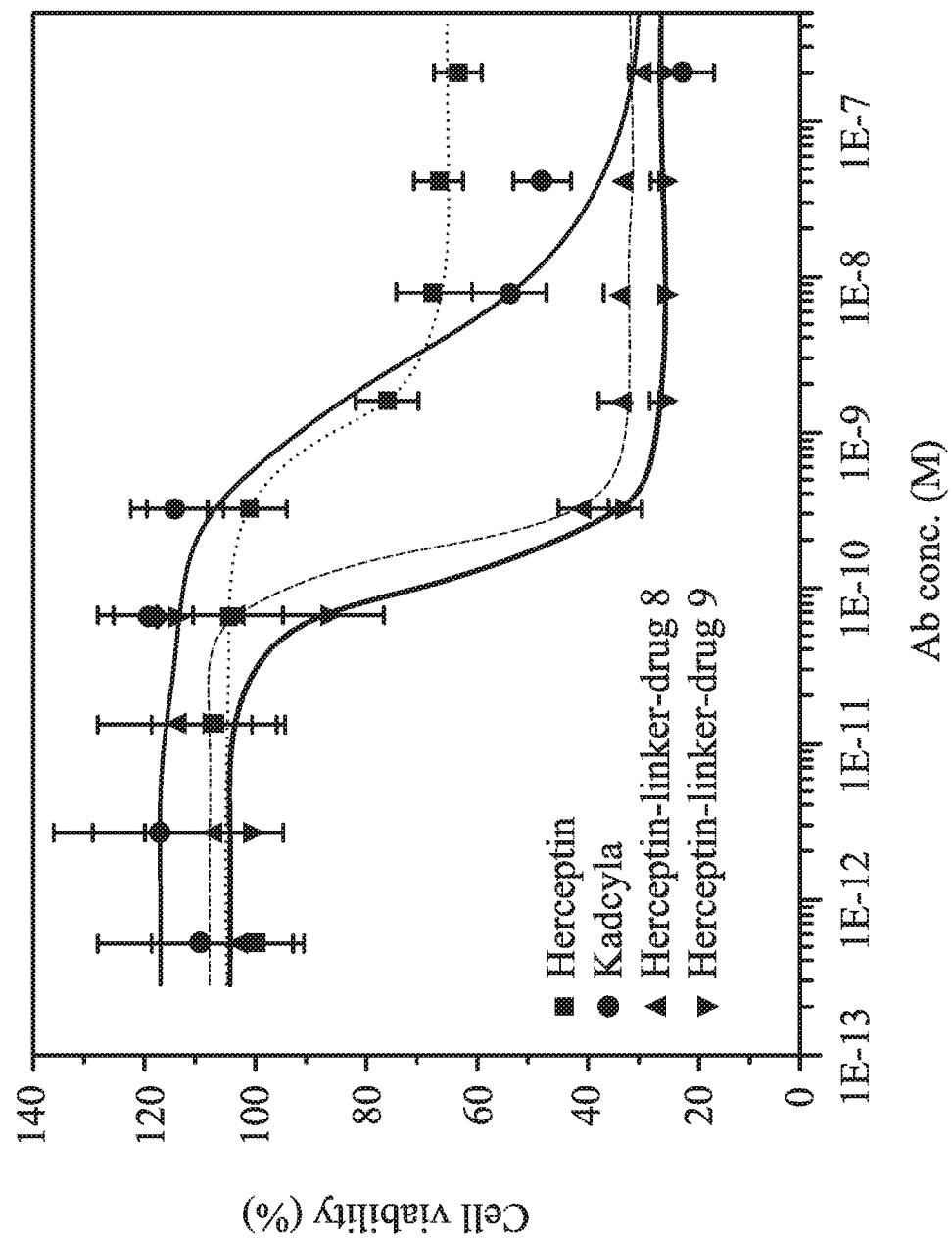
FIG. 20B shows the cell viability of BT-474 cells treated with ADC (Herceptin-Linker-drug 8, Herceptin-Linker-drug 9)
Figure 20C:
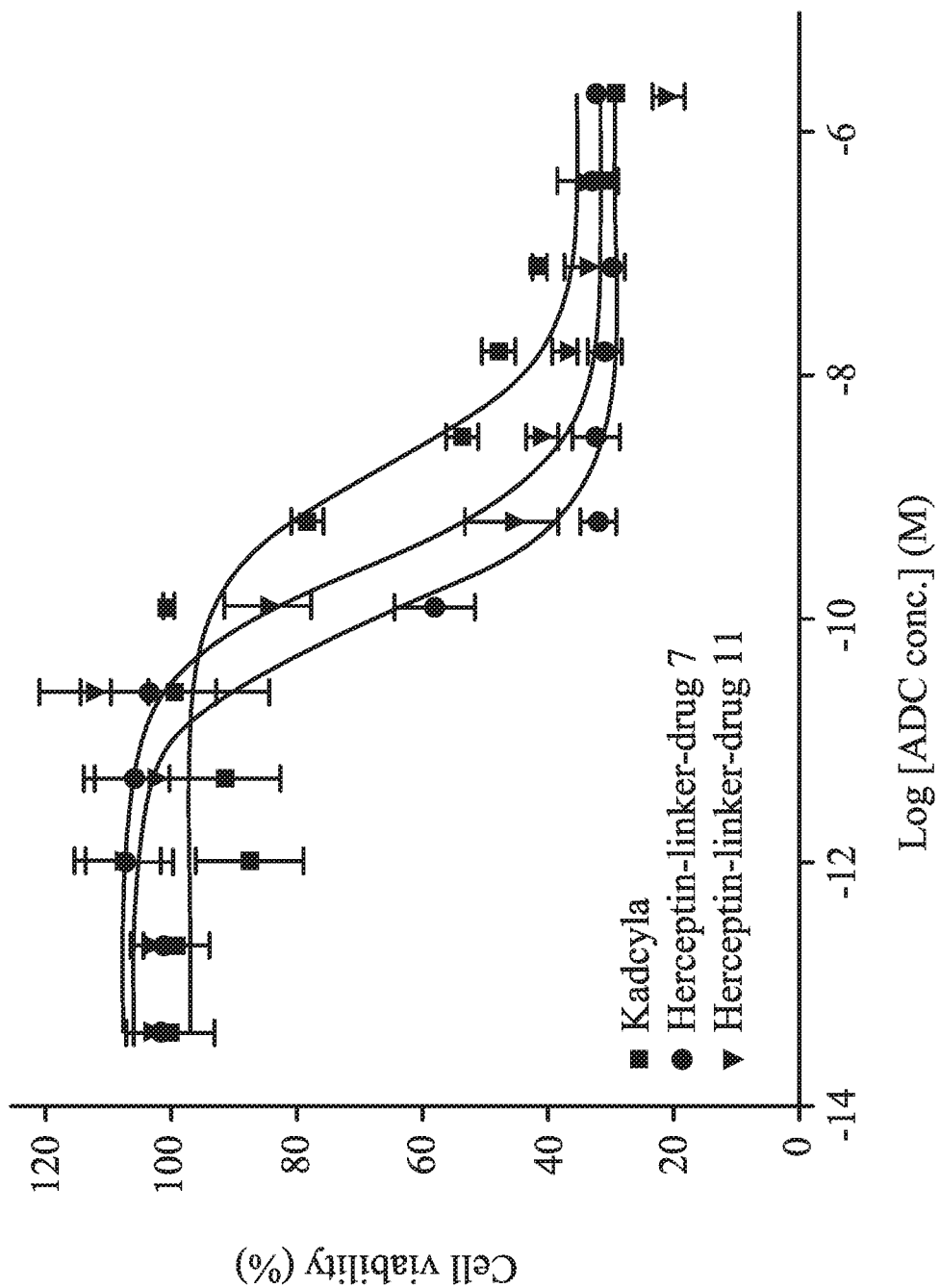
FIG. 20C shows the cell viability of BT-474 cells treated with ADC (Herceptin-Linker-drug 7, Herceptin-Linker-drug 11)

Moreover, Table 3 and FIGS. 20A-20C show the IC50 values of Herceptin-Linker-drug 2, Herceptin-Linker-drug 3, Herceptin-Linker-drug 4, Herceptin-Linker-drug 7, Herceptin-Linker-drug 8, Herceptin-Linker-drug 9, and Herceptin-Linker-drug 11 in HER2 high-expressing breast cancer cell lines BT-474 are less than 0.5 nM. The potency of these ADCs in BT-474 cells is better than that of commercial Kadcyla.

Figure 21:
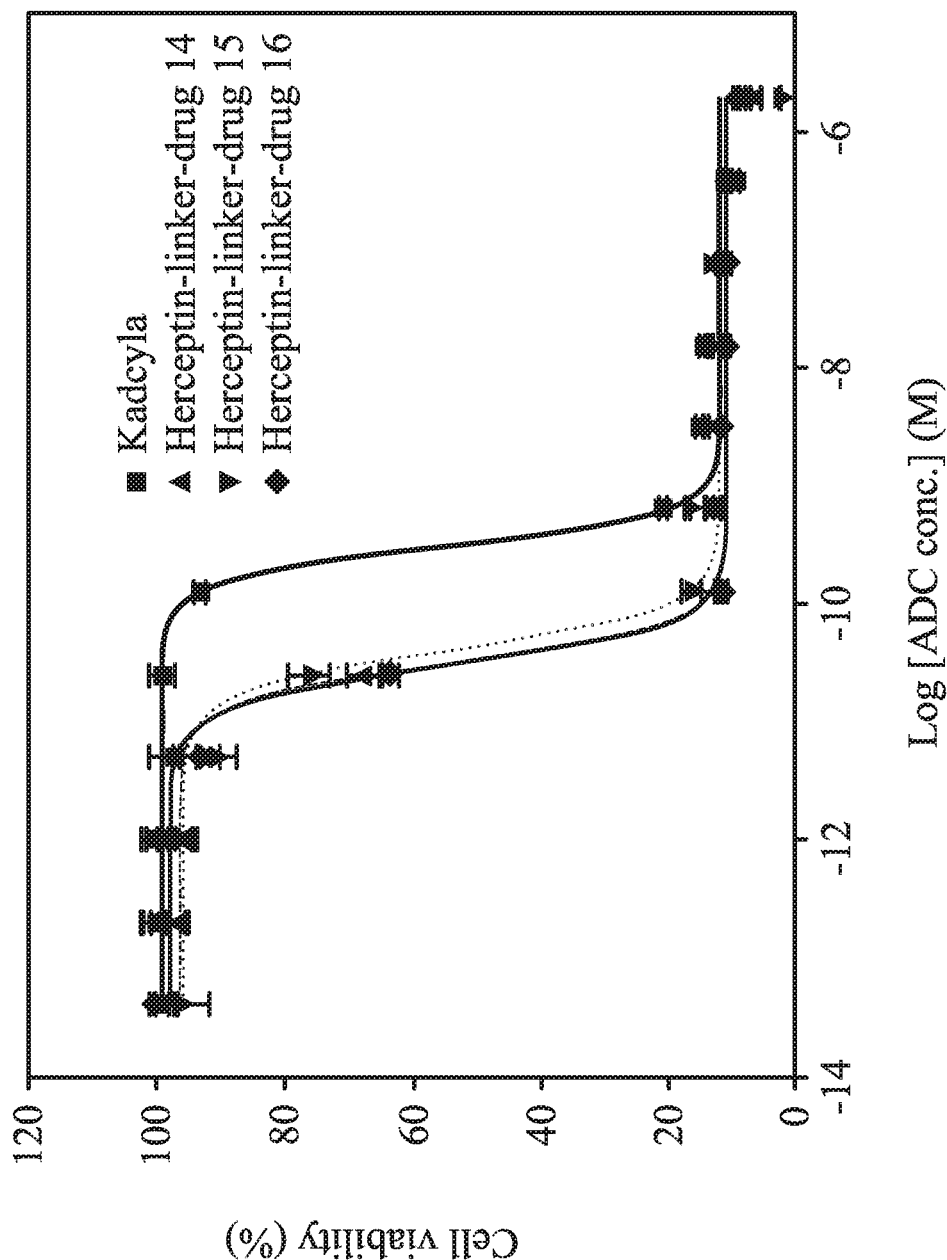
FIG. 21 shows the cell viability of BT-474 cells treated with ADC (Herceptin-Linker-drug 14, Herceptin-Linker-drug 15, Herceptin-Linker-drug 16)

Table 4 and FIG. 21 show the IC50 values of Herceptin-Linker-drug 14, Herceptin-Linker-drug 15, and Herceptin-Linker-drug 16 in HER2 high-expressing breast cancer cell lines BT-474 are less than 0.1 nM. The potency of these ADCs in BT-474 cells is better than that of commercial Kadcyla.

The results show that the site-specific ADCs in Table 3 have good selective toxicity in HER2 moderate-expressing breast cancer cell lines JIMT-1 and HER2 high-expressing breast cancer cell lines BT-474.

TABLE 3

| IC50 (nM) | MDA-MB-468 HER2 expression negative | BT-474 HER2 expression 3+ | JIMT-1 2+ resistant | In vitro selectivity MDA-MB-468/BT-474 | In vitro selectivity MDA-MB-468/JIMT-1 |
|---|---|---|---|---|---|
| Kadcyla | 15.2 | 2.27 | 15.5 | 5.5 | 1 |
| Herceptin-Linker-drug 2 | 598.2 | 0.43 | ~500 | 1391 | 1.2 |
| Herceptin-Linker-drug 3 | 128.5 | 0.35 | — | 367 | — |
| Herceptin-Linker-drug 4 | 485.3 | 0.38 | 0.14 | 1277 | 3466 |
| Herceptin-Linker-drug 7 | 489.9 | 0.10 | 0.17 | 4899 | 2882 |
| Herceptin-Linker-drug 8 | 156.6 | 0.11 | 0.19 | 1424 | 824 |

TABLE 3-continued

| IC50 (nM) | MDA-MB-468 HER2 expression negative | BT-474 3+ | JIMT-1 2+ resistant | In vitro selectivity MDA-MB-468/BT-474 | In vitro selectivity MDA-MB-468/JIMT-1 |
|---|---|---|---|---|---|
| Herceptin-Linker-drug 9 | 204.8 | 0.16 | 0.16 | 1280 | 1280 |
| Herceptin-Linker-drug 11 | 173.5 | 0.28 | 0.077 | 620 | 2253 |

TABLE 4

| IC50 (nM) | MDA-MB-468 HER2 expression negative | BT-474 3+ | JIMT-1 2+ resistant | In vitro selectivity MDA-MB-468/BT-474 | In vitro selectivity MDA-MB-468/JIMT-1 |
|---|---|---|---|---|---|
| Kadcyla | 8.11 | 0.31 | 27.04 | 26.16 | 0.30 |
| Herceptin-Linker-drug 14 | 154.2 | 0.033 | 0.18 | 4672.7 | 856.7 |
| Herceptin-Linker-drug 15 | 174.1 | 0.041 | 0.13 | 4246.3 | 1339.2 |
| Herceptin-Linker-drug 16 | 38.66 | 0.031 | 0.10 | 1247.1 | 386.6 |

<Tumor Growth Inhibition Test: BT-474 Xenograft Model>

$1 \times 10^7$ of breast cancer cell lines BT-474 were subcutaneous injected to NODSCID mice to test the drug efficacy of ADCs in vivo.

First, female mice were implanted with estradiol reagent pellets (0.36 mg/pellet; 90 days release, Innovative Research of America). BT-474 cells were then subcutaneous injected to mice and waited for tumor growth. The length and width of the tumor were measured and the tumor size was calculated by (length×width×width×½) (mm³) and recorded. When the average tumor size was about 359 mm³, vehicle (DPBS), 10 mg/kg Kadcyla (bought from Roche), 5 mg/kg Herceptin-Linker-drug 5, 2.5 mg/kg Herceptin-Linker-drug 5, 5 mg/kg Herceptin-Linker-drug 8, 2.5 mg/kg Herceptin-Linker-drug 8 were intravenously injected (10 mL/kg B.W. injection volume) twice at Day 0 and Day 21 for the pharmacodynamic experiment.

Tumor growth and body weight of the mice were observed until Day 60. The calculation formula of Tumor Growth Inhibition (TGI) is TGI (%)=[1−(Δdrug treated group tumor volume/Δvehicle group tumor volume)]×100 (%). During the experiment, if the tumor is more than 10% of body weight of mice, the tumor volume is more than 1500 mm³, or other adverse reactions occurred concurrently, mice were sacrificed using $CO_2$ due to humanitarian considerations.

Figure 22:
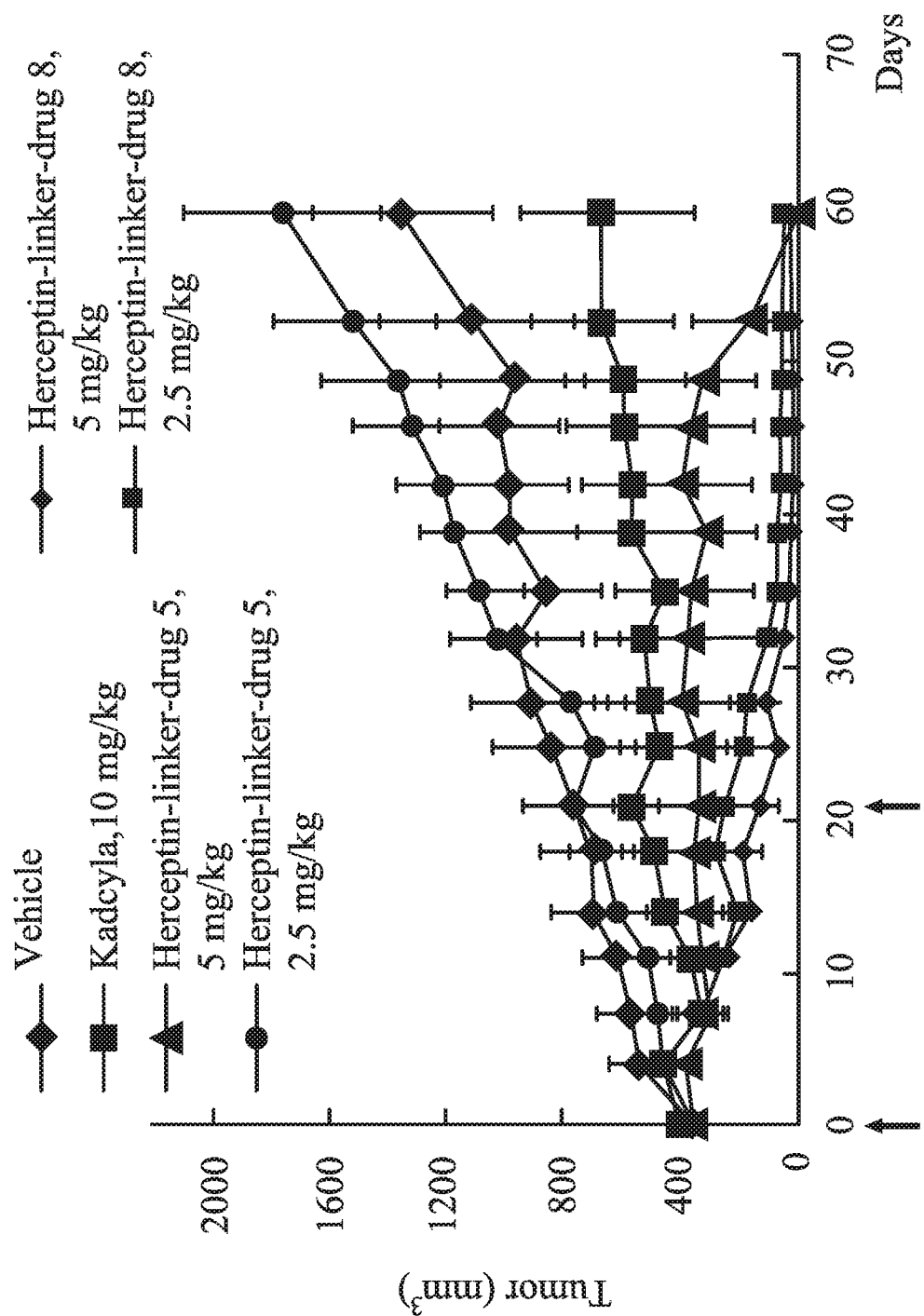
FIG. 22 shows the results of a tumor volume change of ADCs injected mice in a BT-474 xenograft model in accordance with some embodiments of the present disclosure.

After 60 days of treatments with ADCs, tumor growths of 5 mg/kg of Herceptin-Linker-drug 5, 5 mg/kg of Herceptin-Linker-drug 8, and 2.5 mg/kg of Herceptin-Linker-drug 8 treated groups were significantly inhibited. At Day 60, TGI of 5 mg/kg of Herceptin-Linker-drug 5, 5 mg/kg of Herceptin-Linker-drug 8, and 2.5 mg/kg of Herceptin-Linker-drug 8 treated groups were 133.8±9.4%, 141.7±14%, and 142.2±6.7%, respectively, while TGI of 10 mg/kg Kadcyla treated group was about 64% (referring to Table 5 and FIG. 22).

The results (referring to Table 6) showed that that no weight losing or other significant abnormal clinical symptoms occurred after ADCs administration.

TABLE 5

| Groups | TGI (%) ± SEM Day 0-60 | n |
|---|---|---|
| Vehicle (DPBS) | 0.0 | 6 |
| Kadcyla (10 mg/kg) | 64.1 ± 29.4 | 7 |
| Herceptin-Linker-drug 5 (5 mg/kg) | 133.8 ± 9.4 | 4 |
| Herceptin-Linker-drug 5 (2.5 mg/kg) | −82.3 ± 38.6 | 5 |
| Herceptin-Linker-drug 8 (5 mg/kg) | 141.7 ± 14 | 5 |
| Herceptin-Linker-drug 8 (2.5 mg/kg) | 142.2 ± 6.7 | 8 |

TABLE 6

| Groups | BW (%) ± SEM Day 0-60 | n |
|---|---|---|
| Vehicle (DPBS) | 104.4 ± 2.2 | 6 |
| Kadcyla (10 mg/kg) | 107.9 ± 2 | 7 |
| Herceptin-Linker-drug 5 (5 mg/kg) | 104.3 ± 1.2 | 4 |
| Herceptin-Linker-drug 5 (2.5 mg/kg) | 107.6 ± 2.8 | 5 |
| Herceptin-Linker-drug 8 (5 mg/kg) | 103.37 ± 3.9 | 5 |
| Herceptin-Linker-drug 8 (2.5 mg/kg) | 106.4 ± 3.4 | 8 |

<Tumor Growth Inhibition Test: EC PDX Model>

Endometrial cancer tumor tissue obtained from National Taiwan University was confirmed to be HER2-positive (+1). Tumor (2-3 mm diameter) was subcutaneous implanted to NODSCID mice to test the drug efficacy of ADCs in vivo.

Figure 23:
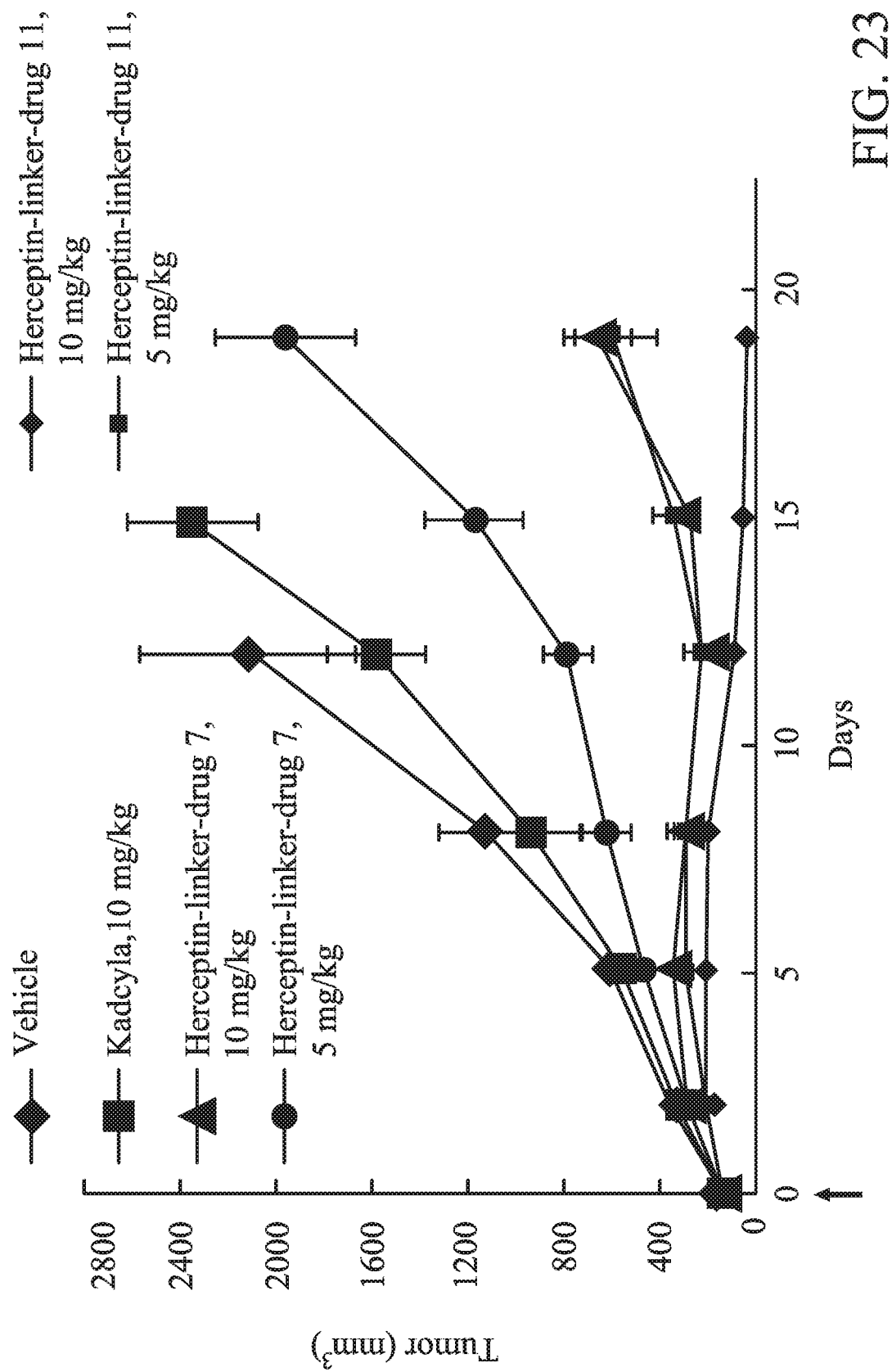
FIG. 23 shows the results of a tumor volume change of ADCs injected mice in an EC PDX model in accordance with some embodiments of the present disclosure.

When the average tumor size was about 100 mm³, mice were divided into groups and ADCs were intravenously injected (10 mL/kg B.W. injection volume). After 12 days of treatments with ADCs, tumor growths of 10 mg/kg of Herceptin-Linker-drug 7, 5 mg/kg of Herceptin-Linker-drug 7, 10 mg/kg of Herceptin-Linker-drug 11, and 5 mg/kg of Herceptin-Linker-drug 11 treated groups were significantly inhibited. At Day 12, TGI of 10 mg/kg of Herceptin-Linker-drug 7, 5 mg/kg of Herceptin-Linker-drug 7, 10 mg/kg of Herceptin-Linker-drug 11, and 5 mg/kg of Herceptin-Linker-drug 11 treated groups were 95.6±2.3%, 66.9±4.6%, 101.7±0.5%, and 95.0±3.2%, respectively, while TGI of 10 mg/kg Kadcyla treated group was 26.5±10.1% (referring to Table 7 and FIG. 23).

The results (referring to Table 8) showed that that no weight losing or other significant abnormal clinical symptoms occurred after Vehicle, 10 mg/kg Kadcyla, 10 mg/kg of Herceptin-Linker-drug 7, and 5 mg/kg of Herceptin-Linker-drug 7 administration. Although significant weight losing occurred after 10 mg/kg of Herceptin-Linker-drug 11 and 5 mg/kg of Herceptin-Linker-drug 11 administration, the abnormal clinical symptoms were recovered after one week.

TABLE 7

| Groups | TGI (%) ± SEM Day 0-60 | n |
|---|---|---|
| Vehicle (DPBS) | 0.0 | 6 |
| Kadcyla (10 mg/kg) | 26.5 ± 10.1 | 6 |
| Herceptin-Linker-drug 7 (10 mg/kg) | 95.6 ± 2.3 | 6 |
| Herceptin-Linker-drug 7 (5 mg/kg) | 66.9 ± 4.6 | 6 |

TABLE 7-continued

| Groups | TGI (%) ± SEM Day 0-60 | n |
|---|---|---|
| Herceptin-Linker-drug 11 (10 mg/kg) | 101.7 ± 0.5 | 6 |
| Herceptin-Linker-drug 11 (5 mg/kg) | 95.0 ± 3.2 | 6 |

TABLE 8

| Groups | BW (%) ± SEM Day 0-60 | n |
|---|---|---|
| Vehicle (DPBS) | 107.0 ± 1.5 | 6 |
| Kadcyla (10 mg/kg) | 102.0 ± 3.4 | 7 |
| Herceptin-Linker-drug 7 (10 mg/kg) | 102.6 ± 1.9 | 4 |
| Herceptin-Linker-drug 7 (5 mg/kg) | 100.7 ± 1.5 | 5 |
| Herceptin-Linker-drug 11 (10 mg/kg) | 96.3 ± 3.1 | 5 |
| Herceptin-Linker-drug 11 (5 mg/kg) | 100.7 ± 3.4 | 8 |

It will be apparent to those skilled in the art that various modifications and variations may be made to the disclosed embodiments. It is intended that the specification and examples be considered as exemplary only, with the true scope of the disclosure being indicated by the following claims and their equivalents.

What is claimed is:

1. A linker-drug represented by formula (IA) or formula (IA'):

(IA)

(IA')

wherein C is a conjugating linker; L is a linker unit; Do, Dp and Dq are drug units; and m is an integer of 1; o is an integer ranging from 1 to 4; p is an integer ranging from 1 to 4; and q is an integer ranging from 1 to 4; wherein the structure of the conjugating linker is represented by formula (IIa), formula (IIb), or formula (IIc):

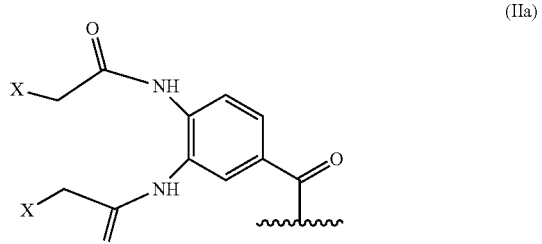

(IIa)

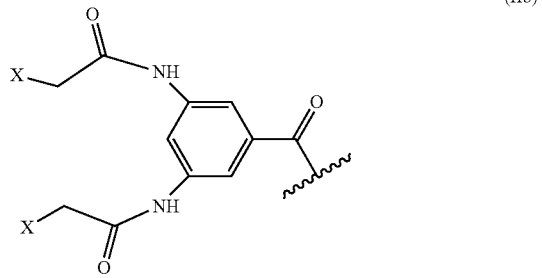

(IIb)

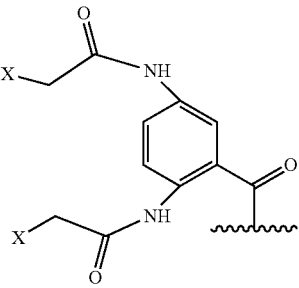

(IIc)

wherein X is a leaving group,
wherein the wave line of formula (IIa), formula (IIb), or formula (IIc) indicates the covalent attachment site to L.

2. The linker-drug as claimed in claim 1, wherein the linker unit is a cleavable linker or a noncleavable linker.

3. The linker-drug as claimed in claim 2, wherein the cleavable linker comprises a peptide unit (-AAs-) selected from a group consisting of -valline-citruline-(-Val-Cit-), -valline-lysine-(-Val-Lys-), -valline-arginine-(-Val-Arg-), -phenylalanine-citruline-(-Phe-Cit-), -phenylalanine -lysine- (-Phe-Lys-), and -phenylalanine-arginine-(-Phe-Arg-).

4. The linker-drug as claimed in claim 1,
wherein L is linear alkyl, cycloalkyl, heterocycloalkyl, alkenyl, alkynyl, aryl, heteroaryl, poly(ethylene glycol) chain, or a combination thereof; and Do, Dp and Dq are independently cytotoxic drugs, anti-autoimmune disease drugs, or anti-inflammation drugs.

5. The linker-drug as claimed in claim 1, wherein the drug unit is amanitins, anthracyclines, auristatins, baccatins, calicheamicins, camptothecins, cemadotins, colchicines, colcimids, combretastatins, cryptophycins, discodermolides, docetaxel, doxorubicin, duocarmycins, echinomycins, eleutherobins, epothilones, estramustines, lexitropsins, maytansines, maytansinoids, methotrexate, netropsins, pyrrolo [2,1-c][1,4]benzodi-azepines (PBDs), puromycins, rhizoxins, SN-38, taxanes, tubulysins, or vinca alkaloids.

6. The linker-drug as claimed in claim 1, wherein the leaving group is —Cl, —Br, —I, —F, —OTs, —OMs, —OTf or —OBs.

7. An antibody-drug conjugate (ADC) represented by formula (IVA) or formula (IVA'):

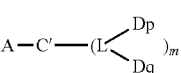

(IVA)

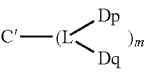

(IVA')

wherein A is a full-length antibody, or an antibody fragment; C'-(L-Do)m and

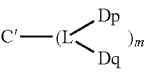

are linker-drugs, wherein C' is a conjugating linker; L is a linker unit; Do, Dp and Dq are drug units; and m is an integer of 1; o is an integer ranging from 1 to 4; p is an integer ranging from 1 to 4; and q is an integer ranging from 1 to 4;

wherein A is conjugated to the linker-drug through two thiol groups respectively present in two cysteine residues of A;

A-C' is the following structure represented by formula (Va), formula (Vb), or formula (Vc):

(Va)
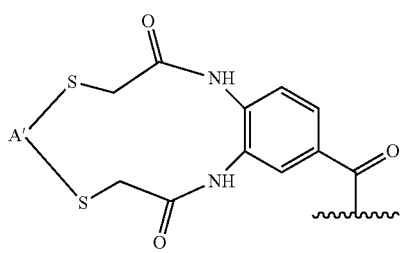

(Vb)
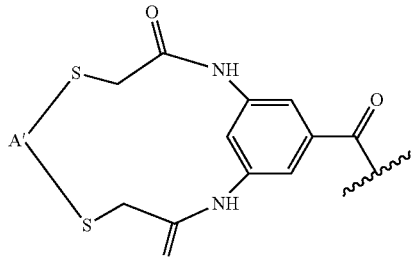

(Vc)
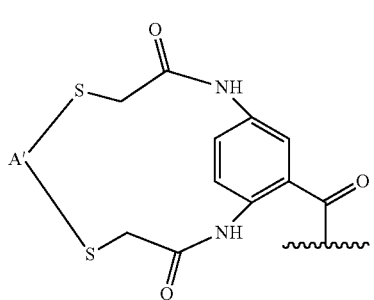

wherein the wave line of formula (Va), formula (Vb), or formula (Vc) indicates the covalent attachment site to L; A' indicates the remaining part of A which conjugated to the linker-drug through two thiol groups respectively present in two cysteine residues of A.

8. The antibody-drug conjugate (ADC) as claimed in claim 7, wherein A targets cell surface receptors or tumor-related antigens.

9. The antibody-drug conjugate (ADC) as claimed in claim 7, wherein the antibody is a chimeric antibody or a functionally active fragment thereof, a humanized antibody or a functionally active fragment thereof, a human antibody or a functionally active fragment thereof, a mouse antibody or a functionally active fragment thereof, a rat antibody or a functionally active fragment thereof, a goat antibody or a functionally active fragment thereof, or a rabbit antibody or a functionally active fragment thereof.

10. The antibody-drug conjugate (ADC) as claimed in claim 7, wherein the antibody is an IgG1 antibody or a functionally active fragment thereof, an IgG4 antibody or a functionally active fragment thereof.

11. The antibody-drug conjugate (ADC) as claimed in claim 7, wherein the antibody is HLX-07, EG12014, anti-EpCAM Ab and IgG1, Rituximab, Ibritumomab tiuxetan, Tositumomab, Brentuximab, Alemtuzumab, IGN101, Adecatumumab, Labetuzumab, huA33, Pemtumomab, Oregovomab, CC49 (minretumomab), cG250, J591, MOv18, Farletuzumab (MORAb-003), 3F8, ch14.18, KW-2871, hu3S193, IgN311, Bevacizumab, IM-2C6, CDP791, Etaracizumab, Volociximab, Cetuximab, Panitumumab, Nimotuzumab, 806, Trastuzumab, Pertuzumab, MM-121, AMG 102, METMAB, SCH 900105, AVE1642, IMC-A12, MK-0646, R1507, CP 751871, KB004, IIIA4, Mapatumumab (HGS-ETR1), Lexatumumab (HGS-ETR2), CS-1008, Denosumab, Sibrotuzumab, F19, 8106, humanized anti HER2 mAb, Edrecolomab, Cetuximab, Smart MI95, LymphoCide, Smart ID10, Oncolym, Allomune, or Epratuzamab.

12. The antibody-drug conjugate (ADC) as claimed in claim 7, wherein the linker unit is a cleavable linker or a noncleavable linker.

13. The antibody-drug conjugate (ADC) as claimed in claim 12, wherein the cleavable linker comprises a peptide unit (-AAs-) selected from a group consisting of -valline-citruline-(-Val-Cit-), -valline-lysine-(-Val-Lys-), -valline-arginine-(-Val-Arg-), -phenylalanine-citruline-(-Phe-Cit-), -phenylalanine-lysine-(-Phe-Lys-), and -phenylalanine-arginine-(-Phe-Arg-).

14. The antibody-drug conjugate (ADC) as claimed in claim 7,
wherein L is linear alkyl, cycloalkyl, heterocycloalkyl, alkenyl, alkynyl, aryl, heteroaryl, poly(ethylene glycol) chain, or a combination thereof; and Do, Dp and Dq are independently cytotoxic drugs, anti-autoimmune disease drugs, or anti-inflammation drugs.

15. The antibody-drug conjugate (ADC) as claimed in claim 7, wherein the drug unit is amanitins, anthracyclines, auristatins, baccatins, calicheamicins, camptothecins, cemadotins, colchicines, colcimids, combretastatins, cryptophycins, discodermolides, docetaxel, doxorubicin, duocarmycins, echinomycins, eleutherobins, epothilones, estramustines, lexitropsins, maytansines, maytansinoids, methotrexate, netropsins, pyrrolo[2,1-c][1,4]benzodiazepines (PBDs), puromycins, rhizoxins, SN-38, taxanes, tubulysins, or vinca alkaloids.

16. The antibody-drug conjugate (ADC) as claimed in claim , wherein the average DAR of the antibody-drug conjugate is about 3-8.

* * * * *